United States Patent
Martinelli et al.

(10) Patent No.: US 12,168,640 B2
(45) Date of Patent: Dec. 17, 2024

(54) USP9X INHIBITORS

(71) Applicant: ProDeg, LLC, Belmont, MA (US)

(72) Inventors: Richard Martinelli, Belmont, MA (US); Julian F. Bond, Weymouth, MA (US)

(73) Assignee: ProDeg, LLC, Belmont, MA (US)

(*) Notice: Subject to any disclaimer, the term of this patent is extended or adjusted under 35 U.S.C. 154(b) by 0 days.

(21) Appl. No.: 18/404,037

(22) Filed: Jan. 4, 2024

(65) Prior Publication Data

US 2024/0294467 A1 Sep. 5, 2024

Related U.S. Application Data

(63) Continuation-in-part of application No. 18/095,161, filed on Jan. 10, 2023, now abandoned, which is a continuation-in-part of application No. 17/988,230, filed on Nov. 16, 2022, now Pat. No. 11,691,945.

(60) Provisional application No. 63/279,783, filed on Nov. 16, 2021.

(51) Int. Cl.
| | |
|---|---|
| C07C 237/40 | (2006.01) |
| C07D 207/04 | (2006.01) |
| C07D 211/70 | (2006.01) |
| C07D 213/04 | (2006.01) |
| C07D 231/12 | (2006.01) |
| C07D 233/58 | (2006.01) |
| C07D 265/30 | (2006.01) |
| C07D 471/04 | (2006.01) |

(52) U.S. Cl.
CPC .......... *C07C 237/40* (2013.01); *C07D 207/04* (2013.01); *C07D 211/70* (2013.01); *C07D 213/04* (2013.01); *C07D 231/12* (2013.01); *C07D 233/58* (2013.01); *C07D 265/30* (2013.01); *C07D 471/04* (2013.01)

(58) Field of Classification Search
CPC ............................ C07C 233/87; A61K 31/167
See application file for complete search history.

(56) References Cited

U.S. PATENT DOCUMENTS

| | | |
|---|---|---|
| 2007/0149446 A1 | 6/2007 | Joullie |
| 2010/0152099 A1 | 6/2010 | Lee et al. |
| 2021/0214373 A1 | 7/2021 | Cui et al. |

FOREIGN PATENT DOCUMENTS

WO   2020191022 A1   9/2020

OTHER PUBLICATIONS

STN registry (RN# 2253619-82-6, entered date: Dec. 17, 2018).*
Pubchem, SID 133858068, deposited Jan. 25, 2012.
Pubchem, SID 311054015, deposited Feb. 23, 2016.
11-Oxa-3, 16-diazatricyclo[15.3.1.16, 10]docosa-1(21),6(22),7,9, 17, 19-hexaen-2-one, Pubchem CID 142691025. Pubchem entry (online) Dec. 7, 2019; Retrieved on Mar. 21, 2023 from the Internet: [URL: https://pubchem.ncbi.nlm.nih.gov/compound/142691025], 1-8.
"3-(2-Aminoethoxy)benzamide", Pubchem CID 28810201. Pubchem entry (online), May 28, 2009; Retrieved on Mar. 21, 2023 from the Internet: [URL: https://pubchem.ncbi.nlm.nih.gov/compound/28810201], 1-10.
"Propanediamide, N,N'-1-diphenyl-", Pubchem CID 69298. Pubchem entry (online), pp. 1-9, Mar. 26, 2005; Retrieved on Mar. 21, 2023 from the Internet: [URL: https://pubchem.ncbi.nlm.nih.gov/compound/69298].
Hogarty, M., "Mcl1 Becomes Ubiquitin-ous: New Opportunities to Antagonize a Pro-Survival Protein", Cell Res., vol. 20, No. 4, 391-393, 2010.
Jingjing, W., et al., "Deubiquitination and Stabilization of Programmed Cell Death Ligand 1 by Ubiquitin-Specific Peptidase 9, X-Linked in Oral Squamous Cell Carcinoma", Cancer Med., vol. 7https://doi.org/10.1002/cam4.1675, 4004-4008, 2018.
Murtaza, M., et al., "La FAM Fatale: USP9X in Development and Disease", Cell. Mol. Life Sci., vol. 72DOI: 10.1007/s00018-015-1851-0, 2075-2089, 2015.
Peddaboina, C., et al., "The Downregulation of Mcl-1 via USP9X Inhibition Sensitizes Solid Tumors to Bcl-xl Inhibition", BMC Cancer, 12:541, 1-12, 2012.

* cited by examiner

*Primary Examiner* — Bong-Sook Baek
(74) *Attorney, Agent, or Firm* — Elmore Patent Law Group, P.C.; Carolyn S. Elmore; Jia Kang

(57) ABSTRACT

The invention relates to compounds that inhibit DUBs, particularly USP9X. The invention also includes methods of inhibiting DUBs, including USP9X, and methods of treating cancers.

7 Claims, 10 Drawing Sheets

Lane Sample
1    Vehicle
2    CHX
3    10 µM Compound 5A
4    10 µM MG132
5    10 µM Compound 5A+10 µM MG132
6    1 µM Compound 5A+10 µM MG132
7    Vehicle

USP9X INHIBITORS

RELATED APPLICATIONS

This application is a continuation-in-part of U.S. application Ser. No. 18/095,161, filed Jan. 10, 2023, which is a continuation-in-part of U.S. application Ser. No. 17/988,230 filed Nov. 16, 2022, now U.S. Pat. No. 11,691,945, issued Jul. 4, 2023, which claims the benefit of U.S. Provisional Application No. 63/279,783, filed on Nov. 16, 2021. The entire teachings of the above applications are incorporated herein by reference.

BACKGROUND

Ubiquitination is a covalent post-translational modification of cellular proteins involving a complex enzymatic cascade. Emerging evidence suggests that many enzymes of the ubiquitination cascade are differentially expressed or activated in several diseases and may therefore be appropriate therapeutic targets.

Protein ubiquitination is a dynamic two-way process that can be reversed or regulated by deubiquitinating (deubiquitinase, DUB) enzymes. The human genome codes for nearly 100 proteins with putative DUB activity which can be broadly divided into two main sub-groups: ubiquitin C-terminal hydrolase (UCH) and the ubiquitin-specific proteases (USP). USPs comprise the largest subclass of DUBs in humans, while only 4 known UCH DUBs have been described. DUBs primarily serve to counterbalance ubiquitin-protein conjugation and also facilitate the cleavage of ubiquitin from its precursors and unanchored polyubiquitin chains. Thus, DUBs regulate and maintain the homeostasis of free ubiquitin pools in the cell. Several DUBs have been reported to regulate deubiquitination of histones, DNA damage repair, cellular proliferation (USP2) and cytokine signaling (DUB-A). DUBs such as USP14, Uch37 and RPN11 have been shown to associate with the regulatory sub-unit of the proteasome (19S) and edit polyubiquitin chains on proteasome substrates.

SUMMARY

The invention relates to the discovery of compounds that inhibit DUBs, particularly USP9X. Inhibition of DUBs, particularly USP9X, induces the targeted degradation of the substrates of the deubiquitylase. These substrates include Mcl-1, erbB2, beta-catenin and aldehyde dehydrogenase 1A3. The invention also includes methods of inhibiting DUBs, including USP9X. For example, the invention includes methods of treating, inhibiting or suppressing cancer, such as myeloma, lung cancer (e.g., non-small cell lung cancer), colon cancer, central nervous system (CNS) cancer, melanoma, ovarian cancer, renal cancer, prostate cancer, breast cancer (such as a triple negative breast cancer), pancreatic cancer, a virus-induced cancer, a Kaposi's sarcoma, a nasopharyngeal carcinoma (EBV), leukemia, a chronic myelogenous leukemia (CML), lymphoma, acute lymphocytic leukemia, a chronic lymphocytic leukemia, an acute myelogenous leukemia, a B-cell lymphoma, a mantle cell lymphoma, a multiple myeloma, a plasma cell dyscrasia, a myeloproliferative disorder, or a glioblastoma. In a preferable embodiment, provided is a method of treating, inhibiting or suppressing breast cancer or pancreatic cancer, more preferably, pancreatic cancer.

The invention also includes methods of inducing degradation of a USP9X substrate in a cell, such as Mcl-1 or erbB-2. For example, the invention includes methods of treating a condition in a subject wherein the condition is associated with a pathologic cell that expresses Mcl-1, comprising administrating to the subject an effective amount of the compound. Preferably, the condition is a cancer. In some embodiments, the degradation level of the USP9X substrate, such as Mcl-1, may be controlled, slowed down, or terminated by co-treating the cell with a proteasome inhibitor, such as Velcade.

Mcl-1 may serve as an anti-apoptotic factor that confers resistance, e.g., for a Bcl-2 family protein, to chemotherapy. The invention also includes methods of enhancing potency of a Bcl-2 family inhibitor in a cell expressing Mcl-1 and at least one other anti-apoptotic Bcl-2 family protein (such Bcl-2, Bcl-xL, or both), comprising co-treating the cell with the compound and the Bcl-2 family inhibitor. Preferably, the Bcl-2 family inhibitor is a BH3 mimetic such as Navitoclax or Venetoclax. The invention also includes methods of treating a condition in a subject wherein the condition is associated with a pathologic cell that expresses Mcl-1 and at least one other anti-apoptotic Bcl-2 family protein, comprising co-administrating to the subject an effective amount of a pharmaceutical composition of the compound and an effective amount of a pharmaceutical composition of a Bcl-2 family inhibitor. In some embodiments, the condition is a cancer, more preferably, acute myeloid leukemia (AML) or breast cancer.

In some embodiments, the compound can be incorporated into a PROTAC construct to target USP9X, leading to its ubiquitylation by an E3 ubiquitin ligase and consequently inducing the degradation of USP9X.

The invention also includes methods of treating inflammation, infection, such as a pathogenic infection, or a neurodegenerative disorder or symptoms of a neurodegenerative disorder, or a genetic disorder mediated to the DUB. Additionally, provided are methods of treating a condition arising from a pathogen infection comprising contacting the pathogen or a cell infected by the pathogen with the compound or composition as disclosed herein. The condition can be gastroenteritis, encephalitis, a respiratory tract infection, SARS, virus-induced cancer, rabies, a hemorrhagic fever, Rift valley fever, listeriosis, or toxoplasmosis. In some cases, the condition is meningitis, myocarditis, hepatitis, bacteremia, or a skin infection. The pathogen can be a virus, bacterium, fungus, or parasite. The virus can be a calicivirus, a norovirus, a sapovirus, a picornavirus, a Togavirus, a Bunyavirus, a Rhabdovirus, a herpes virus, an adenovirus, an arterivirus, a coronavirus, a flavivirus, a paramyxovirus, a papillomavirus, a virus encoding for an ovarian tumor (OTU)-like protease, a baculovirus, or a nairovirus. The virus can be a polyoma virus, a retrovirus or coronavirus. In various cases, the virus is selected from the group consisting of encephalomyocarditis virus (EMCV), Sindbis virus (SiNV), La Crosse virus (LaCV), Norwalk virus, Epstein-Barr (EBV), herpesvirus, Dengue virus, papillomavirus or coronavirus. The virus can be cytomegalovirus, BK virus, hepatitis C virus, or HIV. The bacterium can be *Chlamydia, Escherichia, Salmonella, Yersinia, Burkholderia, Haemophilus, Listeria*, or *Mycobacterium*. In some cases, the bacterium is *Staphylococcus aureus*. In various cases, the bacterium is methicillin-resistant Staph aureus (MRSA). The parasite or fungus can be *Plasmodium falciparum, Toxoplasma gondii, Entamoeba histolytica, Giardia lamblia, Trypanosoma brucei, Trypanosoma cruzi, Cestoda, Clonorchis, Opisthorchis, Strongylocides, Candida, Aspergillus*, or *Cryptococcus*.

The invention also includes methods of treating developmental disorders, such as intellectual disability, epilepsy, autism and developmental delay, and neurodegeneration, including Parkinson's and Alzheimer's disease, as well as autoimmune diseases and inflammation.

Thus, provided herein area compound represented by Formula (I):

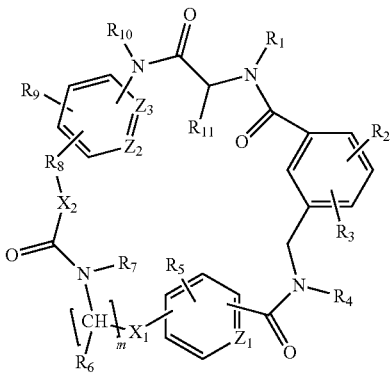

(I)

or optionally by a formula with a linear backbone structure obtained by breaking a carbon-carbon or carbon-nitrogen single bond on the cyclic backbone of Formula (I) at any site, and pharmaceutically acceptable salts thereof, wherein $R_1$ and $R_{10}$ are each independently selected from H, $^2$H, and substituted or unsubstituted alkyl;

$R_2$, $R_3$, $R_4$, $R_6$, and $R_7$ are each independently selected from H, $^2$H, halogen, substituted or unsubstituted alkyl, and substituted or unsubstituted alkoxy; and optionally, $R_3$ and $R_4$ together form a substituted or unsubstituted 5- or 6-membered heterocyclic ring;

$R_5$ and $R_9$ are each independently selected from H, $^2$H, substituted or unsubstituted alkyl, substituted or unsubstituted alkoxy, and one or more aryl substituents, such as halogen;

$R_8$ is absent, or substituted or unsubstituted 1- to 4-carbon alkylene;

$R_1$ is a hydrophobic alkyl selected from substituted or unsubstituted alkyl, and substituted or unsubstituted cycloalkyl;

$Z_1$, $Z_2$, and $Z_3$ are each independently selected from CH and N;

$X_1$ is selected from —O—, —S—, —NH—, —CH$_2$—;

$X_2$ is absent, or selected from -L-NR$_A$—, -L-NR$_A$C(O)—, -L-C(O)—, -L-OC(O)—, -L-C(O)O—, -L-CH(COOR$_A$)—, -L-C(O)NR$_A$-L-, -L-C(O)NR$_A$C(O)—, wherein R$_A$ is selected from H, $^2$H, substituted or unsubstituted alkyl; and optionally, R$_A$, R$_8$, and X$_2$ together with the aryl to which R$_8$ is attached to form a substituted or unsubstituted 5- or 6-membered heterocyclic ring;

L is a linker group —(CH$_2$)$_n$CR$_B$R$_C$(CH$_2$)$_n$—, wherein R$_B$ and R$_C$ are each independently selected from H, $^2$H, substituted or unsubstituted alkyl; or R$_B$ and R$_C$ together with the carbon to which they are attached form a substituted or unsubstituted C$_3$-C$_6$ cycloalkyl, or a substituted or unsubstituted 3- to 6-membered heterocyclic ring; and wherein each n is independently 0, 1, or 2;

and m=0, 1, 2, 3, or 4.

In preferable embodiments, $R_1$ and $R_6$ are H; $R_2$, $R_3$, $R_4$, and $R_5$ are each independently selected from H, F, Cl, —CH$_3$, and —OCH$_3$; $R_7$ is H or methyl (more preferably methyl); $R_{11}$ is selected from —CH$_2$C(CH$_3$)$_3$, —CH$_2$CH(CH$_3$)$_2$, —CH$_2$-cyclo-C$_3$H$_5$, and —CH$_2$-cyclo-C$_4$H$_7$; and X is —O— or —CH$_2$—.

In preferable embodiments, L is —CH$_2$CH$_2$CH$_2$— or —CH$_2$C(CH$_3$)$_2$CH$_2$—, and more preferably, —CH$_2$C(CH$_3$)$_2$CH$_2$—.

In preferable embodiments, X$_2$ is —CH$_2$C(CH$_3$)$_2$CH$_2$C(O)N(CH$_3$)—.

In some embodiments, R$_8$ is a) a substituted 2-carbon alkene, wherein the substituent is selected from halogen such as F or Cl, oxo, —COOH, —CONH$_2$, —CONH—C$_2$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, and —CONH—C$_2$-C$_8$-alkoxy; or b) —CH$_2$CH$_2$—. Preferably, R$_8$ is selected from —CH(COOH)CH$_2$—, —CH[C(O)NHCH$_2$CH$_2$OCH$_3$]CH$_2$—, and —CH$_2$CH$_2$—; and more preferably, is —CH$_2$CH$_2$—.

In some embodiments, each of $Z_1$, $Z_2$, and $Z_3$ is CH; one of $Z_1$, $Z_2$, and $Z_3$ can be N; or two of $Z_1$, $Z_2$, and $Z_3$ can be N. Preferably, $Z_1$ is N, $Z_1$ and $Z_2$ are CH.

In preferable embodiments, m=1, 2, or 3.

In preferable embodiments, provided herein are a compound represented by Formula (I) and pharmaceutically acceptable salts thereof.

In a preferred embodiment, the compound can be of Formula (II) or (III):

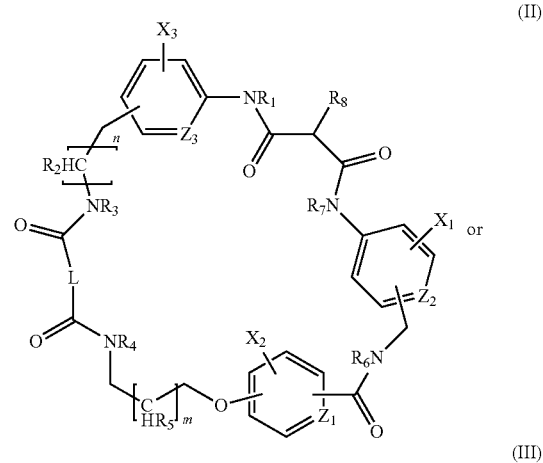

(II)

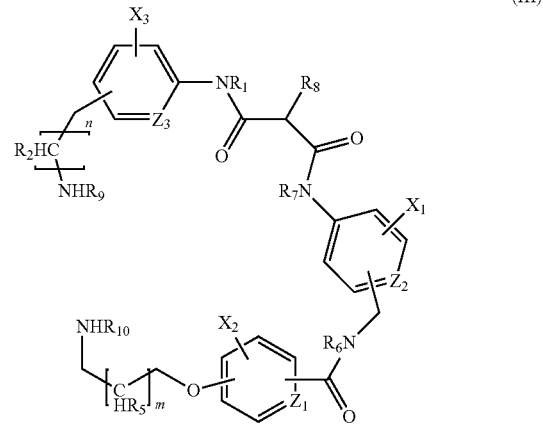

(III)

and pharmaceutically acceptable salts thereof,
wherein $R_1$, $R_2$, $R_3$, $R_4$, $R_5$, $R_6$, $R_7$, and $R_8$ are independently hydrogen or a substituted or unsubstituted alkyl,
$R_9$, and $R_{10}$ are independently hydrogen, substituted or unsubstituted alkyl, or substituted or unsubstituted acyl,
L is a linker group, such as a substituted or unsubstituted, saturated or unsaturated 1 to 10 carbon alkylene,
$Z_1$, $Z_2$, and $Z_3$ are independently selected from N or CH,
$X_1$, $X_2$, $X_3$ are independently H or one or more aryl substituents, such as a halogen, e.g., fluorine,
n and m are independently 0 or an integer, such as 1, 2, 3, 4, or 5.

Preferably, $R_1$ is hydrogen, $R_2$ is hydrogen, $R_3$ is hydrogen or methyl (more preferably methyl), $R_4$ is hydrogen or methyl (more preferably methyl), $R_5$ is hydrogen, $R_6$ is hydrogen or methyl (more preferably hydrogen), and $R_7$ is hydrogen or methyl (more preferably hydrogen).

$R_8$ is preferably an alkyl group, and more preferably a branched alkyl, such as a 4, 5, or 6 carbon alkyl. —$CH_2C(CH_3)_3$ is preferred. Where one or more of $R_2$, $R_5$, and $R_8$ are a substituted or unsubstituted alkyl, a chiral center is formed. The invention contemplates racemates and purified or isolated stereoisomers, enantiomers and diastereomers. Preferably, the linker L is —$(CH_2)_2C(CH_3)_2(CH_2)_2$—. Alternatively, the linker can include one or more heteroatoms, such as an oxy, amine, amido or ester. For example, the linker can be —$(CH_2)_2O(CH_2)_2$—, —$(CH_2)_2NH(CH_2)_2$—, —$(CH_2)_2CONH\ (CH_2)_2$—, or —$(CH_2)_2CO_2(CH_2)_2$—. The linker can also be unsaturated or aromatic, such as a —$(CH_2)_2CH=CH\ (CH_2)_2$— or a 1,4-phenylene.

Preferably, each of $Z_1$, $Z_2$, and $Z_3$ are CH. Preferably, one of $Z_1$, $Z_2$, and $Z_3$ can be N. Preferably, $Z_1$ and $Z_2$ are CH and $Z_3$ is CH or N.

In some embodiments, provided is also a compound of Formula (IV), or any one of Formula (IVa)-(IVf).

For example,

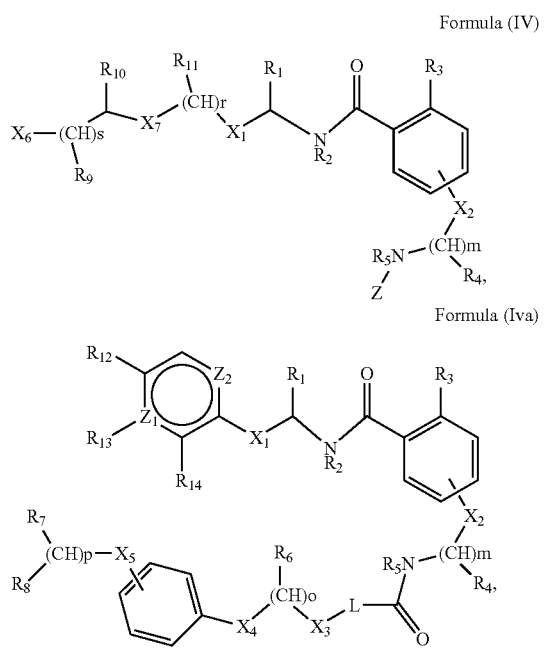

Formula (IV)

Formula (Iva)

Wherein all the variables are as defined herein.

In some embodiments, provided is a compound selected from those in Table 1. In additional embodiments, provided is a compound selected from those in Table 7. Also disclosed are pharmaceutical compositions comprising a compound as described herein and a pharmaceutically acceptable excipient. The pharmaceutical composition can be formulated for oral, topical, intravenous, subcutaneous, intramuscular, intrathecal, ophthalmic, or inhalational route of administration.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1A:
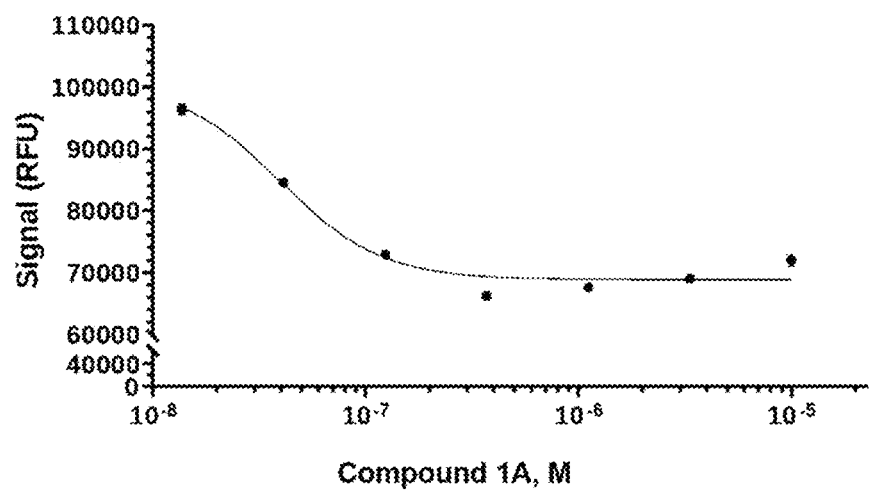
FIG. 1A is a graph showing a curve of fluorescence (RFU) vs. the concentration of Compound 1A. The effect of Compound 1A was evaluated in an assay measuring the ability of USP9X to catalyze the hydrolysis of the amide bond between the C terminal carboxylate of ubiquitin and rhodamine110 of the fluorogenic substrate ubiquitin-rhodamine 110.
Figure 1B:
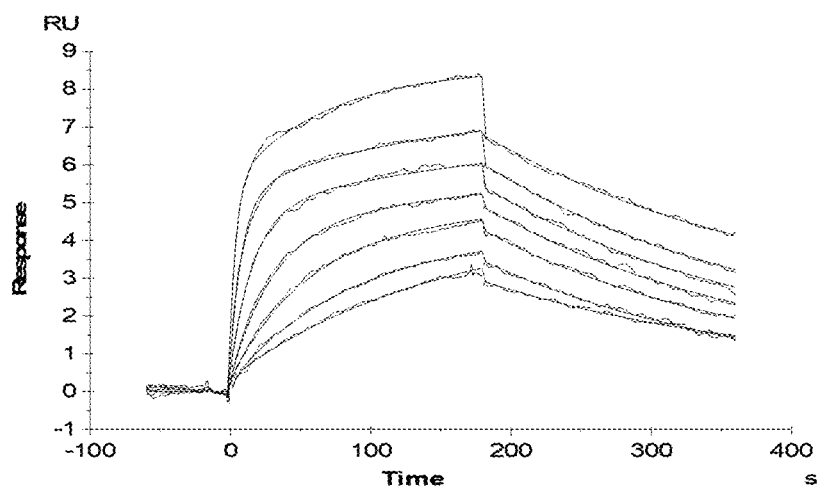
FIG. 1B is a graph depicting relative response vs. time curves for Compound 2A binding to USP9X as determined by the BIACORE™ assay at Compound 2A concentration ranging from $0.3 \times 10^{-6}$ mol/l to $20 \times 10^{-6}$ mol/l described in Example 2.
Figure 1C:
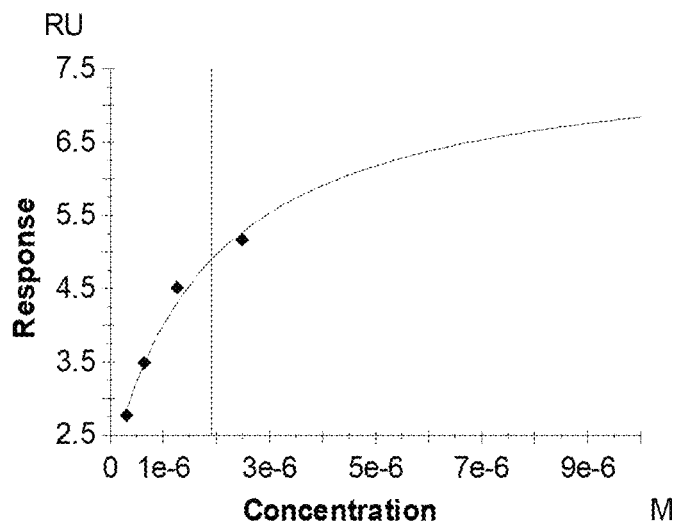
FIG. 1C is a graph depicting affinity determination of Compound 2A binding to USP9X as determined by the BIACORE™ assay described in Example 2.
Figure 1D:
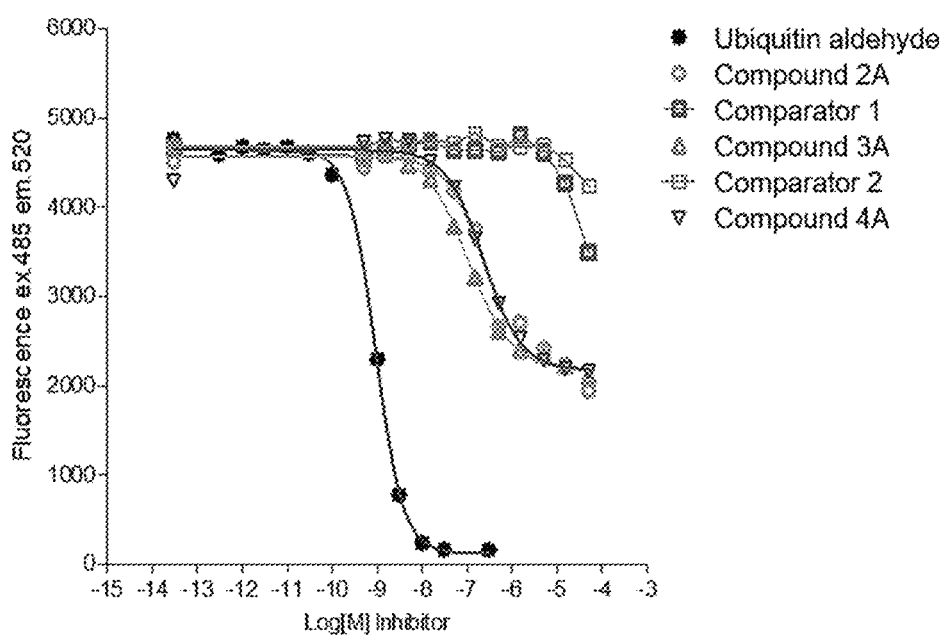
FIG. 1D is a graph depicting the effects of compounds Compound 2A, Comparator 1, Compound 3A, Comparator 2, and Compound 4A on the enzyme activity of USP9X on the fluorogenic substrate ubiquitin-rhodamine110 (BPS-Biosciences). The fluorescent signals generated by the USP9X mediated generation of the fluorescent product were monitored over time at the presence of these compounds at varying concentrations and at the presence of ubiquitin aldehyde as a positive control, respectively.

The ubiquitin-specific protease 9X (USP9X/FAM) is a substrate-specific DUB. USP9X plays a significant role in cancer, both as an oncogene or tumor suppressor, developmental disorders, such as intellectual disability, epilepsy, autism and developmental delay, neurodegeneration, including Parkinson's and Alzheimer's disease, and inflammation such as autoimmune diseases. Murtaza et al., Cell. Mol. Life Sci. (2015) 72:2075-2089, US Patent Publication 2017/0204055 (Brandeis University) and US Patent Publication 2016/0237082 (University of Michigan), which are incorporated herein by reference.

The Compound of the Invention

Disclosed herein are compounds and methods of inhibiting a DUB, methods of inhibiting DUB catalytic activity, methods of inhibiting Usp9x, methods of inhibiting survival or proliferation of a cell, such as a cancer cell, methods of treating a neurodegenerative disorder, methods of treating one or more symptoms of a neurodegenerative disorder, methods of treating one or more symptoms of a genetic disorder, and methods of inhibiting or preventing a pathogenic infection. In some embodiments, "the USP9X inhibitor" and "the compound" as used herein are interchangeable. In some embodiments, "cancer cell" and "tumor cell" as used herein are interchangeable. The compounds of the invention include a compound of Formula (I), or optionally a formula with a linear backbone structure obtained by breaking a carbon-carbon or carbon-nitrogen single bond on the cyclic backbone of Formula (I) at any site, and salts thereof:

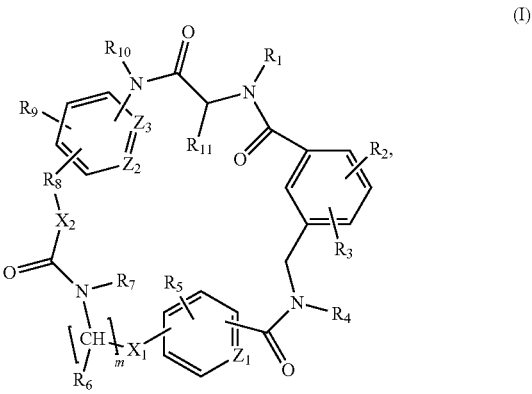

(I)

The variables in Formula (I) (including $R_1$, $R_2$, $R_3$, $R_4$, $R_5$, $R_6$, $R_7$, $R_8$, $R_9$, $R_{10}$, $R_{11}$, $Z_1$, $Z_2$, $Z_3$, $X_1$, $X_2$, m, and L) are as defined above.

Preferred alkyls include lower alkyls, such as methyl, ethyl, n-propyl, i-propyl, n-butyl, sec-butyl, i-butyl, tert-butyl, n-pentyl, s-pentyl, i-pentyl, or t-amyl.

The invention contemplates racemates and purified or isolated stereoisomers, enantiomers and diastereomers.

In some embodiments, the compounds of the invention include a compound of Formula (II) or (III), and salts thereof:

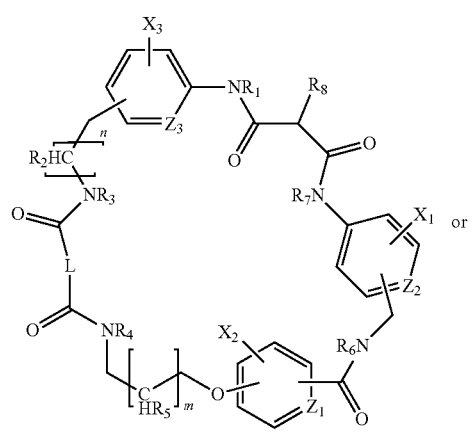

(II)

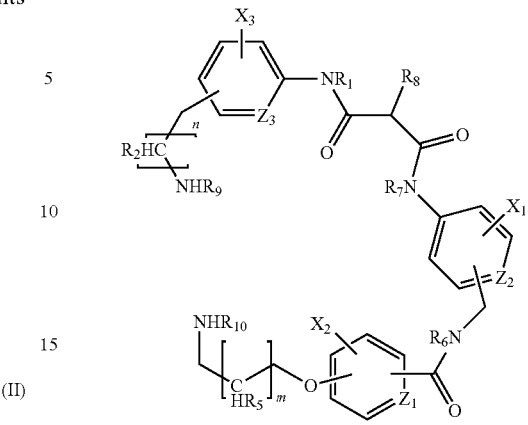

(III)

and pharmaceutically acceptable salts thereof.

The variables in Formula (II) and (III) (including $R_1$, $R_2$, $R_3$, $R_4$, $R_5$, $R_6$, $R_7$, $R_8$, $R_9$, $R_{10}$, $Z_1$, $Z_2$, $Z_3$, $X_1$, $X_2$, $X_3$, L, m, and n) are as defined in Summary. Preferred alkyls include lower alkyls, such as methyl, ethyl, n-propyl, i-propyl, n-butyl, sec-butyl, i-butyl, tert-butyl, n-pentyl, s-pentyl, i-pentyl, or t-amyl. Preferred acyls include alkylcarbonyls, such as acetyl or t-boc. The invention contemplates racemates and purified or isolated stereoisomers, enantiomers and diastereomers.

The following Table 1 provides additional representative examples of the invention.

TABLE 1

| Compound # | Structure |
|---|---|
| 1A | 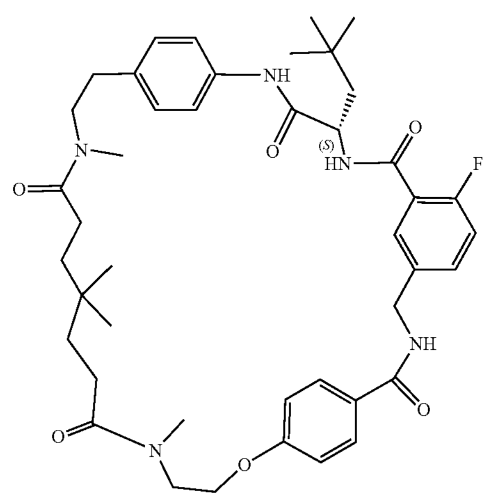 |

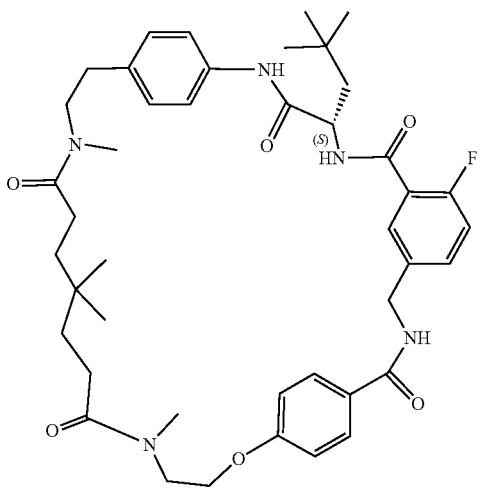

TABLE 1-continued

Exemplary Compounds

| Compound # | Structure |
| --- | --- |
| 2A | 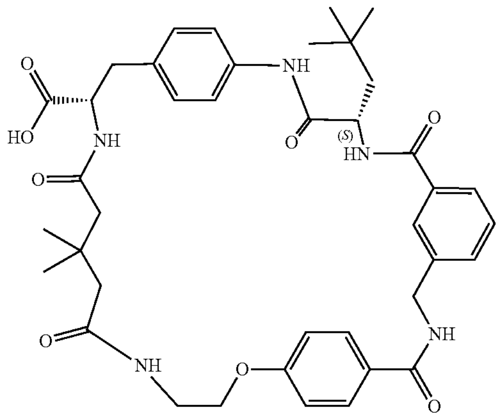 |
| 3A | 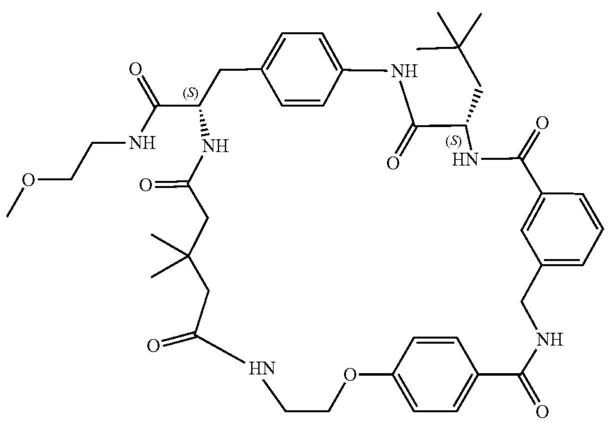 |
| 4A | 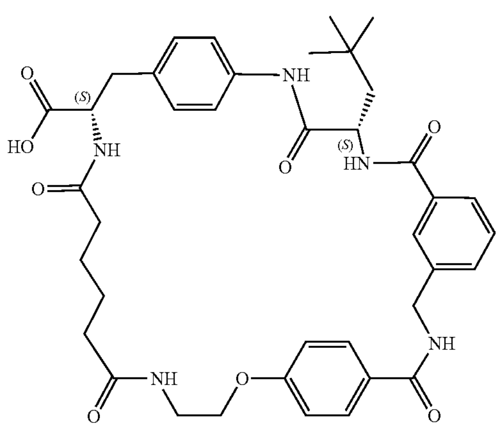 |

TABLE 1-continued

Exemplary Compounds

| Compound # | Structure |
|---|---|
| 5A | 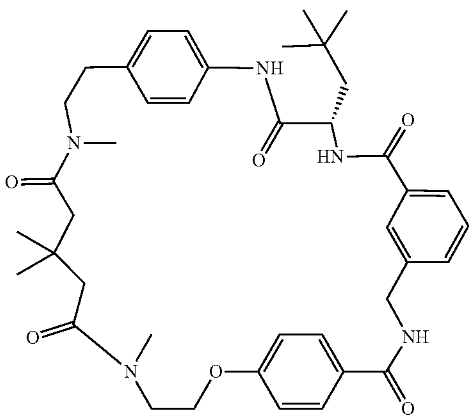 [SMILES: CN1CCOc2ccc(cc2)C(=O)NCc2cccc(c2)C(=O)N[C@@H](CC(C)(C)C)C(=O)Nc2ccc(cc2)CCN(C)C(=O)CC(C)(C)CC1=O] |
| 6A | 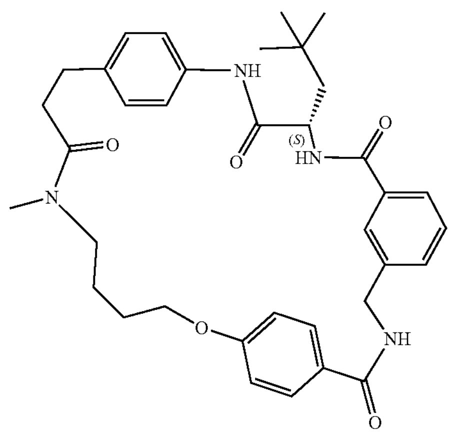 |
| 7A | 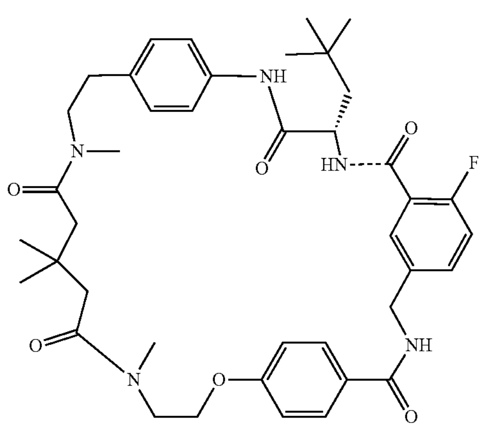 |

TABLE 1-continued
Exemplary Compounds
| Compound # | Structure |
|---|---|
| 8A | 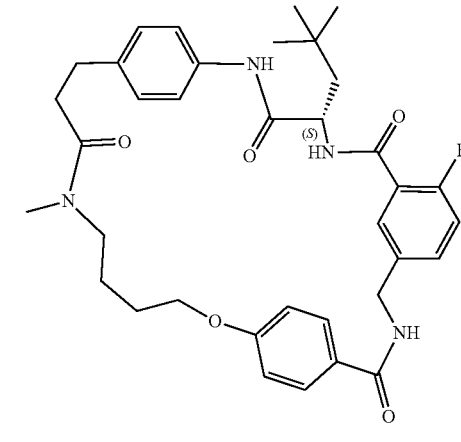 |
| 9A | 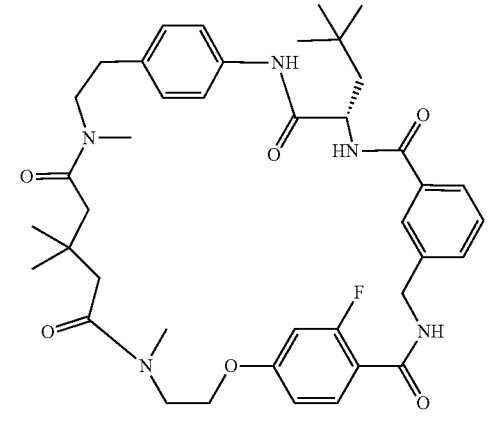 [SMILES: CN1CCOc2ccc(c(F)c2)C(=O)NCc2cccc(c2)C(=O)N[C@@H](CC(C)(C)C)C(=O)Nc2ccc(cc2)CCN(C)C(=O)CC(C)(C)CC1=O] |
| 10A | 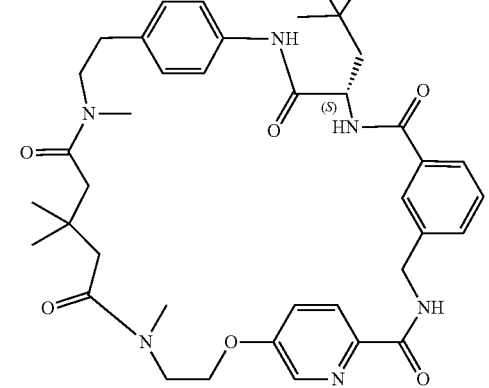 |

TABLE 1-continued

Exemplary Compounds

| Compound # | Structure |
|---|---|
| 11A | 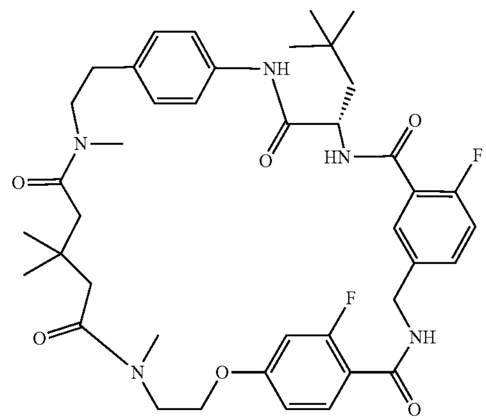 [SMILES: CN1CCOc2ccc(c(F)c2)C(=O)NCc2ccc(F)c(c2)C(=O)N[C@@H](CC(C)(C)C)C(=O)Nc2ccc(cc2)CCN(C)C(=O)CC(C)(C)CC1=O] |
| 12A | 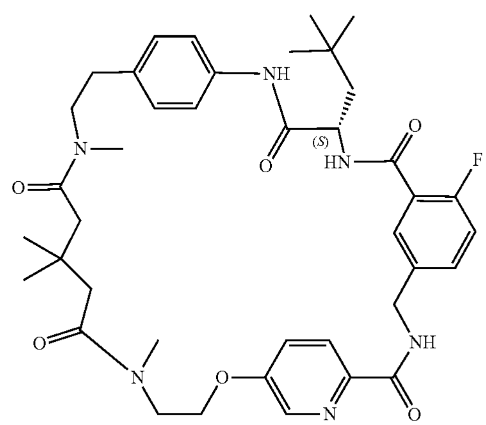 |
| 13A | 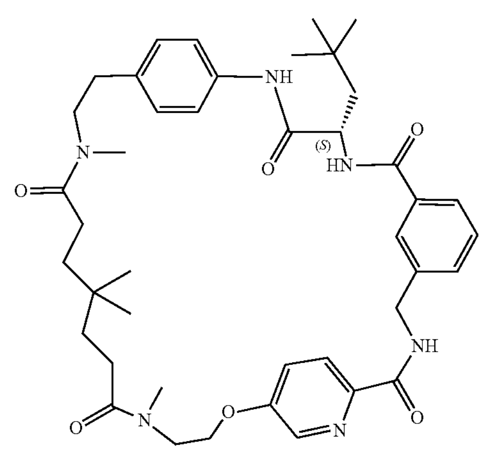 |

In some embodiments, the compounds of the invention include a compound of Formula (IV), and salts thereof:

Formula (IV)

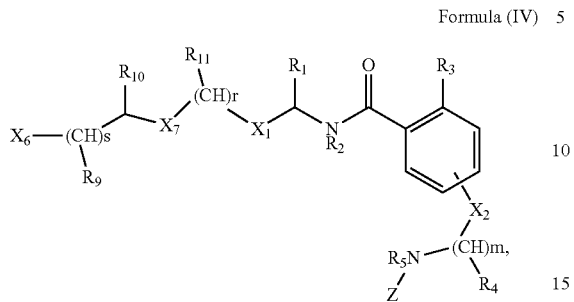

and Z is H, a substituted or unsubstituted alkyl (such as a $C_{1-6}$ alkyl), —C(O)CH$_3$, or Z is:

Formula (Z)

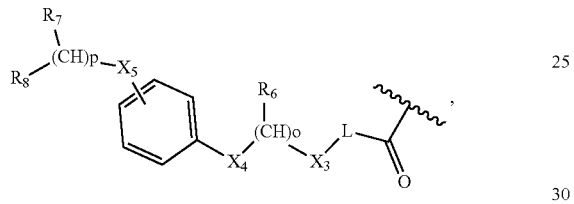

and the generic structure is represented the formula as below:

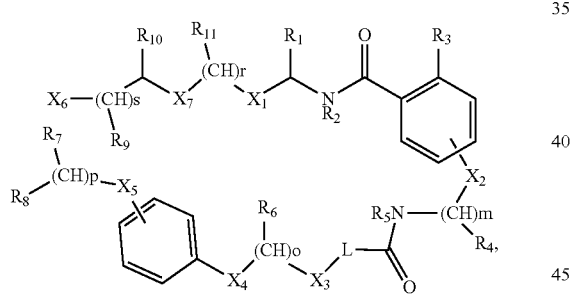

Wherein m, o, p, s, and r are each independently selected from 0, 1, 2, 3, 4, or 5.

$R_1$, $R_4$, $R_6$, $R_7$, $R_9$, $R_{10}$ and $R_{11}$ are each independently selected from H, D, halogen, substituted or unsubstituted alkyl, substituted or unsubstituted aryl, substituted or unsubstituted heteroaryl, substituted or unsubstituted cycloalkyl, substituted or unsubstituted heterocycloalkyl; alternatively, when r is 1, $R_{10}$ and Ru together with the carbons to which they are attached form a substituted or unsubstituted aryl, substituted or unsubstituted heteroaryl, substituted or unsubstituted cycloalkyl, substituted or unsubstituted heterocycloalkyl;

$R_2$ and $R_5$ are each independently selected from H, $^2$H, and substituted or unsubstituted alkyl; alternatively, $R_1$ and $R_2$ together with the carbon and nitrogen to which they are respectively attached form a substituted or unsubstituted heteroaryl, or a substituted or unsubstituted heterocycloalkyl; alternatively, when m is 1, $R_4$ and $R_5$ together with the carbon and nitrogen to which they are respectively attached form a substituted or unsubstituted heteroaryl, or a substituted or unsubstituted heterocycloalkyl;

$R_3$ is selected from H, D, halogen, substituted or unsubstituted alkyl;

$R_8$ is selected from H, D, halogen, substituted or unsubstituted alkyl, substituted or unsubstituted aryl, substituted or unsubstituted heteroaryl, substituted or unsubstituted cycloalkyl, substituted or unsubstituted heterocycloalkyl, —OR$^A$, —CN, —NR$^B$R$^C$, —NR$^D$C(O)R$^E$, —CO$_2$R$^F$, and —C(O)NR$^G$R$^H$, wherein each of $R_A$, R$^B$, R$^C$, R$^D$, R$^E$, R$^F$, R$^G$, and R$^H$ is independently selected from H, D, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocycloalkyl; or R$^B$ and R$^C$ or R$^G$ and R$^H$ can be taken together with the nitrogen to which they are attached to form a substituted or unsubstituted 5, 6, 7, or 8 membered ring; alternatively, wherein when p is 1, $R_7$ and $R_8$ together with the carbons to which they are attached form a substituted or unsubstituted aryl, substituted or unsubstituted heteroaryl, substituted or unsubstituted cycloalkyl, substituted or unsubstituted heterocycloalkyl;

$X_1$, $X_2$, $X_3$, $X_4$, $X_5$, and $X_7$ are each independently selected from absent, substituted or unsubstituted alkylene, substituted or unsubstituted aryl, substituted or unsubstituted heteroaryl, substituted or unsubstituted cycloalkyl, substituted or unsubstituted heterocycloalkyl, —NR$^I$C(O)—, —C(O)NR$^J$—, —O—, —OC(O)—, —C(O)O—, —NR$^K$C(O)NR$^K$—, —C(R$^L$)=C(R$^M$)—, —NR$^L$—CR$^M$R$^N$—, —CR$^M$R$^N$—NR$^L$—, wherein each of R$^I$, R$^J$, R$^K$, R$^L$, and R$^M$ is independently selected from H, D, substituted or unsubstituted alkyl; alternatively, when $X_7$ is —C(R$^L$)=C(R$^M$)— or —NR$^L$—CR$^M$R$^N$—, R$^L$ and $X_6$ or $R_9$ together with the atoms to which they are respectively attached form a substituted or unsubstituted aryl, substituted or unsubstituted heteroaryl, substituted or unsubstituted cycloalkyl, substituted or unsubstituted heterocycloalkyl, wherein the R$^N$ in —NR$^L$—CR$^M$R$^N$— can be absent and the carbon atom is covalently bound to the moiety on the right via a double bond; alternatively, when r is 1, $X_7$ is —C(R$^L$)=C(R$^M$)—, —NR$^L$—CR$^M$R$^N$—, $R_{10}$, $R_{11}$, $X_7$, R$^L$, and $X_6$ or $R_9$ together with the atoms to which they are respectively attached form a substituted or unsubstituted bicyclic fused ring system that contains zero, one or more heteroatoms such as N, O, or S.

L is absent or a linker group —(CH$_2$)$_n$CR$^O$R$^P$(CH$_2$)$_n$—, wherein R$^O$ and R$^P$ are each independently selected from H, $^2$H, substituted or unsubstituted alkyl; or R$^O$ and R$^P$ together with the carbon to which they are attached form a substituted or unsubstituted $C_3$-$C_6$ cycloalkyl, or a substituted or unsubstituted 3- to 6-membered heterocyclic ring; and wherein each n is independently 0, 1, or 2. Preferably, L is —CH$_2$C(CH$_3$)$_2$CH$_2$—; and $X_6$ is selected from H, D, substituted or unsubstituted alkyl, substituted or unsubstituted aryl, substituted or unsubstituted heteroaryl, substituted or unsubstituted cycloalkyl, substituted or unsubstituted heterocycloalkyl, —OR$^A$, —CN, —NR$^B$R$^C$, —NR$^D$C(O)R$^E$, —CO$_2$R$^F$, —C(O)NR$^G$R$^H$, or —(CHR$_{18}$)$_q$-X$_8$-L-R$_{19}$;

$X_8$ is absent, —CONH—, —NHC(O)—, —N(CH$_3$)—, —OC(O)—, —C(O)O—, —O—, or —NHC(O)NH—;

q is 0, 1, 2, 3, or 4;

R$_{18}$ is selected from H, halogen, a substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocycloalkyl, —OR$^A$, —CN, —NR$^B$R$^C$, —NR$^D$C(O)R$^E$, —CO$_2$R$^F$, and —C(O)NR$^G$R$^H$;

R$_{19}$ is selected from H, halogen, a substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, substituted or unsubstituted heterocycloalkyl, —OR$^A$, —CN, —NR$^B$R$^C$, —NR$^D$C(O)R$^E$, —CO$_2$R$^F$, —C(O)NR$^G$R$^H$, —C$_{1-6}$ alkyl-NR$^B$R$^C$, —C$_{1-6}$ alkyl-NR$^D$C(O)R$^E$, —C$_{1-6}$ alkyl-CO$_2$R$^F$, —C$_{1-6}$ alkyl-C(O)NR$^G$R$^H$; or R$_1$ is:

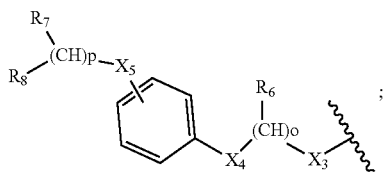

Alternatively, when L is absent, R$_{18}$/X$_8$/R$_{19}$ together form a substituted or unsubstituted aryl, substituted or unsubstituted heteroaryl, substituted or unsubstituted cycloalkyl, and substituted or unsubstituted heterocycloalkyl.

In some preferred embodiments, R$_1$ is H, —CH$_3$, —CH$_2$CH$_3$, —CH$_2$CH$_2$CH$_3$, —CH$_2$CH(CH$_3$)$_2$, —CH$_2$C(CH$_3$)$_3$, —OCH$_3$, —OCH$_2$CH$_3$, —CH$_2$—OCH$_3$, —OCH$_2$CH$_2$CH$_3$, —CH$_2$CH$_2$—OCH$_3$, —CH$_2$—OCH(CH$_3$)$_2$, —CH$_2$—OC(CH$_3$)$_3$. More preferably, R$_1$ is H, —CH$_3$, —CH$_2$CH(CH$_3$)$_2$, or —CH$_2$C(CH$_3$)$_3$. Most preferably, R$_1$ is —CH$_2$C(CH$_3$)$_3$.

In some preferred embodiments, R$_2$ is H.

In additional preferred embodiments, R$_1$ and R$_2$ together with the carbon and nitrogen to which they are respectively attached form a substituted or unsubstituted 5- or 6-membered heteroaryl, or a substituted or unsubstituted 5- or 6-membered heterocycloalkyl, including but not limited to:

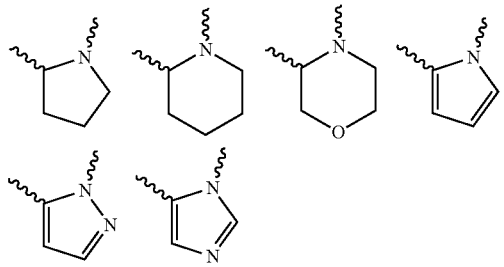

In some preferred embodiments, R$_3$ is H, halogen (F, Cl, Br, or I), —CH$_3$, —OCH$_3$, —CN. Preferably, R$_3$ is H or F. More preferably, R$_3$ is H.

In some preferred embodiments, X$_2$ is absent and the —NR$_2$C(O)-phenyl substituent attached to X$_2$ is a meta-substituent; or X$_2$ is —O— and is a para-substituent to the —NR$_2$C(O)— phenyl group.

In some preferred embodiments, m is 1 or 2.

In some preferred embodiments, R$_4$ is H.
In some preferred embodiments, R$_5$ is H or —CH$_3$.
In some preferred embodiments, Z and R$_8$ are both H.
In some preferred embodiments, o is 0 or 2. Preferably, o is 2.
In some preferred embodiments, R$_6$ is H.
In some preferred embodiments, each of L, X$_3$ and X$_4$ is absent.

In some more preferred embodiments, X$_2$ is absent, m is 1, R$_4$ and R$_5$ are both H, each of L, X$_3$ and X$_4$ is absent.

As a nonlimiting example, the moiety, —X$_2$—(CHIR$_4$)$_m$—NR$_5$C(O)-L-X$_3$—(CHR$_6$)o-X$_4$—, is —CH$_2$NHC(O)—.

As another nonlimiting example, the moiety, —X$_2$—(CHIR$_4$)$_m$—NR$_5$C(O)-L-X$_3$—(CHIR$_6$)o-X$_4$—, is —O—(CH$_2$)$_2$—NHC(O)—CH$_2$C(CH$_3$)$_2$CH$_2$—CONH—(CH$_2$)$_2$—.

In some preferred embodiments, X$_5$ is absent, —O—, —NHCO—, or —C(O)NH—. Preferably, X$_5$ is —O— or —NHCO—.

In some preferred embodiments, p is 0, 1, or 2. Preferably, p is 1 or 2.

In some preferred embodiments, R$_7$ is H, —CH$_3$, —CH$_2$CH$_3$, —CH$_2$CH$_2$CH$_3$, —CH$_2$CH(CH$_3$)$_2$, —CH$_2$C(CH$_3$)$_3$. Preferably, R$_7$ is H, —CH$_3$, or —CH$_2$C(CH$_3$)$_3$.

In some preferred embodiments, R$_8$ is H, —NHCH$_3$, —N(CH$_3$)$_2$, —NHCOCH$_3$, or —NH$_2$.

In some more preferred embodiments, X$_5$ is —O—, p is 2, R$_7$ is H, and R$_8$ is —NHCH$_3$ or —N(CH$_3$)$_2$.

In some preferred embodiments, X$_1$ is —N(CH$_3$)C(O)—, —NHC(O)— or absent. Preferably, X$_1$ is —NHC(O)—.

In some preferred embodiments, r is 0, 1, or 2.

More preferably, r is 1, and R$_{10}$ and R$_{11}$ together with the carbons to which they are attached form a substituted or unsubstituted 5- or 6-membered aryl, substituted or unsubstituted 5- or 6-membered heteroaryl, substituted or unsubstituted 5- or 6-membered cycloalkyl, substituted or unsubstituted 5- or 6-membered heterocycloalkyl. Non-limiting examples of R$_{10}$/X$_7$/CHR$_{11}$ moiety include:

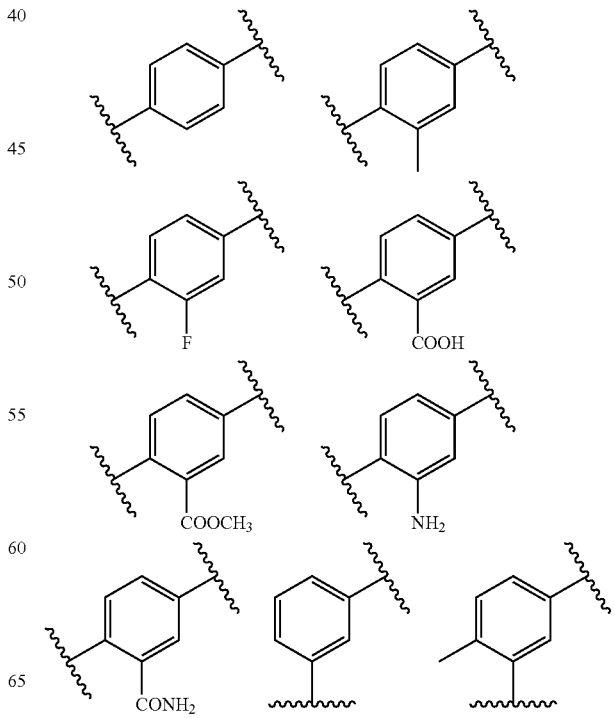

-continued

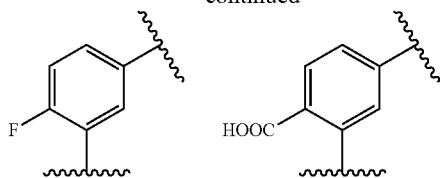

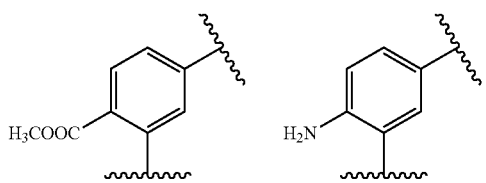

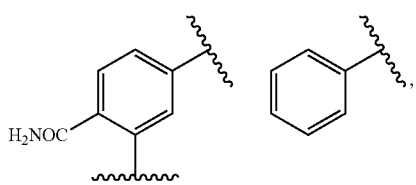

Wherein ⌇ on the right (or at the upper position) is connected to $X_1$ and ⌇ on the left (or at the lower position) is connected to —(CHR$_9$)s-X$_6$; and the single substituted phenyl ring is corresponding to s is 0 and $X_6$ is H.

In some preferred embodiments, $R_9$ is H or —CH$_2$C(CH$_3$)$_3$. Preferably, $R_9$ is H.

In some preferred embodiments, s is 0, 1, or 2. Preferably, s is 2.

In some preferred embodiments, $X_6$ is H, —OCH$_3$, —CF$_3$, —N(CH$_3$)$_2$, —NHC(O)CH$_3$, —COOH, —C(O)N(CH$_3$)$_2$, —C(O)NHCH$_3$, —NH$_2$, —NHC(O)CH$_2$C(CH$_3$)$_3$, pyrrolidine, pyrroline, pyrrole, pyrazolidine, imidazolidine, pyrazoline, imidazoline, pyrazole, or morpholine.

In additional embodiments, $X_6$ is —(CHR$_{18}$)$_q$—X$_8$-L-R$_{19}$. In some cases, q is 0, L is absent, thereby $X_6$ is —X$_8$-R$_{19}$, wherein $X_s$ is —CONH— and Rig is —CH[CH$_2$C(CH$_3$)$_3$]COOH, thereby $X_6$ is C(O)NHCH[CH$_2$C(CH$_3$)$_3$]COOH; $X_8$ is —CONH— and Rig is —CH[CH$_2$C(CH$_3$)$_3$]CONHCH$_3$, thereby $X_6$ is —C(O)NHCH[CH$_2$C(CH$_3$)$_3$]CONHCH$_3$. In some cases, q is 1, $R_{18}$ is H or —COO CH$_3$, $X_8$ is —NHCO—, L is —CH$_2$C(CH$_3$)$_2$CH$_2$—, $R_1$ is —COOH.

When r is 1, and $R_{10}$ and $R_{11}$ together with the carbons to which they are attached form a substituted phenyl, thereby

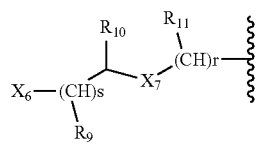

is phenyl-(CHR$_9$)s-X$_6$;

non-limiting examples of —(CHR$_9$)s-X$_6$ include: H, F, —CH$_3$, —OCH$_3$, —COOCH$_3$, —CONHCH$_3$, and any one of those groups presented in Table 5.

TABLE 5

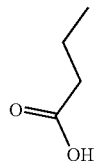

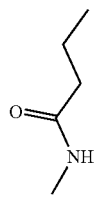

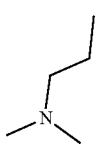

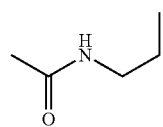

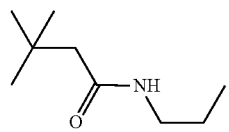

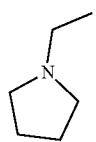

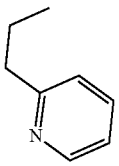

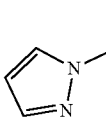

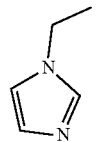

TABLE 5-continued

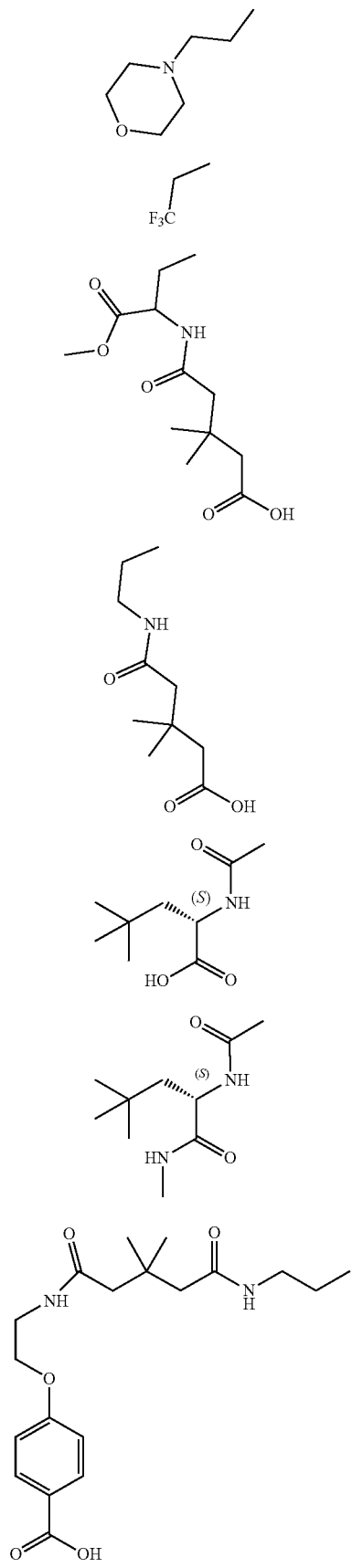

TABLE 5-continued

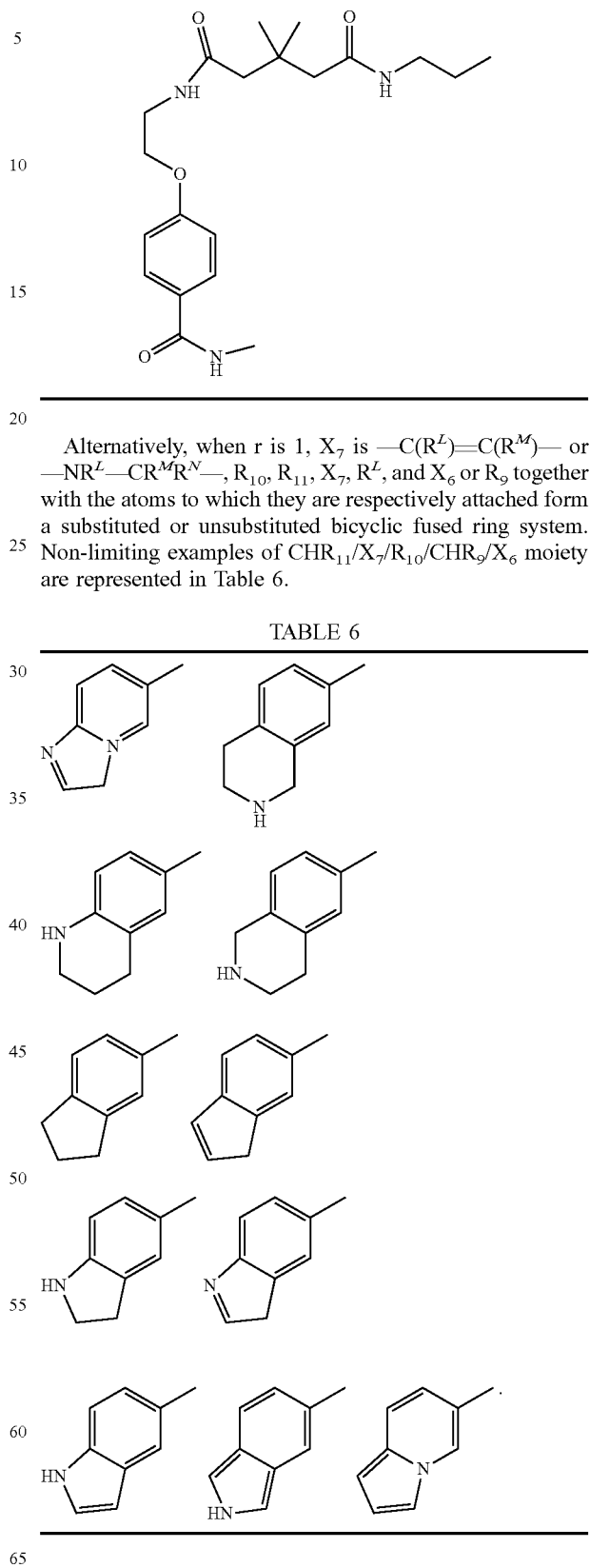

Alternatively, when r is 1, $X_7$ is —C($R^L$)=C($R^M$)— or —$NR^L$—$CR^MR^N$—, $R_{10}$, $R_{11}$, $X_7$, $R^L$, and $X_6$ or $R_9$ together with the atoms to which they are respectively attached form a substituted or unsubstituted bicyclic fused ring system. Non-limiting examples of $CHR_{11}/X_7/R_{10}/CHR_9/X_6$ moiety are represented in Table 6.

TABLE 6

In some cases, r is 0; $X_7$ is absent; s is 0, 1, 2, or 3; $R_9$ and $R_{10}$ are both H; and $X_6$ is —N(CH$_3$)$_2$, —NH$_2$, —NHCH$_3$, pyrrolidine, pyrroline, pyrrole, pyrazolidine, imidazolidine, pyrazoline, imidazoline, or pyrazole; preferably, $X_6$ is —N(CH$_3$)$_2$ or pyrrolidine.

In additional cases, r is 2; $X_7$ is —O—; s is 0, 1, 2, or 3; $R_9$, $R_{10}$, and $R_1$ are each H; and $X_6$ is —N(CH$_3$)$_2$, —NH$_2$, —NHCH$_3$, pyrrolidine, pyrroline, pyrrole, pyrazolidine, imidazolidine, pyrazoline, imidazoline, or pyrazole; preferably, $X_6$ is —N(CH$_3$)$_2$ or pyrrolidine.

In yet additional cases, r is 0; s is 1; $X_7$ is absent; $R_{10}$ is H; $X_6$ and $R_9$ together with the carbon to which they are attached form a substituted or unsubstituted phenyl, a substituted or unsubstituted pyridine, a substituted or unsubstituted pyridazine, a substituted or unsubstituted pyrimidine, or a substituted or unsubstituted pyrazine; preferably, a substituted or unsubstituted phenyl, or a substituted or unsubstituted pyridine.

In some cases, $R_5$ is H or —CH$_3$; Z is H, —CH$_3$, or —C(O)CH$_3$; $X_6$ is —CH($R_{18}$)—$X_8$-L-$R_{19}$; Rig is:

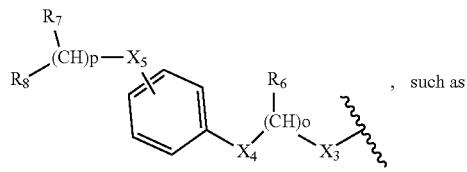

, such as

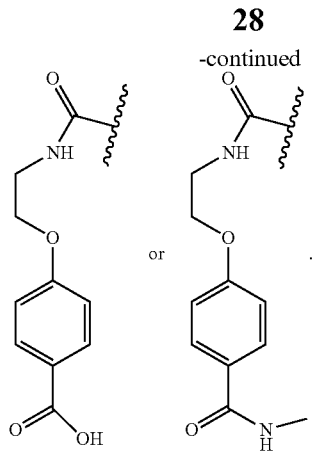

Nonlimiting exemplary compounds for Formula (IV) include any one of those compounds in Table 7.

TABLE 7

Exemplary compounds for Formula (IV)

Compound # Structure

1

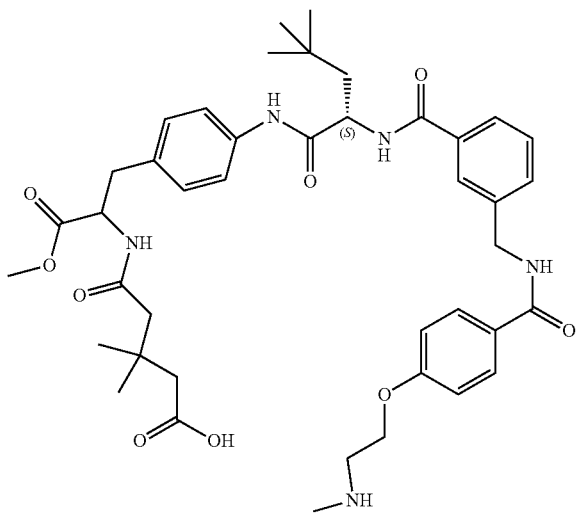

TABLE 7-continued
Exemplary compounds for Formula (IV)
Compound # Structure
2
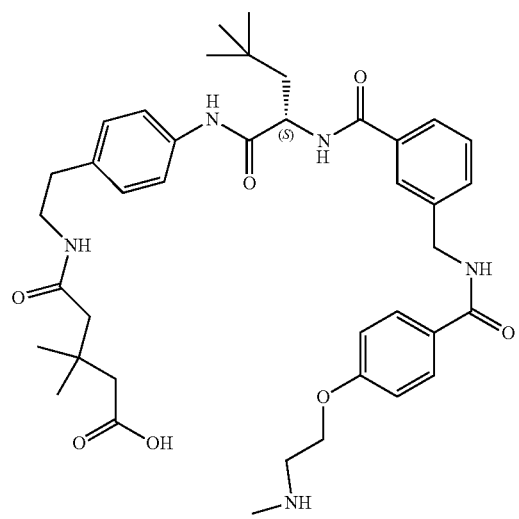
3
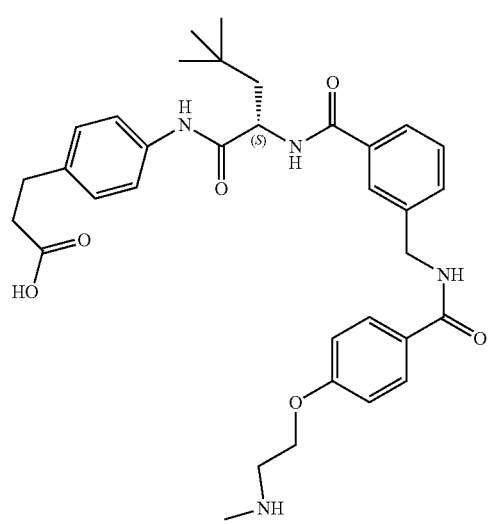
4
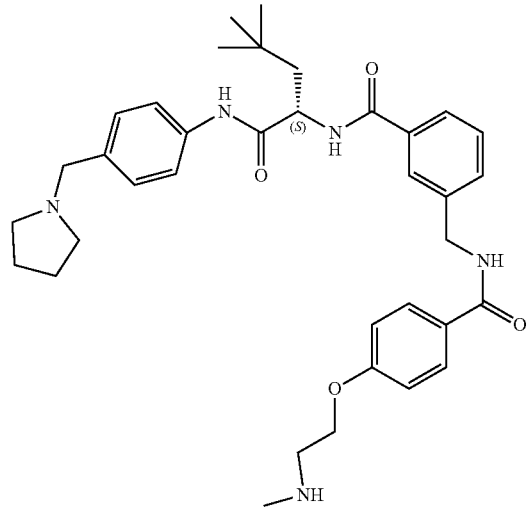

TABLE 7-continued
Exemplary compounds for Formula (IV)
| Compound # | Structure |
| --- | --- |
| 5 | 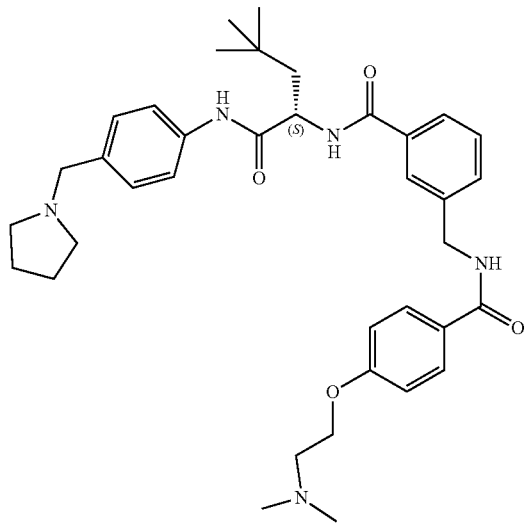 |
| 6 | 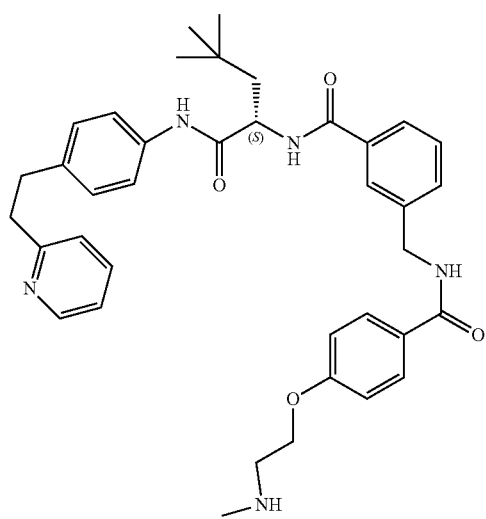 |
| 7 | 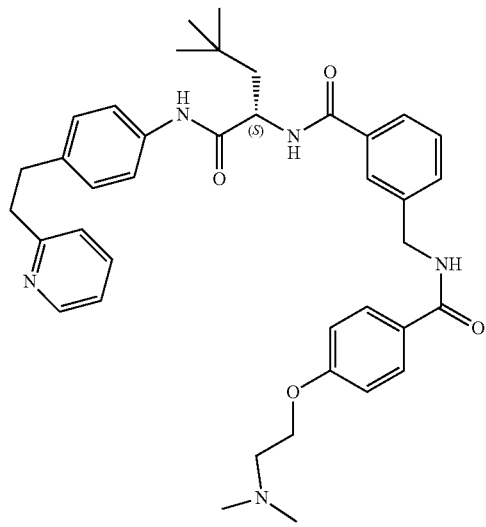 |

TABLE 7-continued
Exemplary compounds for Formula (IV)
| Compound # | Structure |
|---|---|
| 8 | 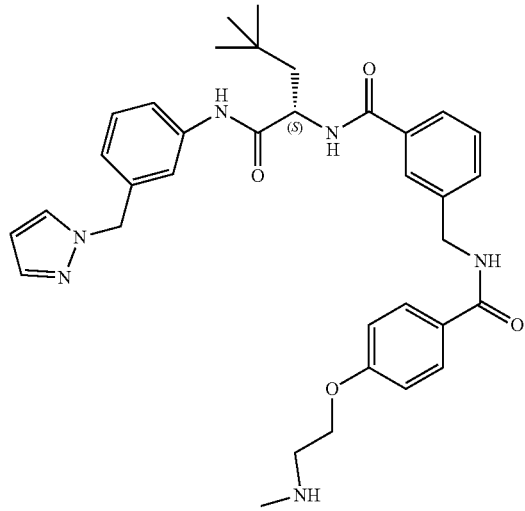 |
| 9 | 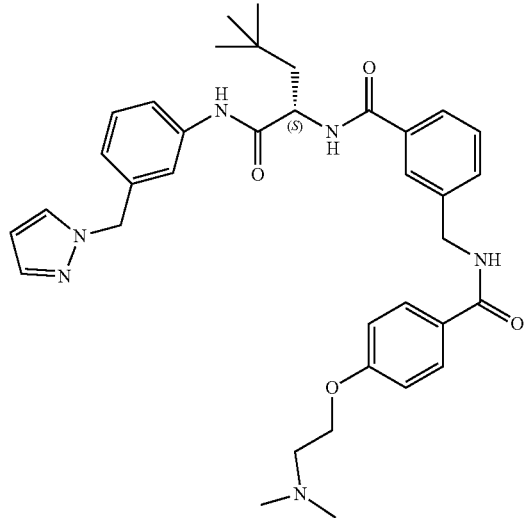 |
| 10 | 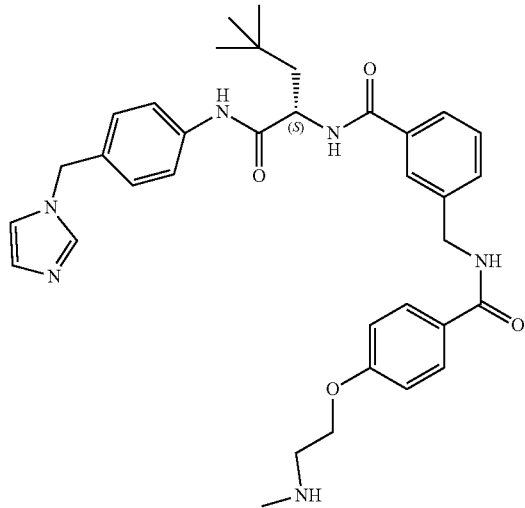 |

TABLE 7-continued

Exemplary compounds for Formula (IV)

| Compound # | Structure |
| --- | --- |
| 11 | 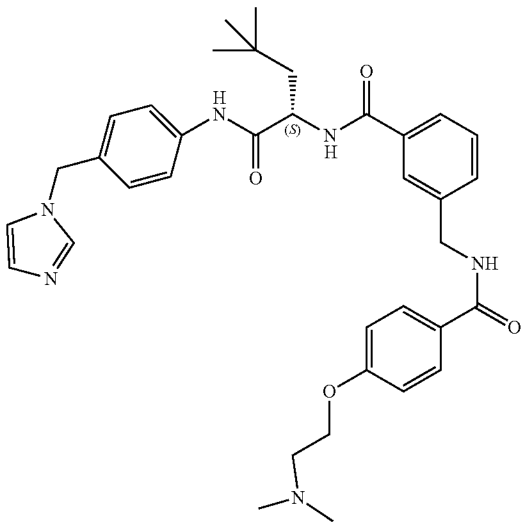 |
| 12 | 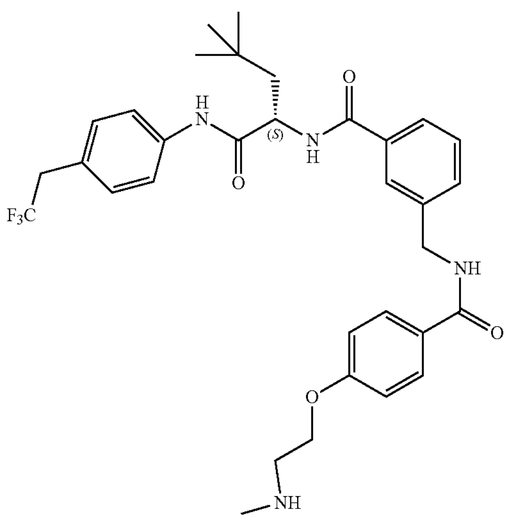 |
| 13 | 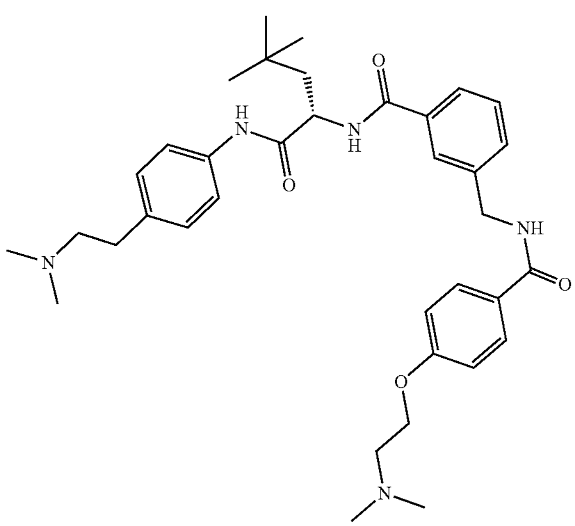 |

TABLE 7-continued

Exemplary compounds for Formula (IV)

| Compound # | Structure |
| --- | --- |
| 14 | 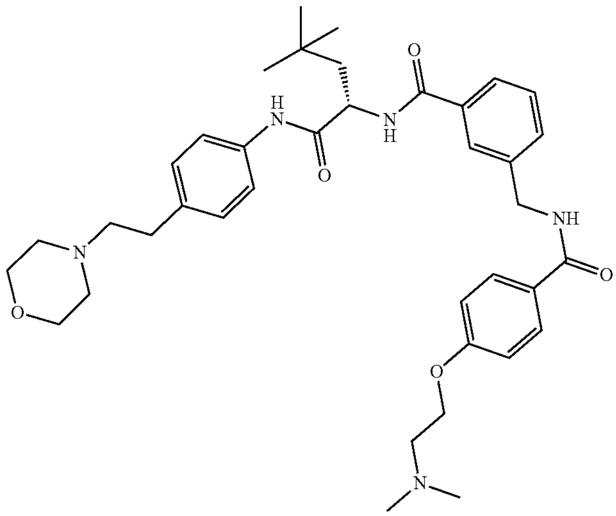 |
| 15 | 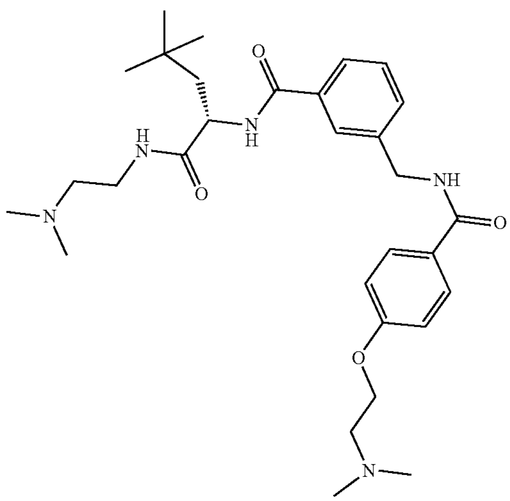 |
| 16 | 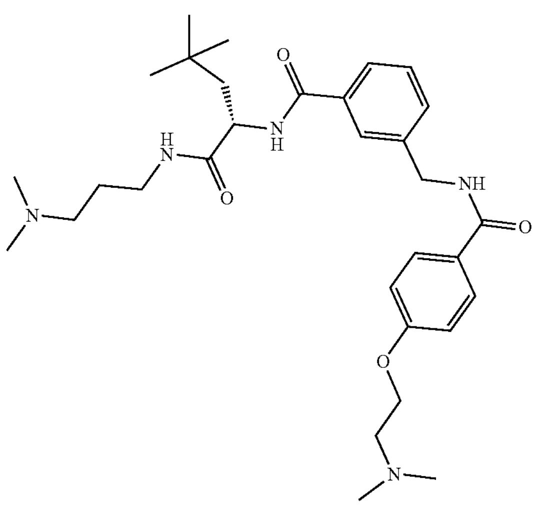 |

TABLE 7-continued
Exemplary compounds for Formula (IV)
| Compound # | Structure |
|---|---|
| 17 | 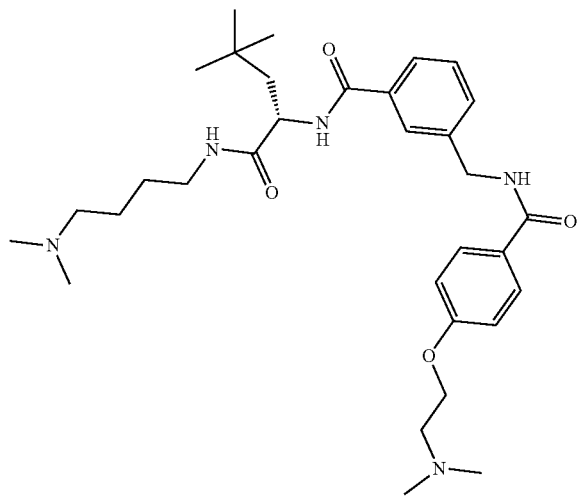 |
| 18 | 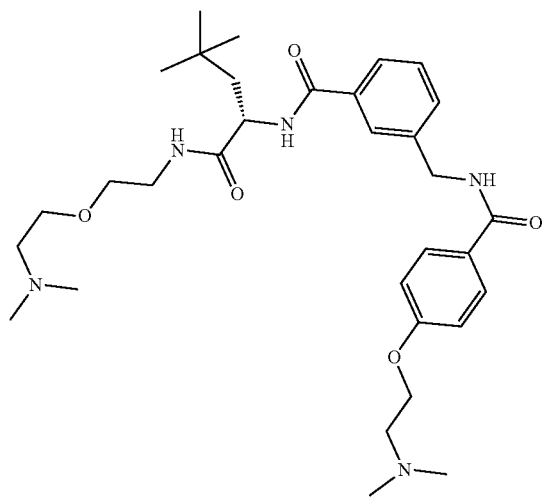 |
| 19 | 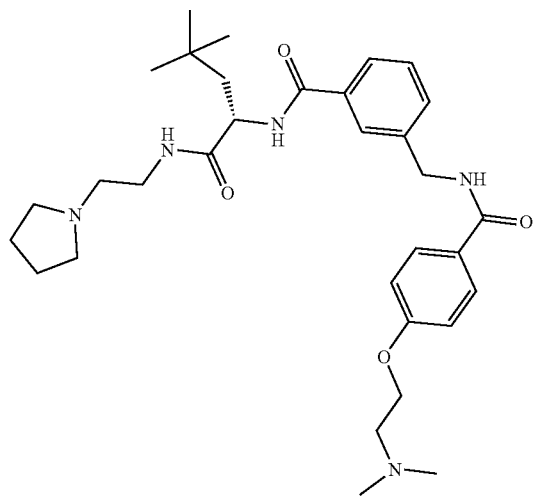 |

TABLE 7-continued
Exemplary compounds for Formula (IV)
Compound # Structure
20 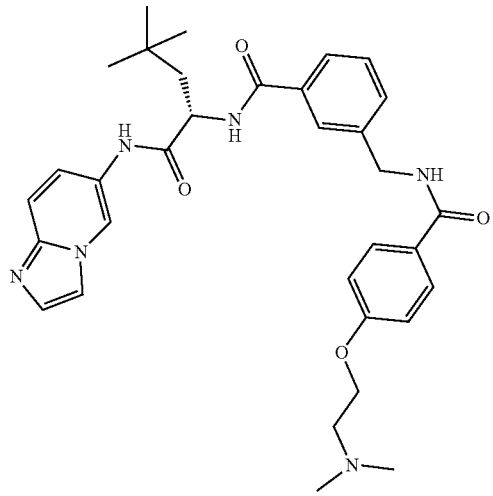
21 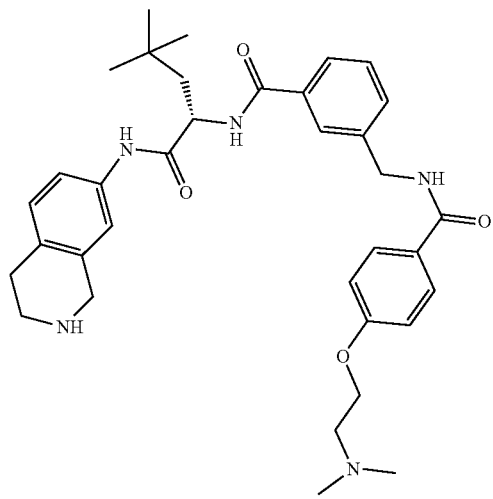
22 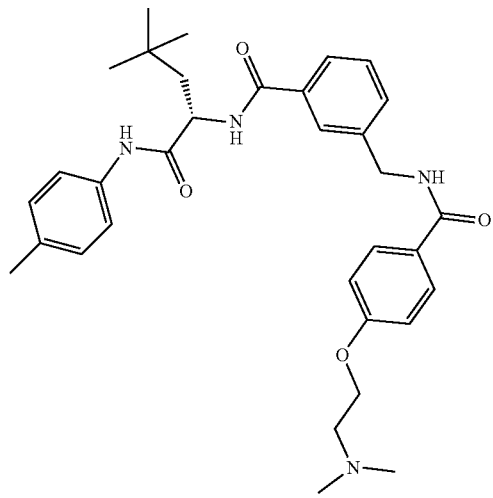

TABLE 7-continued
Exemplary compounds for Formula (IV)
Compound # Structure
23 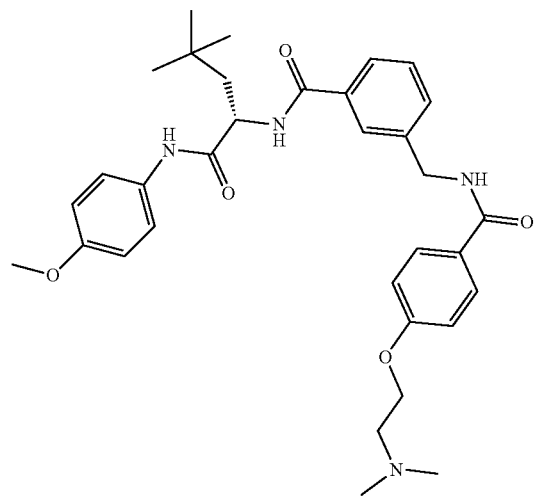
24 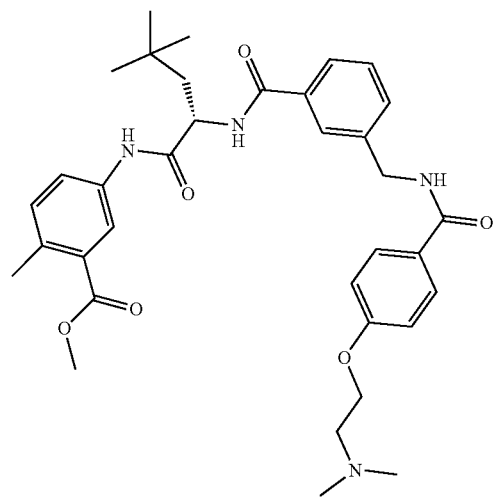
25 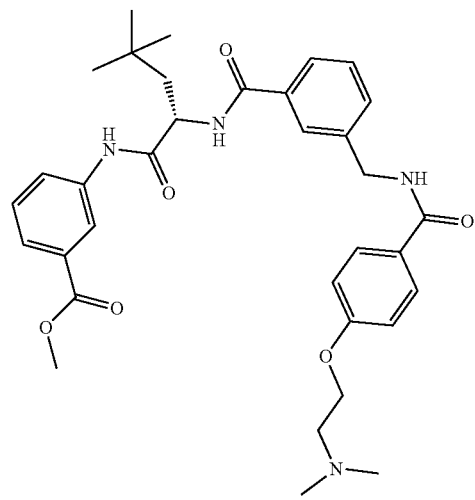

TABLE 7-continued
Exemplary compounds for Formula (IV)
Compound # Structure
26 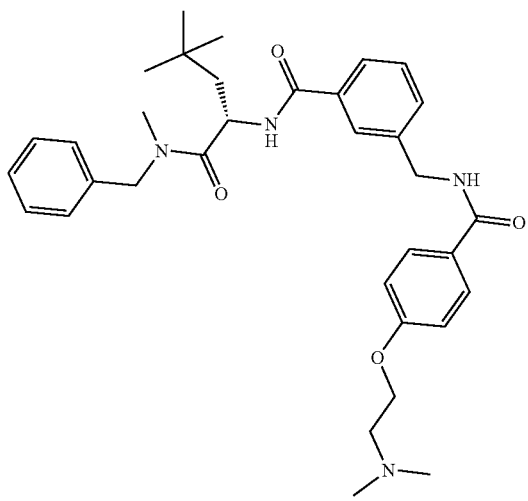
27 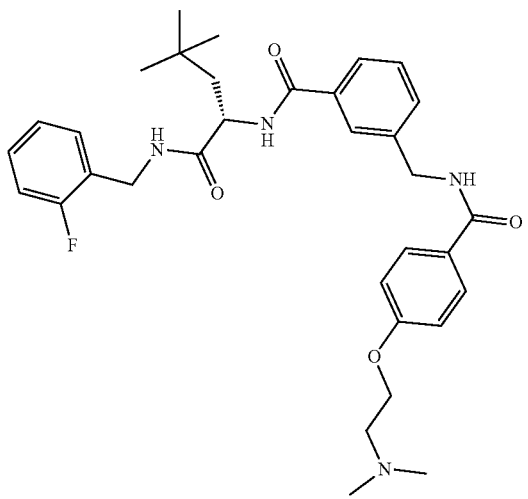
28 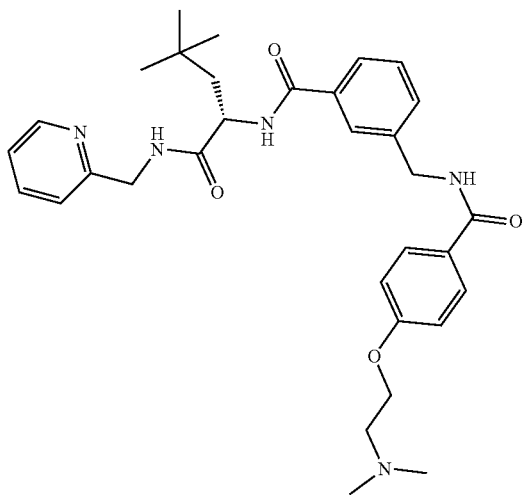

TABLE 7-continued
Exemplary compounds for Formula (IV)
Compound # Structure
29
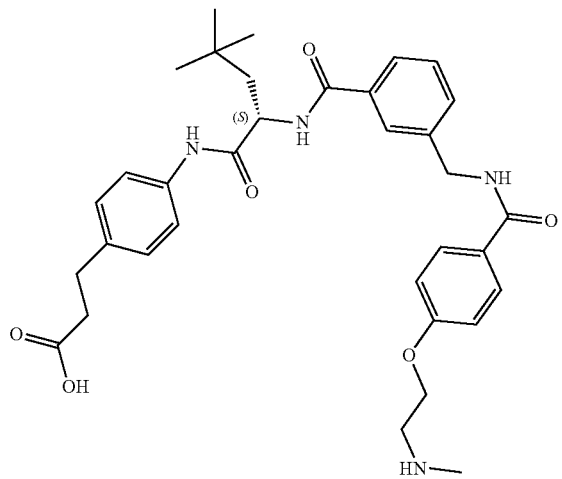
30
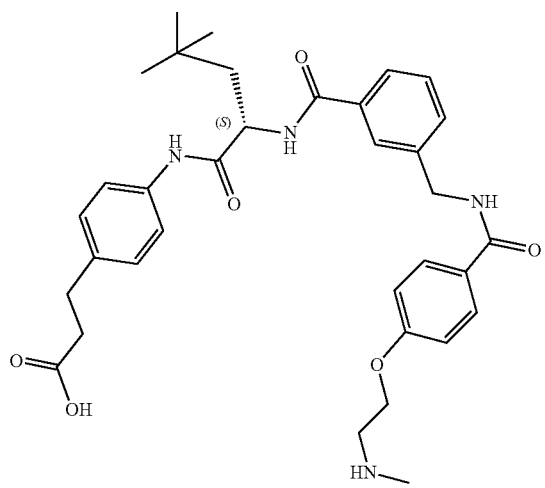
31
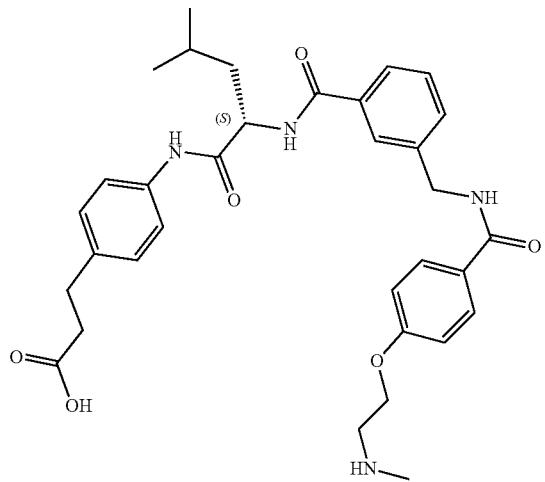

TABLE 7-continued
Exemplary compounds for Formula (IV)
Compound # Structure
32
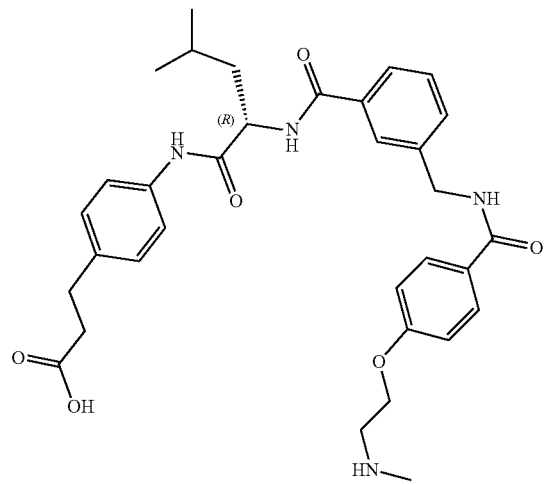
33
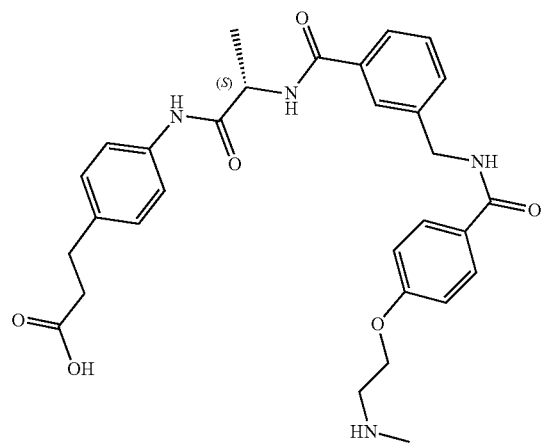
34
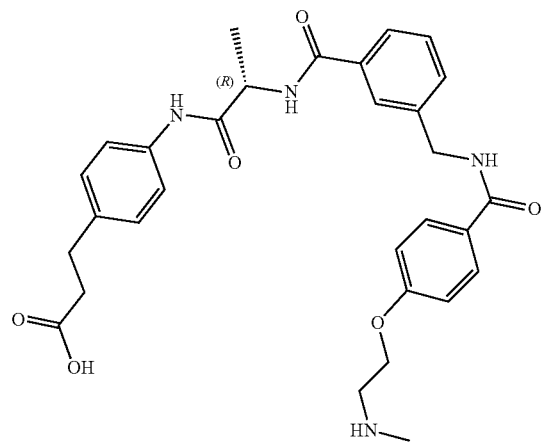

TABLE 7-continued
Exemplary compounds for Formula (IV)
| Compound # | Structure |
|---|---|
| 35 | 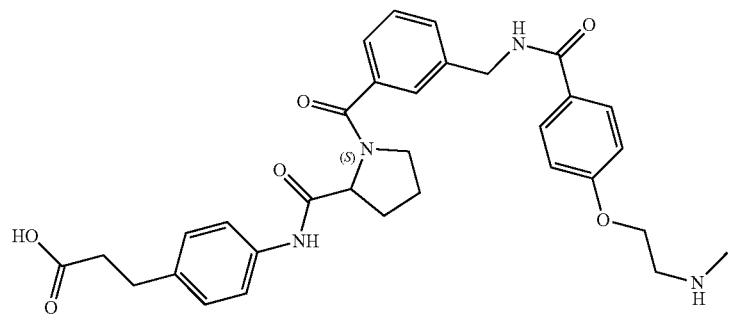 |
| 36 | 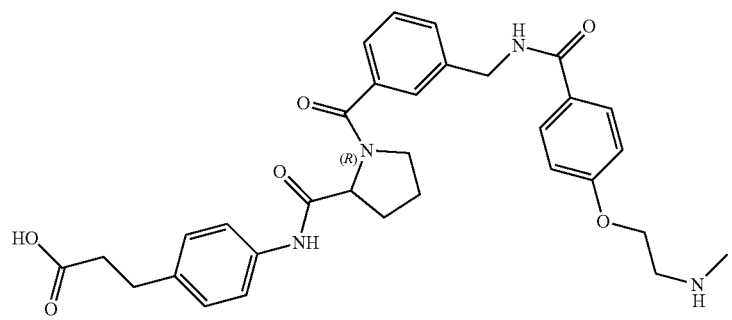 |
| 37 | 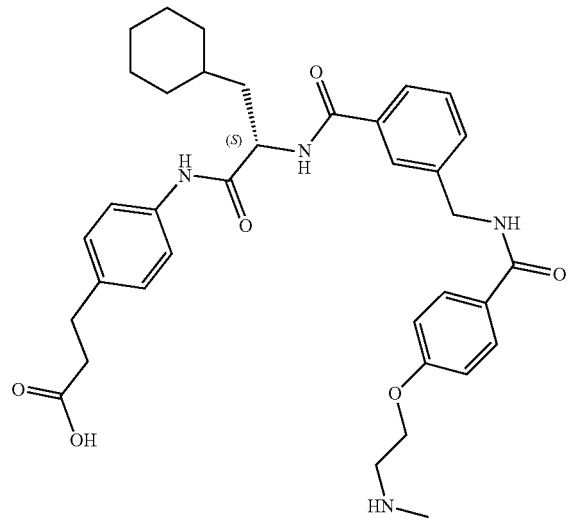 |

TABLE 7-continued
Exemplary compounds for Formula (IV)
| Compound # | Structure |
|---|---|
| 38 | 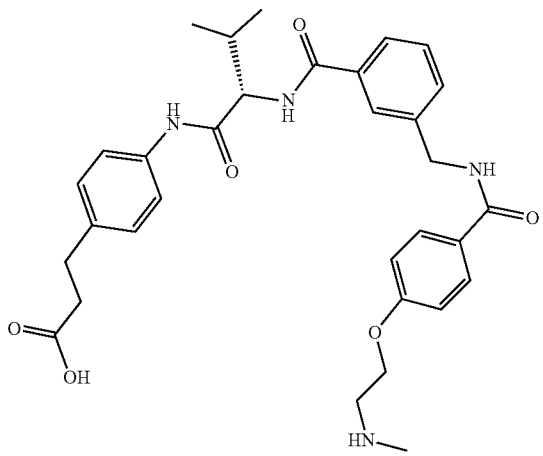 |
| 39 | 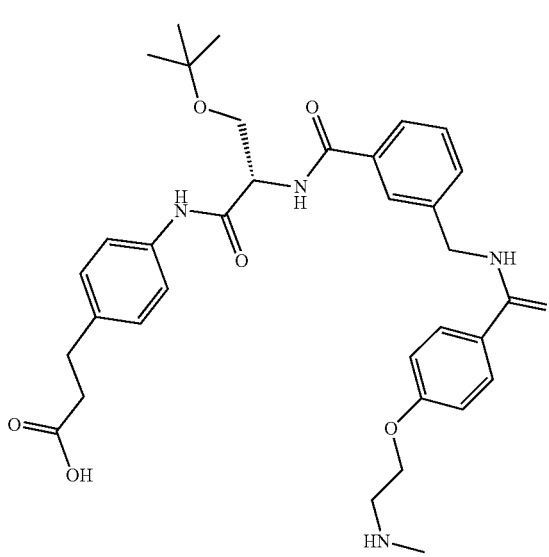 |
| 40 | 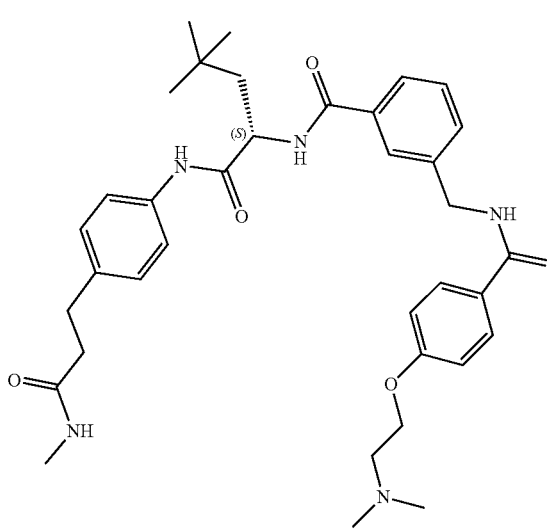 |

TABLE 7-continued
Exemplary compounds for Formula (IV)
Compound # Structure
41
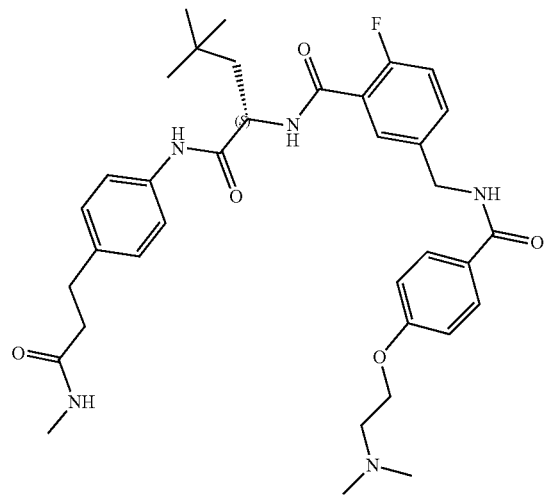
42
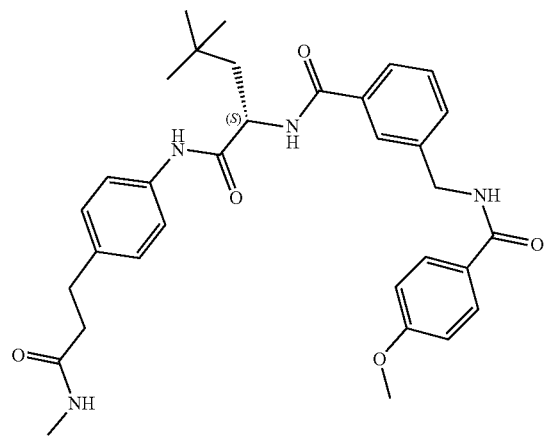
43
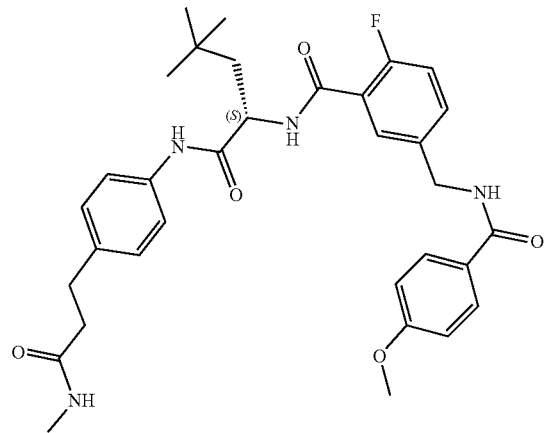

TABLE 7-continued
Exemplary compounds for Formula (IV)
Compound # Structure
44
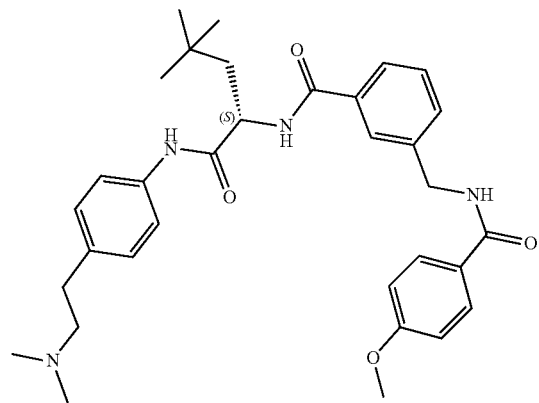
45
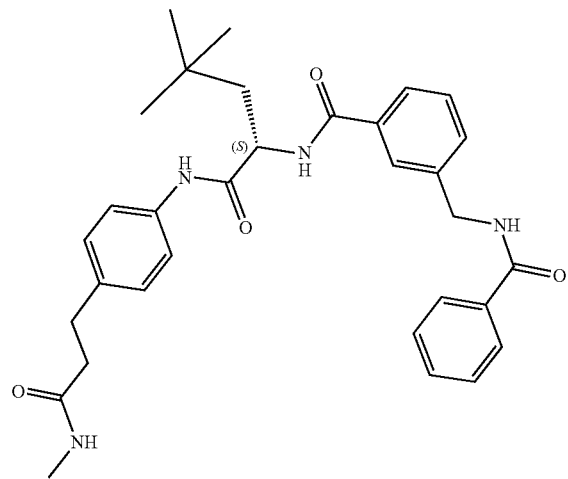
46
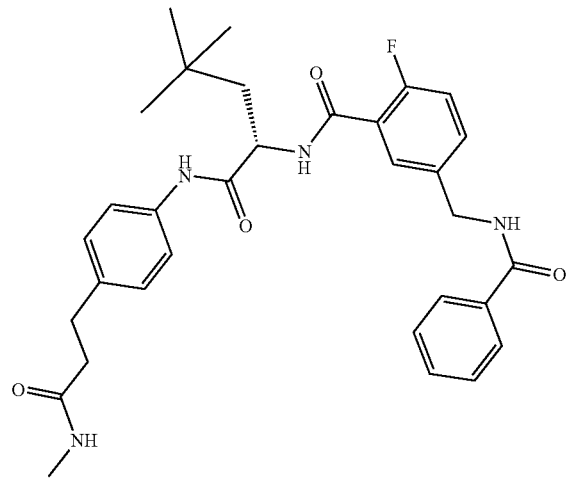

TABLE 7-continued
Exemplary compounds for Formula (IV)
Compound # Structure
47
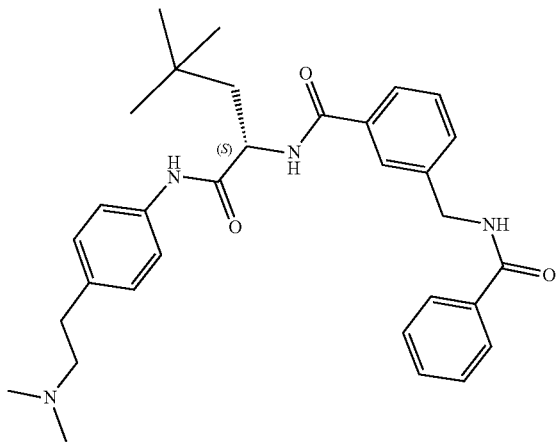
48
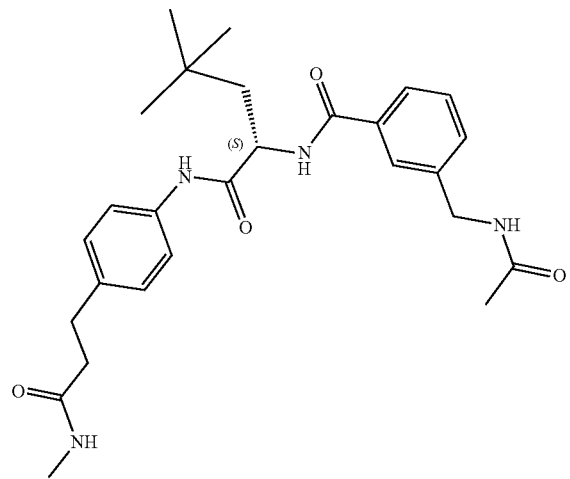
49
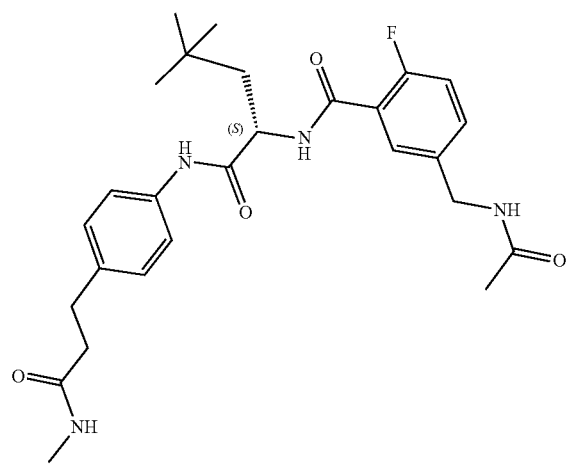

TABLE 7-continued
Exemplary compounds for Formula (IV)
Compound # Structure
50
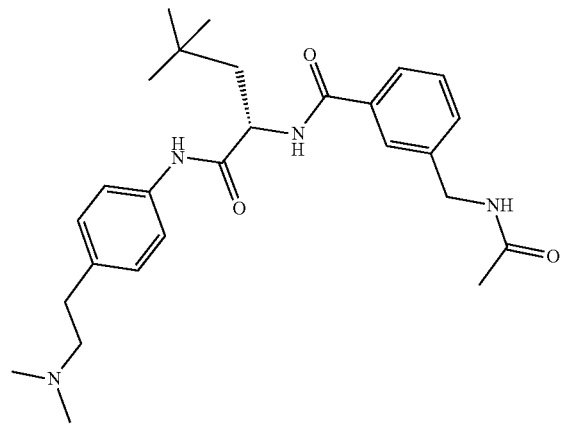
51
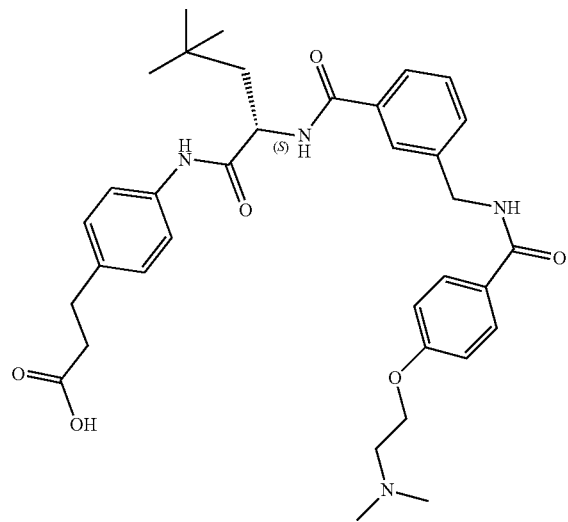
52
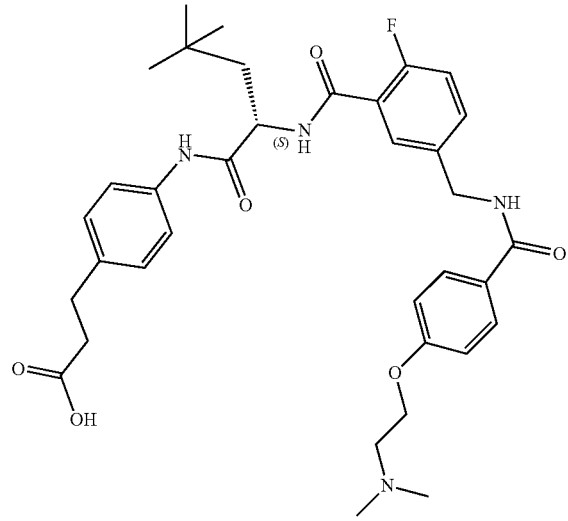

TABLE 7-continued
Exemplary compounds for Formula (IV)
Compound # Structure
53 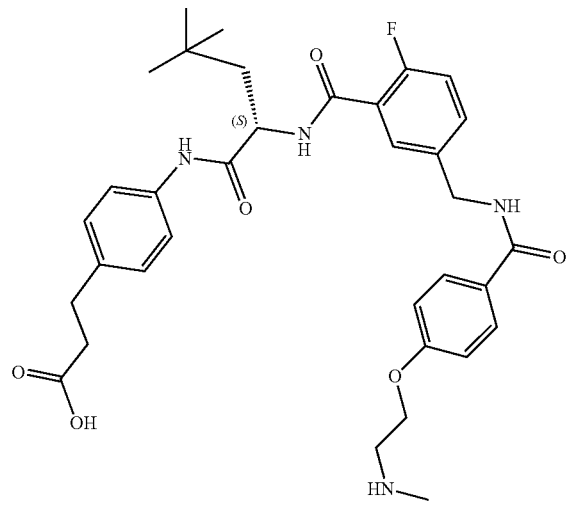
54 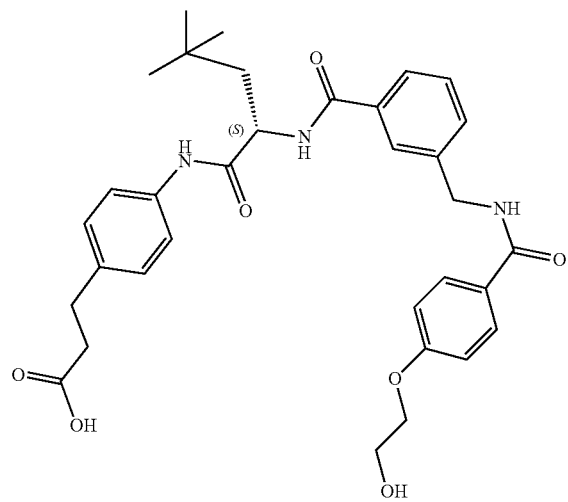
55 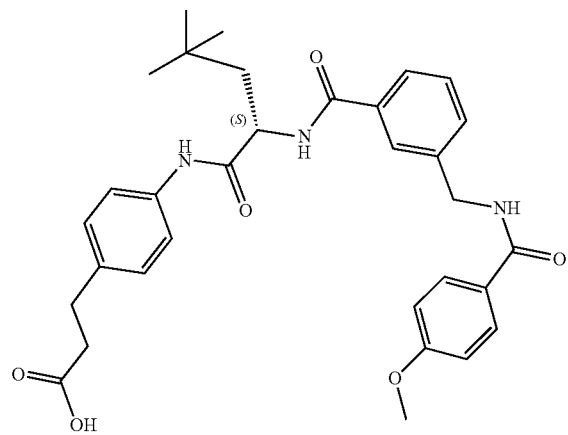

TABLE 7-continued
Exemplary compounds for Formula (IV)
Compound # Structure
56
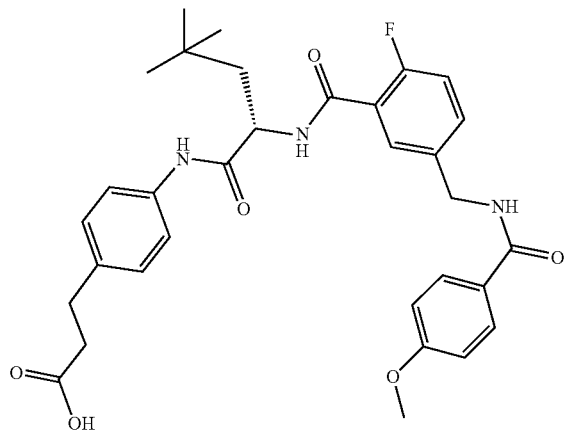
57
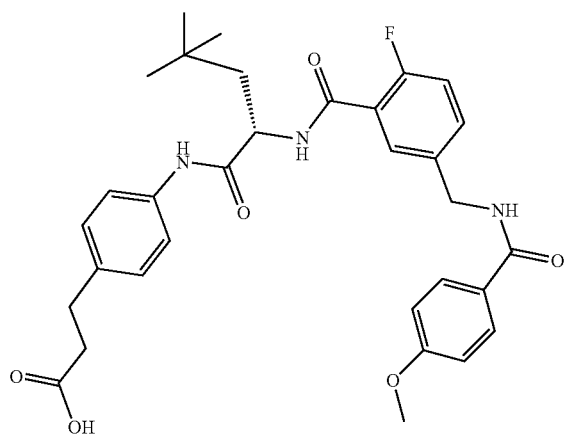
58
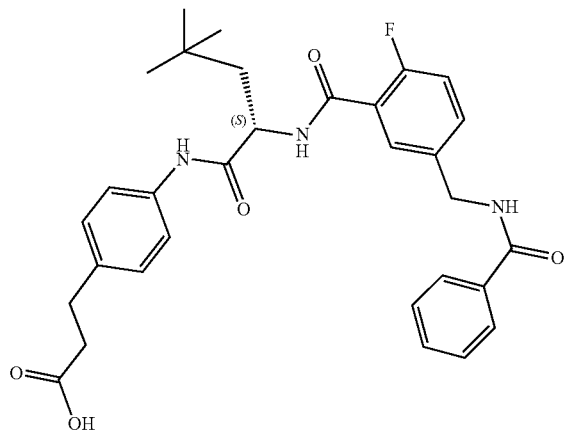

TABLE 7-continued
Exemplary compounds for Formula (IV)
Compound # Structure
59
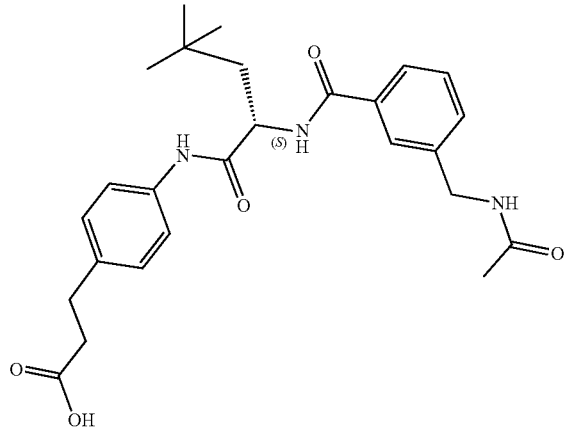
60
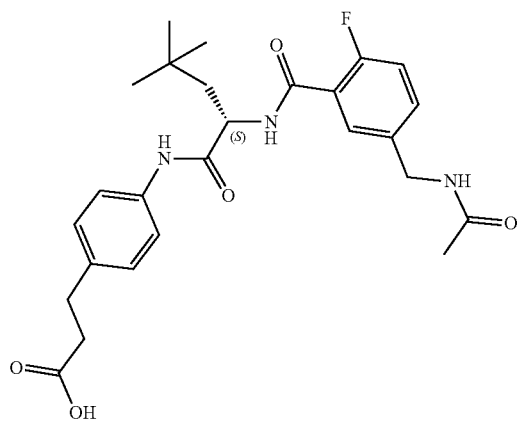
61
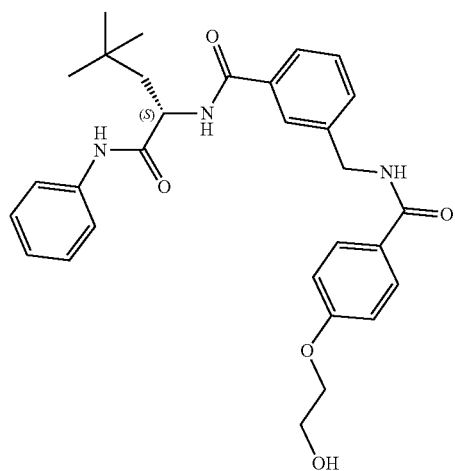

TABLE 7-continued
Exemplary compounds for Formula (IV)
| Compound # | Structure |
|---|---|
| 62 | 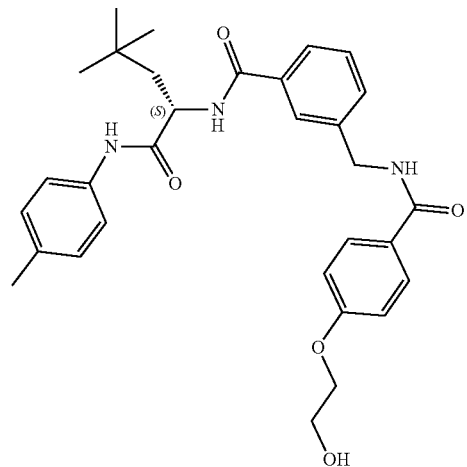 |
| 63 | 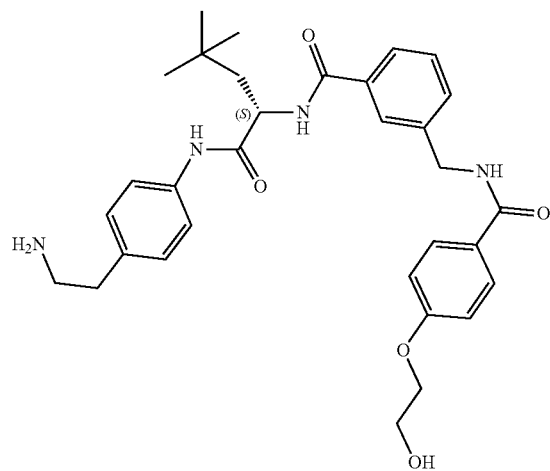 |
| 64 | 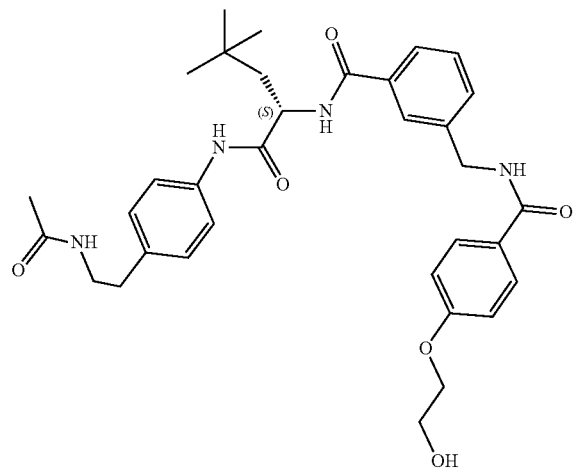 |

TABLE 7-continued
Exemplary compounds for Formula (IV)
Compound # Structure
65
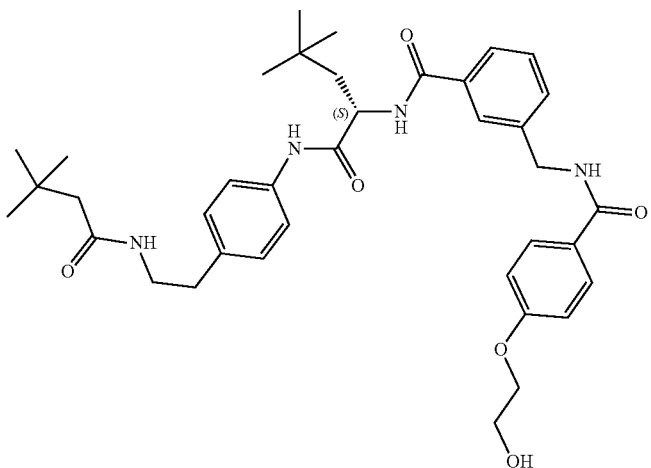
66
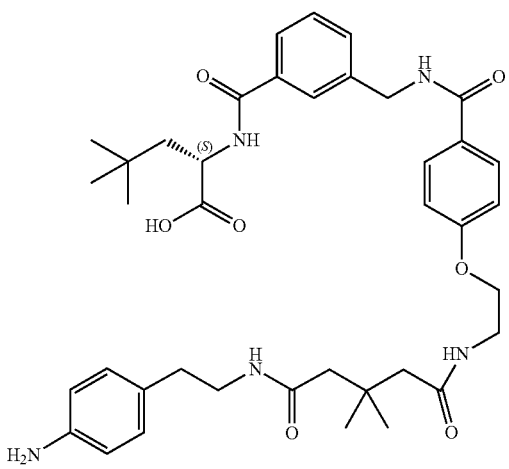
67
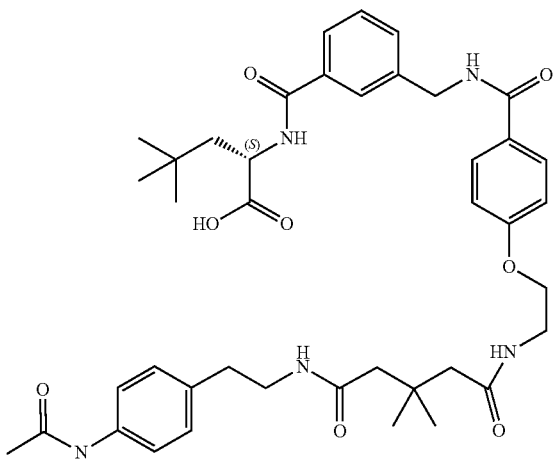

TABLE 7-continued
Exemplary compounds for Formula (IV)
Compound # Structure
68
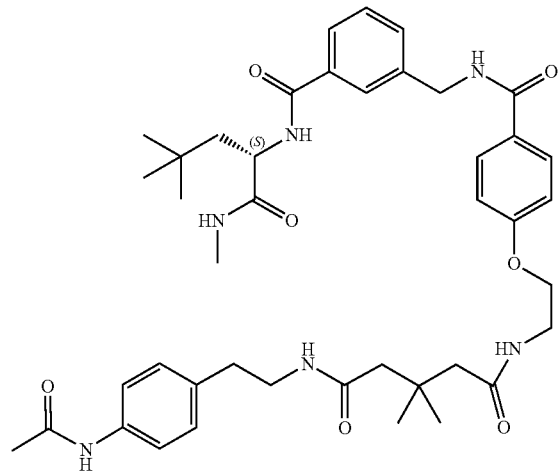
69
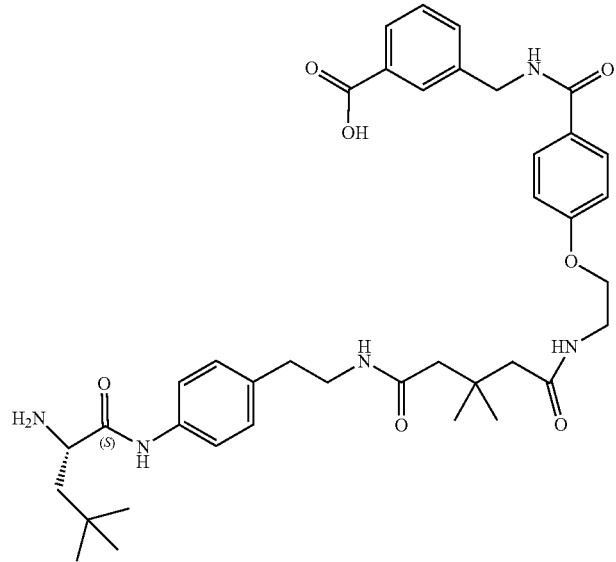

TABLE 7-continued
Exemplary compounds for Formula (IV)
Compound # Structure
70
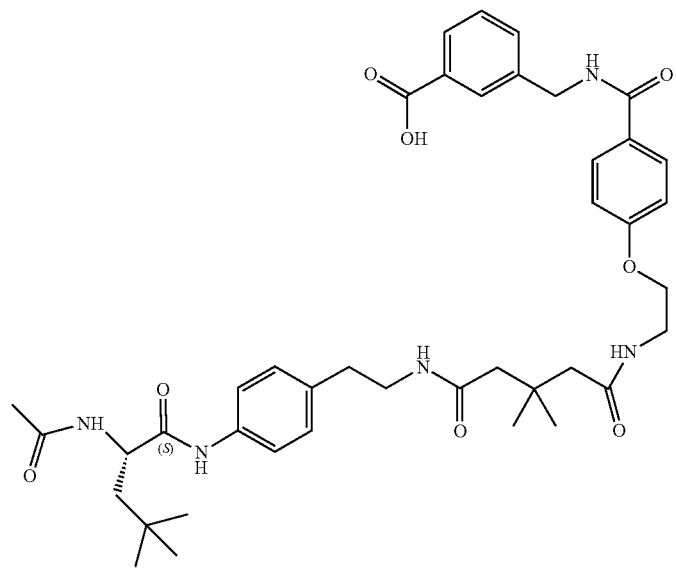
71
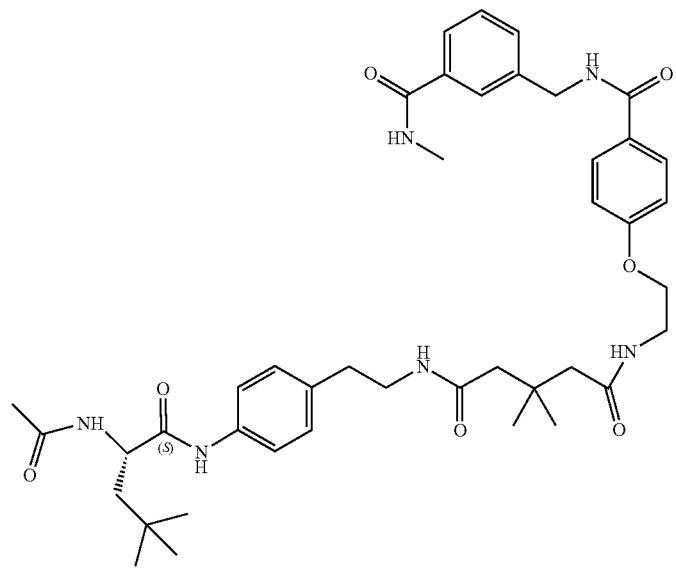

TABLE 7-continued
Exemplary compounds for Formula (IV)
| Compound # | Structure |
|---|---|
| 72 | 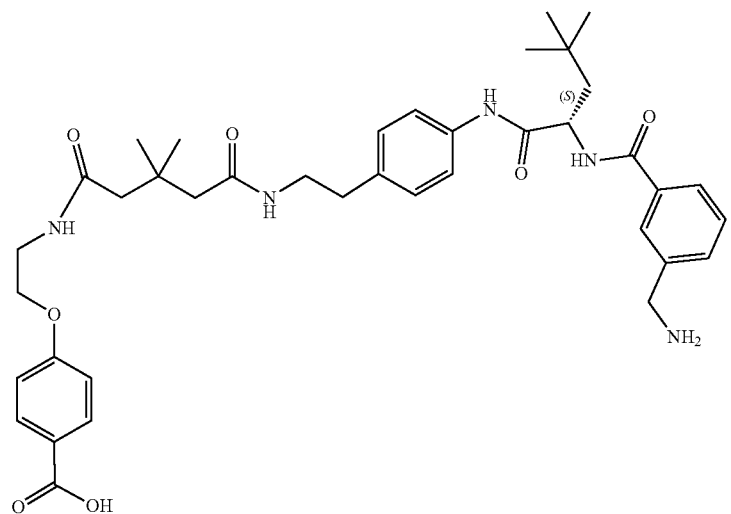 |
| 73 | 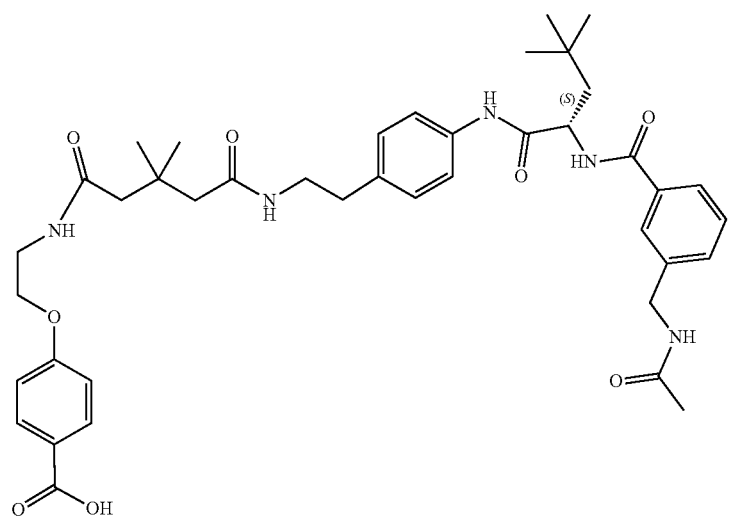 |
| 74 | 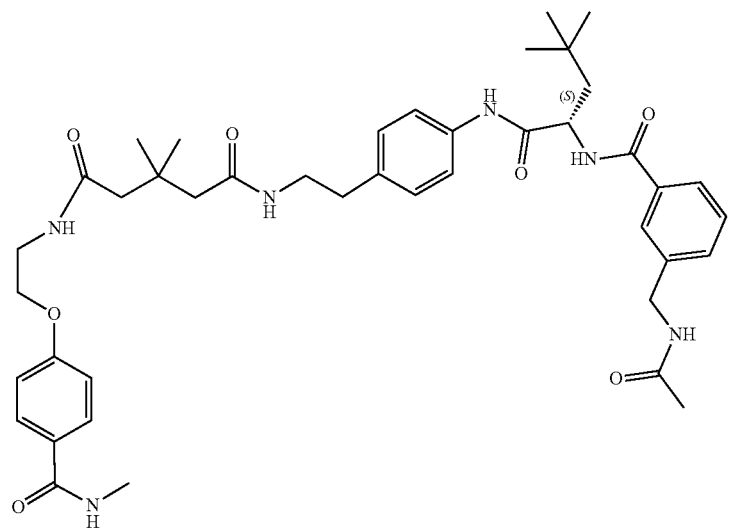 |

In some preferred embodiments, with reference to Formula (IV), r is 1, Z is Formula (Z), and $R_{10}$ and $R_{11}$ together with the carbons to which they are attached form a substituted phenyl or a substituted 6-membered heteroaryl, resulting in Formula (IVa):

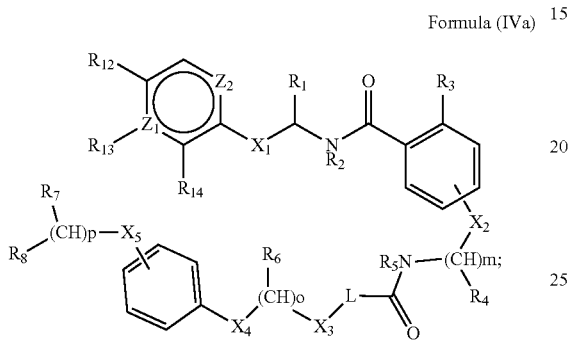

Formula (IVa)

Wherein the variables, $R_1$, $R_2$, $R_3$, $R_4$, $R_5$, $R_6$, $R_7$, $R_8$, $X_1$, $X_2$, $X_3$, $X_4$, $X_5$, m, o, and p are as defined above, including all preferred and alternative embodiments;

$Z_1$ is C or N; $Z_2$ is CH or N; preferably, $Z_1$ is C and $Z_2$ is N; or $Z_1$ is N and $Z_2$ is CH; More preferably, $Z_1$ is C and $Z_2$ is CH;

$R_{12}$ and $R_{13}$ are each independently selected from H, F, —$CH_3$, —$OCH_3$, —$COOCH_3$, —$CONHCH_3$, any one of those groups presented in Table 5, provided at least one of $R_{12}$ and $R_{13}$ is H or F; preferably, $R_{13}$ is H, $R_{12}$ is selected from H, F, —$CH_3$, —$OCH_3$, —$COOCH_3$, —$CONHCH_3$, any one of those groups presented in Table 5; More preferably, $R_{13}$ is H, $R_{12}$ is any one of those groups presented in Table 5;

Alternatively, $R_{12}$ and $R_{13}$ together with the phenyl or 6-membered heteroaryl to which they are respectively attached form a fused bicyclic ring system, such as any one of the bicyclic groups presented in Table 6; and $R_{14}$ is H, halogen, —$CH_3$, —$OCH_3$; preferably $R_{14}$ is H, F, —$CH_3$; more preferably, $R_{14}$ is H;

Nonlimiting exemplary compounds for Formula (IVa) include Compounds 1-14, 20-47, 51-58, 61-65, 66-74 in Table 7.

In some preferred embodiments, with reference to Formula (IVa), $X_1$ is —$NR_{15}C(O)$—, $X_2$ is absent, $R_4$ is H, m is 1, L, $X_3$, and $X_4$ are each absent, and o is 0, resulting in Formula (IVb):

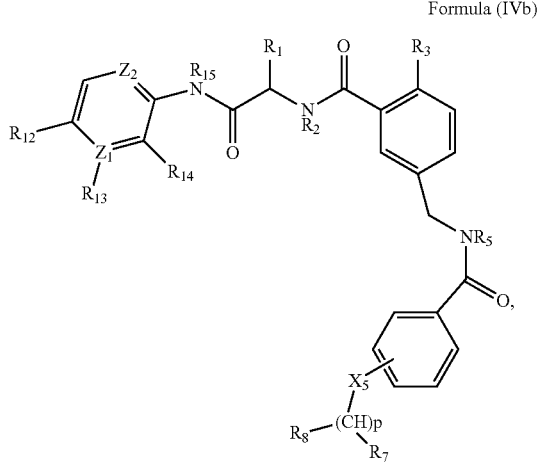

Formula (IVb)

Wherein the variables, $R_1$, $R_2$, $R_3$, $R_5$, $R_7$, $R_8$, $X_5$, p, $Z_1$, and $Z_2$ are as defined above, including all preferred and alternative embodiments; and $R_{15}$ is H or —$CH_3$; preferably, $R_{15}$ is H Nonlimiting exemplary compounds for Formula (IVa) include Compounds 1-14, 20-47, 51-58, and 61-65 in Table 7.

With reference to Formula (IVb), when $X_5$ is absent and p is 0, the compounds can be represented by the formula as shown below:

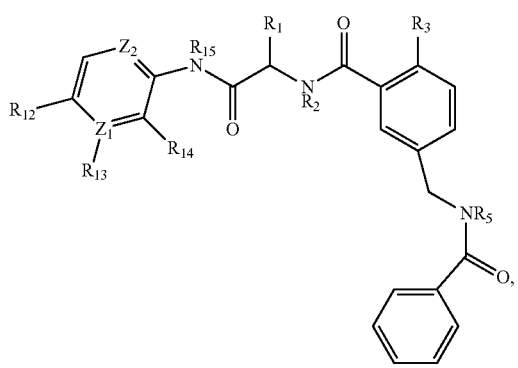

including, but not limited to, Compounds 45-47, 57, and 58.

In some preferred embodiments, with reference to Formula (IVb), $Z_1$ is C and $Z_2$ is CH, $X_5$ is —O—, $R_8$ is —$NR_{20}R_{21}$, resulting in Formula (IVc):

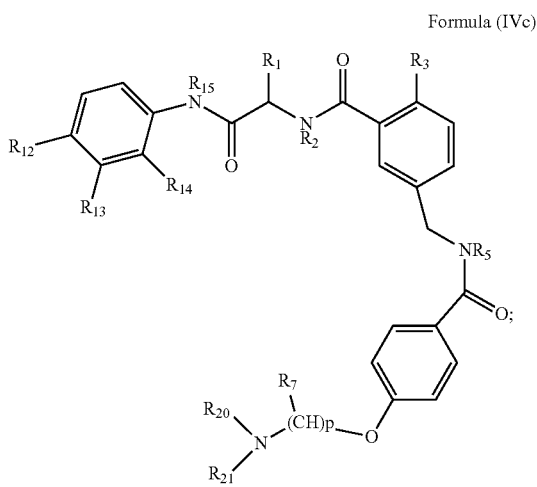

Formula (IVc)

Wherein the variables $R_1$, $R_2$, $R_3$, $R_5$, $R_7$, $R_{12}$, $R_{13}$, $R_{14}$, $R_{15}$, and p are as defined above, including all preferred and alternative embodiments;

$R_{20}$ and $R_{21}$ are each independently selected from H, halogen, a substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, or substituted or unsubstituted heterocycloalkyl; alternatively, $R_{20}$ and $R_{21}$ together with the N to which they are attached form a 5- or 6-membered heterocyclic ring.

Preferably, p is 2. Preferably, $R_7$ is H.

Preferably, $R_{20}$ and $R_{21}$ are each independently H or —$CH_3$. More preferably, one of $R_{20}$ and $R_{21}$ is H and the other is —$CH_3$; or $R_{20}$ and $R_{21}$ both are —$CH_3$.

Non-limiting exemplary compounds include Compounds 1-14, 20-41, and 51-53 in Table 7.

In some embodiments, with reference to Formula (IV), $X_1$ is —$NR_{15}C(O)$—; $X_2$ is absent; $R_4$ is H; m is 1; Z is Formula (Z), wherein L, $X_3$, and $X_4$ are each absent, and o is 0; $X_5$ is —O—, $R_8$ is —$NR_{20}R_{21}$; and $R_{10}$ and $R_{11}$ together with the carbons to which they are attached form a substituted phenyl, wherein —$(CHR_9)s$-$X_6$ is a phenyl substituent and $X_6$ is —$(CHR_{18})_q$—$X_8$-$L$-$R_{19}$; resulting in Formula (IVd):

Formula (IVd)

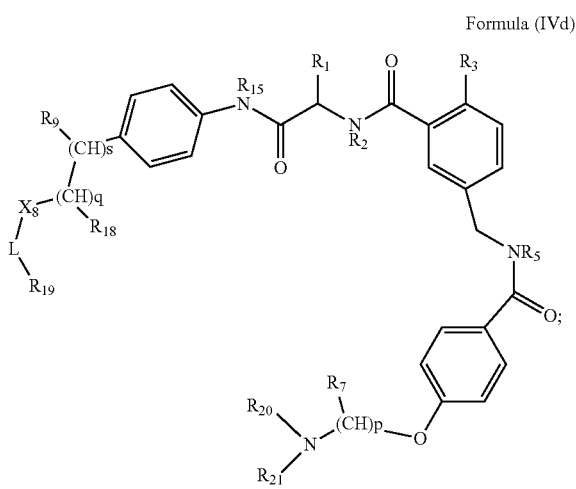

Wherein the variables $R_1$, $R_2$, $R_3$, $R_5$, $R_7$, $R_9$, $X_8$, L, $R_{18}$, $R_{19}$, $R_{20}$, $R_{21}$, L, s, p, and q are as defined above, including all preferred and alternative embodiments.

$X_8$ is absent, —CONH—, —NHC(O)—, —N($CH_3$)—, —OC(O)—, —C(O)O—, —O—, —NHC(O)NH—; preferably, $X_s$ is —NHC(O)—;

Preferably, L is —$CH_2C(CH_3)_2CH_2$—.

Preferably, q and s are independently 1 or 2. More preferably, the sum of q and s is 2.

In some cases, $R_{18}$ and $R_1$ are each independently selected from H, F, Cl, OH, —$CH_3$, —$CH_2CH_3$, —$CH(CH_3)_2$, —$C(CH_3)_3$, —$CH_2C(CH_3)_3$, —O-unsubstituted $C_{1-6}$ alkyl, —NH-unsubstituted $C_{1-6}$ alkyl, —CONH-unsubstituted $C_{1-6}$ alkyl, —NHCO-unsubstituted $C_{1-6}$ alkyl, —COO—unsubstituted $C_{1-6}$ alkyl, —$OCH_3$, —$NH_2$, —$CONH_2$, —NHCOOH, —COOH, or —CN.

Preferably, $R_{18}$ is H or a —COO-unsubstituted $C_{1-6}$ alkyl, such as —$COOCH_3$.

Preferably, Rig is —COOH.

Non-limiting exemplary compounds include Compounds 1 and 2 in Table 7.

In some embodiments, with reference to Formula (IV), $X_1$ is —$NR_{15}C(O)$—; $X_2$ is absent; $R_4$ is H; m is 1; Z is —$C(O)CH_3$; and $R_{10}$ and $R_{11}$ together with the carbons to which they are attached form a substituted phenyl, wherein $X_6$ is —$(CHR_{18})_q$—$R_{19}$; resulting in Formula (IVe):

Formula (IVe)

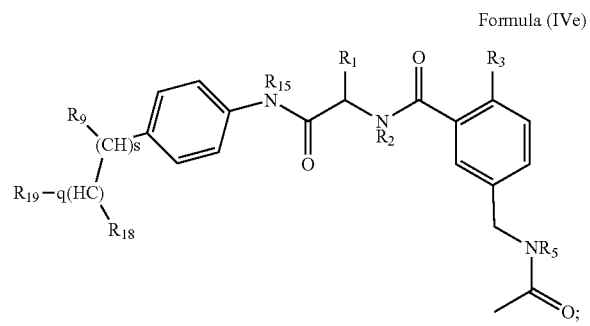

Wherein the variables $R_1$, $R_2$, $R_3$, $R_5$, $R_9$, $R_{15}$, $R_{18}$, $R_{19}$, s, and q are as defined above, including all preferred and alternative embodiments.

In some cases, $R_2$, $R_5$, $R_9$, $R_{15}$ and $R_{18}$ are each H.

In some cases, $R_3$ is H or F.

Preferably, the sum of s and q is 2.

Preferably, Rig is —COOH, —$CONH_2$, —$CONHCH_3$, —$N(CH_3)_2$, or —$NH_2$.

Non-limiting exemplary compounds for Formula (IVe) include Compounds 48-50, 59, and 60 in Table 7.

In some embodiments, with reference to Formula (IV), $X_1$ is —$NR_{15}C(O)$—; $X_2$ is absent; $R_4$ is H; m is 1; Z is Formula (Z), wherein L, $X_3$, and $X_4$ are each absent, and o is 0; $X_5$ is —O—, $R_8$ is —$NR_{20}R_{21}$; and $X_6$ is —$NR_{22}R_{23}$; resulting in Formula (IVf):

Formula (IVf)

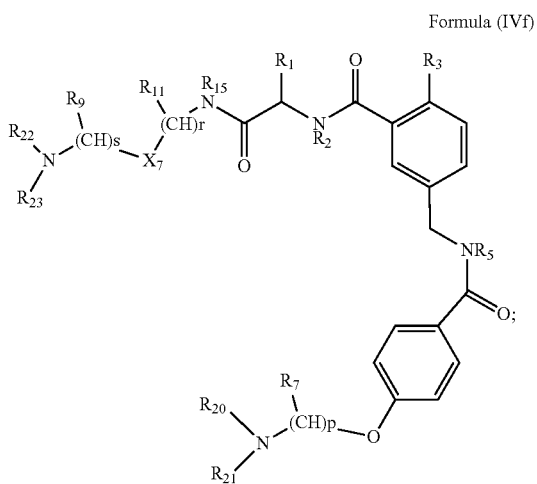

Wherein the variables $R_1$, $R_2$, $R_3$, $R_5$, $R_7$, $R_9$, $R_{11}$, $R_{15}$, $R_{20}$, $R_{21}$, $X_7$, p, s, and r are as defined above, including all preferred and alternative embodiments; and $R_{22}$ and $R_{23}$ are each independently selected from H, $^2$H, halogen, substituted or unsubstituted alkyl; and optionally, $R_{22}$ and $R_{23}$ together with the N to which they are attached form a substituted or unsubstituted 5- or 6-membered heterocyclic ring having zero, one or more heteroatoms in addition to the N.

Preferably, $R_2$, $R_5$, $R_9$, $R_1$, and $R_{15}$ are each H.

Preferably, $X_7$ is absent or —O—.

Preferably, $X_7$ is absent, the sum of s and r is 1, 2, 3, or 4.

Preferably, $X_7$ is —O—, s is 2, and r is 2.

Preferably, $R_{22}$ and $R_{23}$ are each —CH$_3$; or $R_{22}$ and $R_{23}$ together with the N to which they are attached form pyrrolidine.

Non-limiting exemplary compounds for Formula (IVf) include Compounds 15-19 in Table 7.

With reference to Formula (IV) and (IVa)-(IVf), preferably, $R_1$ is —CH$_2$C(CH$_3$)$_3$; $R_2$, $R_3$, and $R_5$ are each H.

Deubiquitinases (DUBs)

Deubiquitinating enzymes (i.e., deubiquitinases or DUBs) are typically a cysteine protease and may be classified into subgroups as ubiquitin-specific proteases (USP) and ubiquitin C-terminal hydrolases (UCH). Examples of DUBs include, for instance, USP5, USP6, USP4, USP5, USP13, USP2, USP 11, USP14, USP7, USP9X, USP10, USP1, USP12, USP16, USP15, USP17, USP19, USP20, USP3, USP9Y, USP18, USP21, USP22, USP33, USP29, USP25, USP36, USP32, USP26, USP24, USP42, USP46, USP37, USP28, USP47, USP38, USP44, USP50, USP35, USP30, Mername-AA088peptidase, Mername-AA091 peptidase, USP45, USP51, USP34, USP48, USP40, USP31, Mername-AA129peptidase, USP49, USP17-like peptidase, USP54, USP53, USP39, UCH-L1, UCH-L3, UCH-BAP1, UCH37, Cezanne deubiquitinating peptidase, Cezanne2, tumor necrosis factor alpha-induced protein 3, TRABID protein, VCP(p97)/p47-interacting protein, otubain1, otubain2, CylD protein, SENP1 peptidase, SENP3 peptidase, SENP6 peptidase, SENP2 peptidase, SENP5peptidase, SENP7peptidase, SENP8peptidase, SENP4peptidase, Pohl peptidase, Jab1/MPN domain metalloenzyme, Mername-AA 165 peptidase, Mername-AA 166 peptidase, Mername-AA 167 peptidase, Mername-AA168 protein, COPS signalosome subunit6, 26S proteasome non-ATPase regulatory subunit7, eukaryotic translation initiation factor3 subunit5, IFP38 peptidase homologue, autophagin (ATG), ovarian tumor (OTU) domain proteins, Josephin-domain (JD) or Machado-Joseph disease (MJD) proteins, ubiquitin-like protein-specific protease (ULP), and JAMM (Jab1/MPN domain-associated metalloisopeptidase) domain proteins. The compounds of the invention preferably selectively inhibit Usp9x.

The term "alkyl" as used herein, refers to saturated, unsaturated, straight- or branched-chain, or cyclic hydrocarbon radicals. "$C_1$-$C_4$ alkyl", "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, denotes a monovalent group derived from a hydrocarbon moiety having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, denotes a monovalent group derived from a hydrocarbon moiety having at least one carbon-carbon triple bond by the removal of a single hydrogen atom. "$C_2$-$C_8$ alkynyl," "$C_2$-$C_{12}$ alkynl", "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like. Alkenyls and alkynyls are "unsaturated alkyls."

The term "cycloalkyl", as used herein, refers to a monocyclic or polycyclic saturated (or unsaturated) carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to mono-cyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

The term "aryl," as used herein, refers to a mono- or polycyclic carbocyclic ring system having one or two aromatic rings including, but not limited to, phenyl, naphthyl, tetrahydronaphthyl, indanyl, idenyl and the like.

The term "heteroaryl," as used herein, refers to a mono- or polycyclic (e.g. bi-, or tri-cyclic or more) aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O) C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms on an alkyl group (substituted alkyl) or aryl group (substituted aryl) with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —NO$_2$, —N3, —CN, —NH$_2$, protected amino, oxo, thioxo, —NH—$C_2$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_2$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_2$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)—heterocycloalkyl, —CONH$_2$, —CONH—$C_2$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —OCO$_2$—$C_2$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_2$-$C_{12}$ alkyl, —CO$_2$—$C_2$-$C_8$ alkenyl, —CO$_2$—$C_2$-$C_8$ alkynyl, CO$_2$—$C_3$-$C_{12}$-cycloalkyl, —CO$_2$— aryl, CO$_2$-heteroaryl, CO$_2$-heterocycloalkyl, —OCONH$_2$, —OCONH—$C_2$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_2$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —NHCO$_2$—$C_2$-$C_{12}$-alkyl, —NHCO$_2$—$C_2$-$C_8$-alkenyl, —NHCO$_2$— $C_2$-$C_8$-alkynyl, —NHCO$_2$—$C_3$-$C_{12}$-cycloalkyl, —NHCO$_2$-aryl, —NHCO$_2$-heteroaryl, —NHCO$_2$— heterocycloalkyl, —NHC(O)NH$_2$, —NHC(O)NH—$C_2$-$C_{12}$-alkyl, —NHC(O) NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH— heterocycloalkyl, NHC(S)NH$_2$, —NHC(S)NH—$C_2$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH— heteroaryl, —NHC(S)NH-heterocycloalkyl, —NHC(NH)NH$_2$, —NHC(NH)NH—$C_2$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)

NH-heterocycloalkyl, —NHC(NH)—$C_2$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_2$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_2$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_2$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_2$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_2$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S— heterocycloalkyl, or methylthio-methyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$. Preferably, a substituted alkyl group is substituted with one or more halogen atoms, more preferably one or more fluorine or chlorine atoms.

The term "halo" or "halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen," or H, includes hydrogen and deuterium ($^2$H or D). In addition, the recitation of an atom includes other isotopes of that atom so long as the resulting compound is pharmaceutically acceptable.

The salts, e.g., pharmaceutically acceptable salts, of the disclosed therapeutics or compounds may be prepared by reacting the appropriate base or acid with a stoichiometric equivalent of the therapeutic or compound. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

Figure 1E:
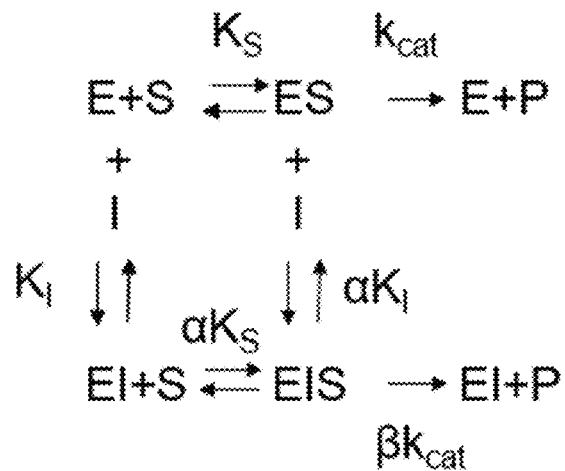
FIG. 1E illustrates the set of reactions that comprise the inhibition of enzyme activity. The values of all the parameters may be determined by a series of steady state kinetic measurements. The values determined for the parameters α and β determine the specific mode of inhibition.
Figure 1F:
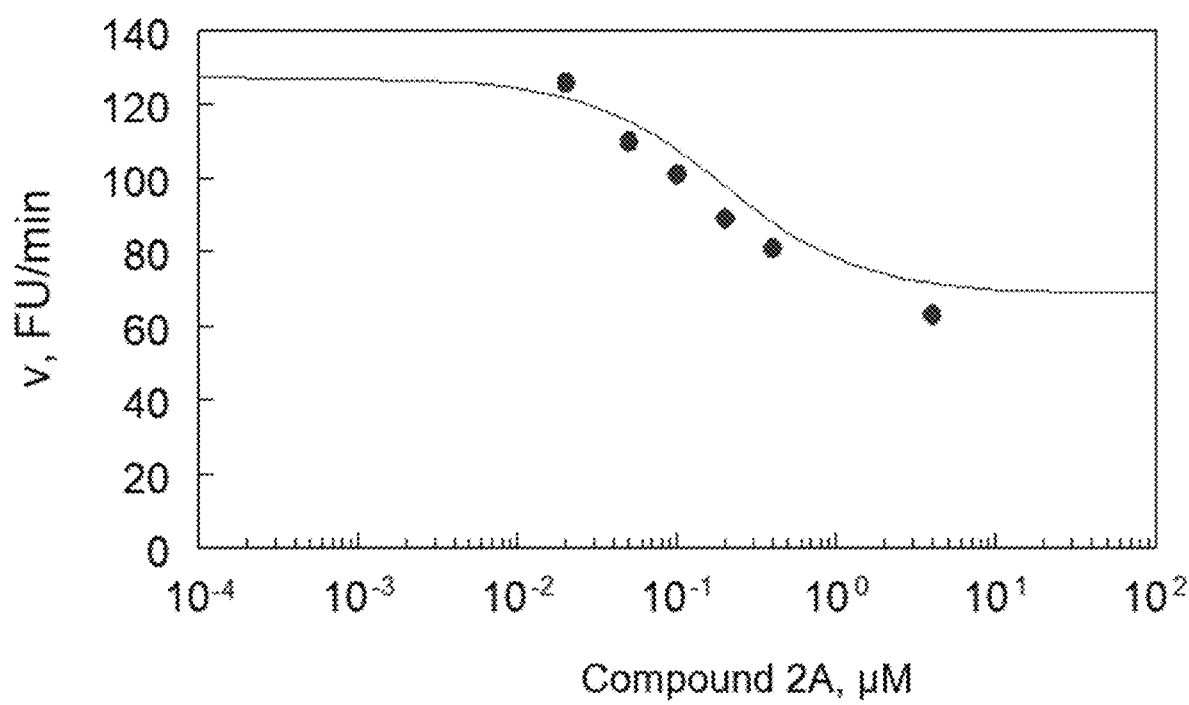
FIG. 1F is a graph comparing the experimental data of Compound 2A (solid dot) with the partial inhibition dose-response curve based on the kinetic model of hyperbolic mixed inhibition.

The terms "inhibit" as used herein with respect to the activity of the USP9X inhibitor, refer to the ability to substantially antagonize, prohibit, prevent, restrain, slow, disrupt, alter, eliminate, stop, or reverse the progression or severity of, for example, the catalytic activity of a DUB such as USP9X, the survival or proliferation of a cancer cell, or a disease or condition associated with USP9X. The USP9X inhibitor of the invention preferably inhibits the catalytic activity of USP9X by at least about 20%, about 30%, about 40%, about 50%, about 60%, about 70%, about 80%, about 90%, about 95%, about 100%, or a range defined by any two of the foregoing values. In some embodiments, the compounds as described can inhibit USP9X by binding to an active site of USP9X. The compound binding to USP9X according to the present disclosure will, in at least some embodiments, have a $K_D$ value of $1.0 \times 10^{-6}$ mol/l or lower at 25° C., in one embodiment a $K_D$ value of $1.0 \times 10^{-6}$ mol/l or lower at 25° C., in another embodiment a $K_D$ value of $0.5 \times 10^{-6}$ mol/l or lower at 25° C. The binding activity is determined with a standard binding assay, such as a Biacore surface plasmon resonance instrument. A method for determining the $K_D$ value of binding is described in the Examples Section. The binding affinity $K_D$ is determined using a Biacore T200 instrument (GE Healthcare, Biacore). Ubiquitin aldehyde can be used as a reference in analyzing the inhibition results determined via Biacore. Ubiquitin aldehyde is a potent inhibitor of all ubiquitin deconjugating enzymes, including UCHs (ubiquitin C-terminal hydrolases), USPs (ubiquitin-specific proteases) and DUBs (deubiquitinylating enzymes), and binds covalently to the thiol group of the active site Cys of USP9X. In some embodiments, the compounds as disclosed can partially inhibit USP9X. In some embodiments, the compounds as disclosed can partially inhibit USP9X, as compared with the complete inhibition of ubiquitin aldehyde (for example, as shown in FIG. 1E; ubiquitin-aldehyde is an irreversible inhibitor of USP9X, forming a covalent bond with the thiol group of the active site Cys). A partial USP9X inhibition mechanism of the compounds as disclosed is proposed in the present application, which in some embodiments can be evaluated and confirmed by comparing the experimental data of the compounds with the partial inhibition dose-response curve based on the kinetic model of hyperbolic mixed inhibition (for example, as shown in FIG. 1F). The partial inhibition dose-response curve can be generated using the rate equation as shown below:

$$V = V\max \frac{\frac{[S]}{K_S} + \beta[S][I]/aK_SK_I}{1 + \frac{[S]}{K_S} + \frac{[I]}{K_I} + [S][I]/\alpha K_SK_I}, \quad [1]$$

wherein α, β, $K_I$, $K_S$ values can be determined from the experimental data for each compound (as described herein in Example 2).

As used herein, the term "$IC_{50}$" or "the half maximal inhibitory concentration" is used as a measure of the potency of an inhibitor in inhibiting a specific biological or biochemical function. $IC_{50}$ is a quantitative measure that indicates how much of a particular inhibitor is needed to inhibit, in vitro, a given biological process or biological component by 50%. In some embodiments, the biological component is a DUB, especially a USP9X. $IC_{50}$ values are typically expressed as molar concentration. In some embodiments, the term "$IC_{50}$" and "potency" can be used interchangeably.

In some embodiments, the compounds as disclosed have a $IC_{50}$ value from 0.001 to 10 µM. In some embodiments, the compounds as disclosed have a $IC_{50}$ value from 0.005 to 10 µM. In some embodiments, the compounds as disclosed have a $IC_{50}$ value from 0.01 to 10 µM. In some embodiments, the compounds as disclosed have a $IC_{50}$ value from 1 to 10 µM. In some embodiments, the compounds as disclosed have a $IC_{50}$ value from 0.001 to 1 µM. In some embodiments, the compounds as disclosed have a $IC_{50}$ value from 0.001 to 0.1 µM. In some embodiments, the compounds as disclosed have a $IC_{50}$ value from 0.001 to 0.01 µM. In some embodiments, the compounds as disclosed have a $IC_{50}$ value from 0.01 to 0.1 µM. In some embodiments, the compounds as disclosed have a $IC_{50}$ value from 0.1 to 1 µM. In some embodiments, the compounds as disclosed have a $IC_{50}$ value higher than 1 µM.

In some embodiments, the compounds as disclosed have lower $IC_{50}$ values than other USP9X inhibitor in multiple cell lines, and such other USP9X inhibitor may be FT709, EOAI3402143, or WP1130 (also called Degrasyn). In some cases, the compounds as disclosed may be about 1- to about 10-fold more potent than other USP9X inhibitor in multiple cell lines. In some cases, the compounds as disclosed may be about 2-fold, 3-fold, about 4-fold, about 5-fold, about 6-fold, about 7-fold, about 8-fold, or about 9-fold more potent than other USP9X inhibitor in multiple cell lines. In some cases, the compounds as disclosed may be about 4-fold more potent than WP1130 in multiple cell lines.

The compounds as disclosed also exhibit a high binding specificity for USP9X. As used herein, "specificity" and "selectivity" are interchangeable and describe the selective inhibition of the compounds towards a particular enzyme and minimal or no detectable influence on other enzymes' enzymatic activities when in contact over a sufficient period of time. In some embodiments, rather than USP9X, the compounds can inhibit one or more homologous enzymes' enzymatic activities by less than 10%. In some embodiments, rather than USP9X, the compounds can inhibit one or more homologous enzymes' enzymatic activities by less than 6%. In some embodiments, rather than USP9X, the compounds can inhibit one or more homologous enzymes' enzymatic activities by less than about 5%, less than about 4%, less than about 3%, less than about 2%, or less than about 1%. In some embodiments, rather than USP9X, the compounds have no detectable effect on one or more homologous enzymes' enzymatic activities, i.e., the compounds inhibit one or more homologous enzymes' enzymatic activities by 0%. Homologous enzymes include other DUBs rather than USP9X. For example, the compounds (such as Compound 5A as shown in Example 2) have no detectable effect on the enzymatic activities on DUBs including, but not limited to, CYLD, USP2, USP5, USP7, USP13, USP25, USP4, and UCH-L3. For example, the compounds (such as Compound 5A as shown in Example 2) have a minimal detectable effect on the enzymatic activities of other DUBs such as, but not limited to, inhibiting USP30's enzymatic activity by less than about 5%, inhibiting USP10's enzymatic activity by less than about 1%, inhibiting USP15's enzymatic activity by less than about 2%, inhibiting VCPIP's enzymatic activity by less than about 3%, and inhibiting UCH-Li's enzymatic activity by less than about 2%. The selectivity of the compound is determined with a standard screening assay, such as screening the compound on a DUB selectivity panel using ubiquitin-AMC.

In some embodiments, the compounds exhibit higher selectivity against USP9X than other USP9X inhibitors, such as EOAI3402143 and WP1130. Besides USP9X, EOAI3402143 also inhibits USP9X, USP24, and USP5; while WP1130 also inhibits USP5, USP14, UCH-1L, and UCH37.

Methods disclosed herein include methods of treating a disorder, such as a disorder associated with DUB activity or a disorder affected by modulation of DUB activity, or use of a compound disclosed herein in the preparation of a medicament to treat a disorder associated with DUB activity and/or affected by modulation of DUB activity. Further contemplated are methods of treatment wherein DUB catalytic activity is inhibited. In some cases, provided herein are methods that further include identifying a subject having a disorder affected by modulation of activity of a DUB and administering to the subject a compound as disclosed herein.

In some cases, provided herein are methods of inhibiting proliferation of a cell comprising contacting the cell with an effective amount of a compound as disclosed herein to inhibit cell proliferation. In some cases, the cell is a cancer cell. Cancer cells contemplated are described elsewhere herein. In various cases, the compound inhibits a DUB endogenous to the cell and inhibits proliferation. In some cases, provided herein are methods of inhibiting Usp9x.

In some cases, provided herein are methods of treating, inhibiting, or suppressing cancer in a subject, comprising administrating to the subject an effective amount of a compound as disclosed herein to inhibit cancer cell proliferation, thereby treating, inhibiting, or suppressing cancer. Cancer contemplated are described elsewhere herein.

In various cases, the methods provided herein are prophylactic methods, and a compound or composition as disclosed herein is administered prior to onset of a disorder. In certain cases, the method further comprises identifying a subject at risk of contracting a disorder associated with DUB activity and/or affected by DUB modulation (e.g., a virus, bacterium, and/or parasite as disclosed herein), and administering an effective amount of a compound as disclosed herein.

In some cases, provided herein are methods of treating neuropathic or inflammatory pain comprising contacting a cell with a compound disclosed herein in an amount sufficient to reduce or alleviate the pain, or to inhibit Usp5 in the cell. In some cases, the contacting comprises administering the compound to a subject suffering from neuropathic or inflammatory pain.

In some cases, the methods disclosed herein further comprises administering a second therapeutic agent. The second therapeutic agent can be administered at the same time as the compound as disclosed herein, or at a different time (e.g., separated by a time period of about 1 hour to about 12 hours). In cases where the agents are administered at the same time, the agents can be co-formulated, or formulated in separate formulations but given at the same time or within about 30 minutes of each other. Contemplated second agents include, e.g., an antiviral, antiparasitic, antibacterial, anticancer agent, agent that treats one or more symptoms of a genetic disorder, and/or an agent that treats a neurodegenerative disorder.

Cancer

Cancer is a disease of the genome characterized by a diverse mutational landscape and genomic alterations that give rise to mutations that lead to abnormal cell transduction cascades. Signal transduction cascades relay growth signals from the cell membrane into the nucleus to initiate transcriptional responses or post-translational protein modifications. Dysregulation of signal transduction cascades in cancer ultimately results in increased cell survival and abnormal cell proliferation. Signal transduction cascades can be regulated by phosphorylation that controls protein function, and ubiquitination that regulates protein turnover and degradation.

Phosphorylation or kinase signaling cascades and the proteasome, a protein complex involved in ubiquitin mediated protein degradation, are major targets in cancer therapy. The anticancer activity of kinase and proteasome inhibitors arise from the disruption of multiple signaling pathways that support the growth, proliferation, and survival of malignant cells.

In addition to chemotherapy and autologous stem-cell transplantation, current therapy for hematologic (B cell) cancers such as multiple myeloma (MM), mantle cell lymphoma (MCL) and chronic myeloid leukemia include the use of proteasome inhibitors (bortezomib, carfilzomib), immunomodulatory drugs (thalidomide, lenalidomide, pomalidomide) and inhibitors of kinase signal transduction cascades involved in B cell signaling (Btk, mTOR inhibitors). Although current treatment strategies for MM and MCL have improved management and overall survival of patients, the diseases remain incurable with a significant number of patients that eventually relapse and succumb to these diseases and emphasizing the need for more effective therapies.

Ubiquitin/proteasome-mediated protein degradation is one of the major mechanisms used by cells for protein turnover or degradation. It involves two successive steps: 1) the attachment of ubiquitin 76 amino acid polypeptide, to a protein substrate mediated by the ubiquitin activating, conjugating and ligating enzymes E1, E2, and E3, and 2) the degradation of the tagged or poly-ubiquitinylated protein by the 26s proteasome complex or lysosome. (Oncogene (2012) 31, 2373-2388 and Acta Pharmacol Sin 2007 September; 28 (9): 1325-1330).

Deubiquitylation is a reversible process where ubiquitin can be removed from ubiquitinylated proteins by an enzymatic reaction catalyzed by deubiquitinases (DUB). Deubiquitinating enzymes are known to have important roles in the regulation of protein stability, proofreading of protein ubiquitination, recycling of ubiquitin and, maintaining free ubiquitin concentrations. DUBs can enhance protein stability by preventing protein degradation.

Consistent with the role of ubiquitination and DUBs in protein turnover and stability, dysregulation in the activity and expression of these enzymes have been linked to cancer development and progression. Due to their role in stabilizing the expression of oncogenic or tumor suppressor proteins, DUBs have been a focus of attention as drug targets or as diagnostic and prognostic biomarkers in oncology research. Several mutated DUBs have been found to act as oncogenes or tumor suppressors, and changes in the expression levels of DUBs were found in several hematologic and malignant solid tumors (lung, pancreas, prostate, colon, thyroid and breast). (Annu Rev Biochem. 2009; 78:363-97).

The DUB USP9X has recently received considerable attention as potential therapeutic target in several B cell malignancies (MM, MCL, chronic myeloid leukemia) based on the ability of USP9X to associate and stabilize the expression of the oncogenic protein Myeloid cell leukemia-1 (Mcl-1). (Nature. 2010 Jan. 7; 463(7277):103-7) The Mcl-1 protein is known to promote tumor growth and survival by inhibiting apoptotic or cell death pathways. Mcl-1 is overexpressed in MM, MCL and chronic myeloid leukemia. The Mcl-I gene was found to be amplified in 10.9% of cancers across multiple tissue types including breast, lung, skin (melanoma), neural tissue and sarcoma. (Nature. 2010 Feb. 18; 463(7283):899-905). In MM, protein expression levels of Mcl-1 correlate with resistance to chemotherapy, disease relapse and poor survival. Similarly, high expression levels of USP9X were also found in MCL and MM which may be an underlying mechanism of increased Mcl-1 stability in these diseases. The removal of ubiquitin from Mcl-1 by USP9X rescues it from proteasomal degradation and helps promote high levels of Mcl-1 inside of cells. Higher levels of intracellular Mcl-1 helps confer resistance to apoptosis, which is a known hallmark of cancer cells. In theory, any inducement of lower levels of intracellular Mcl-1 renders may render cell more susceptible to apoptosis, especially in response to standard chemotherapeutic agents. In support of this, knocking down USP9X expression in MM and MCL cells reduced Mcl-I levels, reduced MM cell survival and blocked cell proliferation. (Leukemia. 2005 July; 19(7): 1248-52).

Also, degradation of Mcl-1 via inhibition of USP9X can also be used in preparation for stem cell transplant for cancer patients. In current practice, prior to the transplant, patients are treated with a debilitating dose of chemotherapy and/or radiation to ablate hematopoietic cells. Since this stem cell population seems to uniquely dependent upon Mcl-1 for viability, USP9X inhibition may provide a milder and more specific protocol for achieving the same result. One of the concerns about any therapeutic strategy that antagonizes Mcl-1 as a cancer treatment is the attendant toxicity for normal cells. In order to curtail unwanted toxicity, the compounds of the invention may be conjugated to an antibody directed against a surface antigen (e.g., CD34) specific for these stem cells.

Mutations in USP9X gene and high USP9X protein expression were also found in colorectal, breast, lung ovarian and non-small cell lung carcinoma. (Acta Pharmacol. Sin 2007 28(9): 1325-1330). Inhibiting expression of USP9X in MM and colorectal cancer increased cell death, blocked cell proliferation and sensitized cells to chemotherapy suggesting an important role of USP9X in cancer pathology. (Nature, 2010, 463(7283):899-905 and Cancer Biol. Ther. 2012 November; 13(13):1319-24).

USP9X was also found to be overexpressed in melanoma cells and in melanoma patients. The use of compounds in melanoma cell lines resulted in the increased expression of the tumor suppressor p53, reduction in Mcl-1 protein, increased cell death, suppression of tumor cell invasiveness, and inhibition of cell proliferation. The compound also enhanced and further increased the apoptotic and anti-cell proliferation effect of the kinase inhibitor vemurafenib that was recently used in about.60% of melanoma patients that harbor a mutation in BRAF, a component of kinase signaling cascade involved in cell proliferation and survival. In melanoma xenografts, use of monotherapy reduced tumor growth and did not have any notable side effects in animal weight, behavior and mobility.

Meanwhile, USP9X is implicated in regulating endocytosis of the breast cancer oncogene ERBB2. The human protein erbB2 encoded by ERBB2 is also called HER2 (human epidermal growth factor receptor 2) or CD340 (cluster of differentiation 340). In SK-BR3 breast cancer cells overexpressing erbB2 treated with the proteasome inhibitor bortezomib, erbB2 co-immunoprecipitates with a complex containing c-Cbl and USP9X. Reduction in USP9X levels increases bortezomib-induced downregulation of erbB2, suggesting that USP9X is associated with the internalisation and ubiquitylation status of erbB2. (Marx C et al., Cancer Res., 2010; 70:3709-3717).

Overexpression of erbB2 is observed in breast and ovarian cancers (Slamon et al., Science, 1987, 235:177-182; Slamon et al., Science, 1989, 244:707-712; and U.S. Pat. No. 4,968,603), and in other carcinomas including carcinomas of the stomach, endometrium, salivary gland, lung, kidney, colon, thyroid, pancreas and bladder. (King et al., Science, 1985, 229: 974; Yokota et al., Lancet, 1986, 1:765-767; Fukushige et al., Mol Cell Biol., 1986, 6:955-958; Guerin et al., Oncogene Res., 1988, 3:21-31; Cohen et al., Oncogene, 1989, 4:81 88; Yonemura et al., Cancer Res., 1991, 51:1 034:1 034; Borst et al., Gynecol. Oncol., 1990, 38: 364; Weiner et al., Cancer Res., 1990, 50:421-425; Kern et al., Cancer Res., 1990, 50:5 184; Park et al., Cancer Res., 1989, 49:6 605; Zhau et al., Mol. Carcinog., 1990, 3:254-257; Aasland et al. Br. J. Cancer, 1988, 57:358-363; Williams et al. Pathobiology, 1991, 59:46-52; and McCann et al., Cancer, 1990, 65:88-92). Also, erbB2 may be overexpressed in prostate cancer (Gu et al. Cancer Lett., 1996, 99:185-189; Ross et al. Hum. Pathol., 1997, 28:827-33; Ross et al. Cancer, 1997, 79:2162-70; and Sadasivan et al. J. Urol., 1993, 150:126-31). Specific cancers contemplated include, but are not limited to, chronic myelogenous leukemia (CML), melanoma, acute lymphocytic leukemia, chronic lymphocytic leukemia, acute myelogenous leukemia, B-cell lymphoma, mantle cell lymphoma, multiple myeloma, plasma cell dyscrasia, myeloproliferative disorders, glioblastoma, Kapsi's sarcoma, nasopharyngeal carcinoma (EBV), lung cancer, colon cancer, pancreatic cancer, breast cancer, prostate cancer, melanoma, and solid tumors.

The sensitivities of multiple cancer cells can be determined by screening the compounds on a cancer cell line panel, such as an ONCOLINES™ Profiler (Netherlands Translational Research Center) assayed with various tumor cell lines. For more information on ONCOLINES™ methods, see https://www.oncolines.com/oncolines/oncolines-explained-facts/. In some embodiments wherein the ONCOLINES™ Profiler is used, the compounds inhibit the proliferation of a majority of the tumor cell lines being tested, such as at least about 80% of the tumor cell lines being tested or at least 50 of 66 tumor cell lines being tested. For example, Compound 7A inhibited the proliferation of 57 of the 66 cell lines being tested. For a tumor cell line sensitive to the compounds, the compounds can have a $IC_{50}$ value of no greater than 1 µM. "A tumor cell line sensitive to the compounds" is referred to that the proliferation of a tumor cell line, when contacted with the compounds, is inhibited by at least 50%, at least 60%, at least 70%, at least 80%, at least 85%, at least 90%, at least 91%, at least 92%, at least 93%, at least 94%, at least 95%, at least 96%, at least 97%, at least 98%, at least 99%, or 100%.

Any cancer cell associated with high expression of one or more USP9X substrates, such as Mcl-1 and/or erbB2, can be used as a therapeutic target for the compounds as disclosed. As a nonlimiting example, cancer cell line completed may include the colon carcinoma cell line RKO (that expresses high levels of Bcl-2 and very high levels of Mcl-1 but is resistant to the Bcl-2 and Bcl-xl inhibitor ABT737), the pancreatic cancer cell line MiaPaca-2 (that has mutations in both copies of Ras gene and over expresses erbB2 and Mcl-1), the human breast cancer cell line SK-BR3 (that expresses erbB2 and Mcl-1 and is especially used in erbB2 targeting), the human breast ductal carcinoma cell line BT-549, the triple-negative breast cancer (TNBC) cell line MDA-MB-231, and the histiocytic lymphoma cell line U937.

In some embodiments, the induced degradations of USP9X substrates (such as Mcl-1, erbB2, beta-catenin and aldehyde dehydrogenase 1A3) in multiple cancer cell lines by the compounds, can be investigated using a standard analysis method, such as western blot, flow cytometry, or ELISA. After treated with the compounds for a certain period of time (e.g., from about 1 hour to about 72 hours, such as 12, 24, 48, and 72 hours and preferably 72 hours), the normalized signals from USP9X substrates, especially Mcl-1 and/or erbB2, decrease by at least 40%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, indicating that the compounds induce the substrate degradation by inhibiting USP9X. The induced degradation leads to the inhibition of cancer cell proliferation, resulting in the decrease in cell viability. In particular embodiments, even partial degradation of the substrates induced by the compounds can be sufficient to inhibit the proliferation of cancer cells completely, such as disclosed in Example 3 wherein the 50% decrease in Mcl-1 due to the 24-hour treatment of the compound led to the inhibition the U937 cell proliferation by 100% (i.e., cell viability decreases to 0%).

The mechanism of action for induced degradation of USP9X substrate can be further examined by comparing the combined effect of the compound and a proteasome inhibitor with the effect of the compound alone, on cells that express the USP9X substrate. As illustrated in Example 4, when U937 cells treated with both MG132 and Compound 5A, decline in Mcl-1 was reduced compared to U937 cells treated with Compound 5A only. These results confirmed intracellular inhibition of USP9X by the compounds to enhance proteasomal degradation of Mcl-1. By varying the concentration ratios of the compound and proteasome inhibitor for treating cells, it is possible to control the degradation of a USP9X substrate so the USP9X substrate can decline to a desirable level rather than degrade entirely. The combined use of the compound and proteasome inhibitor provides a novel approach for inducing controlled degradation of a USP9X substrate wherein the USP9X substrate declines by about 10% or more, about 20% or more, about 30% or more, about 40% or more, about 50% or more, about 60% or more, about 70% or more, about 80% or more, about 90% or more.

Immune Oncology Programmed death-ligand 1 (PD-L1), an immune-oncology target, has been recently identified as a substrate for USP9X. PD-L1 as a transmembrane protein is expressed on tumor cells and capable of blunting the immune response to tumors by interacting with PD1 on the surface of T cells that otherwise would attack tumor antigens on the surface of these cells and eradicate them. The PDL1-PD1 interaction can be blunted by therapeutic antibodies and has shown clinical benefit in cancer patients. The compounds as described herein may be capable of inducing PD-L1 degradation by inhibiting USP9X and thus enhancing the immune response of T cells against tumor cells. People skilled in the art will recognize that other USP9X substrates, have been described and are continually being discovered. All such USP9X substrates can be therapeutic, prognostic, or research targets of the compounds as described herein and encompassed by the present invention.

Pathogenic Infections

The methods and compounds disclosed herein are useful in treating pathogenic infections, e.g., preventing, inhibiting and/or ameliorating a pathogenic infection or symptom of a pathogenic infection. In some cases, the methods and compounds disclosed herein are useful in treating a condition due to a pathogenic infection.

Intentional contamination of the food and water supplies represents a major threat to the health and health-related services in the US population as a whole and to our armed forces serving throughout the world. Many of the category B water- and food-borne pathogens have specific properties, e.g. low infectious dose, high stability, that make them attractive candidates for this type of bioterrorism. To thwart this potential threat, methods or agents that provide protection or prophylaxis against these defined pathogens are urgently needed. Ideally, agents that provide protection against a wide spectrum of threats would be desirable. The compounds disclosed herein have broad activity against multiple pathogens. For example, a potent inhibitor of diverse category A and B pathogens, and related family members, e.g., murine norovirus, Tulane virus, *Listeria monocytogenes, Toxoplasma gondii* infection. Norwalk virus, Sindbis virus, La Crosse virus and coronavirus, such as SARS, MERS, COVID-19. COVID-19 replication requires deubiquitylase activity.

In certain cells the compounds disclosed herein inhibit a deubiquitinase and this action results in accumulation of ubiquitinated proteins in the cytoplasmic and aggresomal compartment of the cell. This can establish an inhospitable environment for pathogen infection or replication within the target cell. Thus, these compounds are used as an antimicrobial inhibitor that can effectively suppress multiple pathogens. The compounds disclosed herein block the infectivity of category A and/or B pathogens, and/or related family members.

Contemplated are pathogens that use a DUB in their infection mechanism. In some cases, the pathogen uses a DUB endogenous to the infected cell. In various cases, the pathogen uses a DUB endogenous to the pathogen.

Contemplated diseases or disorders due to a pathogenic infection include gastroenteritis, encephalitis, respiratory tract infections (e.g., SARS), virus-induced cancers, rabies, hemorrhagic fevers (e.g., Crimean-Congo, Dengue), Rift valley fever, listeriosis, or toxoplasmosis. Also contemplated diseases or disorders due to a pathogenic infection include meningitis, myocarditis, hepatitis, bacteremia, and skin infections.

Contemplated pathogens include viral, bacterial, fungal, and parasitic pathogens. Contemplated pathogenic viruses include a calicivirus (e.g., norovirus, sapovirus), a picornavirus, a Togavirus, a Bunyavirus, a Rhabdovirus, a herpes virus, an adenovirus, an arterivirus, a coronavirus, a flavivirus, a paramyxovirus, a papillomavirus, a virus encoding for an ovarian tumor (OTU)-like protease, a baculovirus, or a nairovirus. Other contemplated pathogenic viruses include polyoma viruses and retroviruses.

Specific viruses contemplated include encephalomyocarditis virus (EMCV), Sindbis virus (SiNV), La Crosse virus (LaCV), Norwalk virus, Tulane virus, rotavirus, Epstein-Barr (EBV), herpesvirus, Dengue virus, and papillomavirus. Further specific viruses contemplated include cytomegalovirus, BK virus, hepatitis C virus, and HIV.

Contemplated bacteria include *Chlamydia, Escherichia, Salmonella, Yersinia, Burkholderia, Haemophilus, Listeria,* and *Mycobacterium*. Other bacteria contemplated include *Staphylococcus aureus*, or more specifically methicillin-resistant Staph *aureus* (MRSA).

Contemplated parasites or fungi include *Plasmodium falciparum, Toxoplasma gondii, Entamoeba histolytica, Giardia lamblia, Trypanosoma brucei, Trypanosoma cruzi,* Cestoda, *Clonorchis, Opisthorchis, Strongylocides, Candida, Aspergillus,* and *Cryptococcus*.

Dosing and Pharmaceutical Formulations

The terms "therapeutically effective amount" and "prophylactically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Dosages of the therapeutic can alternately be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

As herein, the compounds described herein may be formulated in pharmaceutical compositions with a pharmaceutically acceptable excipient, carrier, or diluent. The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However, the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose, any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of alpha-, beta-, and gamma-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Combination Therapy

The methods of the embodiments also include the use of a compound or compounds as described herein together with one or more additional therapeutic agents for the treatment of disease conditions. Thus, for example, the combination of active ingredients may be: (1) conjugated, (2) co-formulated and administered or delivered simultaneously in a combined formulation; (3) delivered by alternation or in parallel as separate formulations; or (4) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In some cases, a compound disclosed herein is administered and/or formulated with a second therapeutic—e.g., a chemotherapeutic.

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphor-amide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actinomycin D, daunomycin (rubidomycin), doxorubicin, mitoxantrone, idarubicin, bleomycins, plicamycin (mithramycin), mitomycin C, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, Stat inhibitors, and nanoparticles.

Protein and antibody chemotherapeutics are well suited for combination therapies and/or chemical conjugation to the compounds of the invention. For example, the combination therapy can include aldesleukin (e.g., PROLEUKIN), alemtuzumab (e.g., CAMPATH), asparaginase *Erwinia chrysanthemi* (e.g., ERWINAZE), bevacizumab (e.g., AVASTIN), blinatumomab (e.g., BLINCYTO), brentuximab vedotin (e.g., ADCETRIS), cetuximab (e.g., ERBITUX), denosumab (e.g., PROLIA, XGEVA), Dinutuximab (e.g., UNITUXIN), ibritumomab tiuxctan (e.g., ZEVALIN), ipilimumab (e.g., YERVOY), leuprolide acetate (e.g., LUPRON DEPOT, LUPRON DEPOT-3 MONTH, LUPRON DEPOT-4 MONTH, LUPRON DEPOT-PED, LUPRON, VIADUR), nivolumab (e.g., OPDIVO), obinutuzumab (e.g., GAZYVA), OEPA, ofatumumab (e.g., ARZERRA), panitumumab (e.g., VECTIBIX), pegaspargase (e.g., ONCASPAR), peginterferon alfa-2b (e.g., PEG-INTRON), peginterferon alia-2b (e.g., SYLATRON), pembrolizumab (e.g., KEYTRUDA), ramucirumab (e.g., CYRAMZA), R-CHOP, recombinant HPV bivalent vaccine (e.g., CERVARIX), recombinant human papillomavirus (e.g., HPV) nonavalent vaccine (e.g., GARDASIL 9), recombinant human papillomavirus (e.g., HPV) quadravalent vaccine (e.g., GARDASIL), recombinant interferon alfa-2b (e.g., INTRON A), rituximab (e.g., RITUXAN), siltuximab (e.g., SYLVANT), tositumomab and iodine 1 131 tositumomab (e.g., BEXXAR), and trastuzumab (e.g., HERCEPTIN).

Conjugation can be achieved by covalently reacting a moiety on the conjugate or protein and a moiety substituted on the compound of formula (I). For example, the compound of formula (I) can be substituted by an attachment group, such as an electrophilic group or group that can react with a crosslinking agent. For example, conjugation moieties include thiols, hydroxy groups and amines. For example, maleimide groups, activated disulfides, active esters such as NHS esters and HOBt esters, haloformates, acid halides, alkyl and benzyl halides such as haloacetamides can be used. Self-stabilizing maleimides and bridging disulfides can also be used in accordance with the disclosure.

One example of a "self-stabilizing" maleimide group that hydrolyzes spontaneously under antibody conjugation conditions to give an ADC species with improved stability is depicted in the schematic below. See U.S. Published Application No. 2013/0309256, International Application Publication No. WO 2013/173337, Tumey et al., 2014, Bioconjugate Chem. 25: 1871-1880, and Lyon et al., 2014, Nat. Biotechnol. 32: 1059-1062. Thus, the maleimide attachment group is reacted with a sulfhydryl of an antibody to give an intermediate succinimide ring. The hydrolyzed form of the attachment group is resistant to deconjugation in the presence of plasma proteins. Other crosslinking moieties such as epichlorohydrin can also be used.

Also using conjugation technology, targeting agents, such as, peptides, proteins, small molecules, antibodies or ligands specific to cell receptors, can be linked to a compound of the invention. For example, the compounds as described can be incorporated into PROTAC constructs to target USP9X, leading to its ubiquitylation by an E3 ubiquitin ligase and consequently inducing the degradation of USP9X For example, cell receptors on cancer cells can be targeted. For example, antibodies or ligands that bind one of the following antigens can be used: Aminopeptidase N (CD13), Annexin A1, B7-H3 (CD276, various cancers), CA125, CA15-3 (carcinomas), CA19-9 (carcinomas), L6 (carcinomas), Lewis Y (carcinomas), Lewis X (carcinomas), alpha fetoprotein (carcinomas), CA242, placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30, CD33, CD38 (multiple myeloma), CD40 (lymphoma, multiple myeloma, leukemia), CD51 (Metastatic melanoma, sarcoma), CD52, CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL4 (.DELTA.-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glycolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, $R_4$, Castleman's disease, IL6 dependent tumors), Integrins (.alpha.v.beta.3, .alpha.5.beta.1, .alpha-.'.beta.4, alpha.11.beta.3, .alpha.5.beta.5, .alpha.v.beta.5, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumor associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, $R_A$ and SLE), TPBG (trophoblast glycoprotein, Renal cell carcinoma), TRAIL-R1 (Tumor necrosis apoptosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-253 (2009); Novellino et al, Cancer Immunol Immunother. 54(3), 187-207 (2005). Franke, et al, Cancer Biother Radiopharm. 2000, 15, 459-76). Many other antigens are: many other Cluster of Differentiations (CD4, CD5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD79a, CD79b, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), Apo2, ASLG659, BMPR1B (bone morphogenetic protein receptor), CRIPTO, Annexin A1, Nucleolin, Endoglin (CD105), ROBO4, Amino-peptidase N, .DELTA.-like-4 (DLL4), VEGFR-2 (CD309), CXCR4 9CD184), Tie2, B7-H3, WT1, MUC1, LMP2, HPV E6 E7, EGFRvIII, HER-2/neu, Idiotype, MAGE A3, p53 nonmutant, NY-ESO-1, GD2, CEA, MelanA/MART1, Napi3b (NAPI-3B, NPTIIb, SLC34A2, solute carrier family 34, member 2, type II sodium-dependent phosphate transporter 3b), Ras mutant, gp100, p53 mutant, Proteinase3 (PR1), bcr-abl, Tetratocarcinoma-derived growth factors), EphA receptors, EphB receptors, EGFr, EGFRvIII, ETBR (Endothelin), HER2/neu, HER3, HLA-DOB (MHC class II molecule Ia antigen), integrins, IRTA2, MPF (MPF, MSLN, SMR, megakaryocyte potentiating factor, mesothelin), cripto, Sema 5b (FLJ10372, KIAA1445, Mm42015, SEMA5B, 5EMAG, semaphoring 5 bHlog, sdema domain, seven thrombospondin repeats, cytoplasmic domain), PSCA, STEAPI (six transmembrane epithelial antigen of prostate), and STEAP2 (HGNC 8639, IPCA-1, PCANP1, STAMPI, STEAP2, STMP, prostate) Tyrosinase, Survivin, hTERT, Sarcoma translocation breakpoints, EphA2, PAP, ML-IAP, AFP, EpCAM, ERG (TM-PRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-.beta., MAD-CT-2, Fos-related antigen 1.

Targeting agents that can target cells implicated in autoimmune diseases include: anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-p62 antibody; Anti-sp100 antibody; Anti-Mitochondrial (M2) antibody; Rheumatoid factor antibody; Anti-MCV antibody; Anti-topoisomerase antibody; Anti-neutrophil cytoplasmic (cANCA) antibody.

Targeting agents for infectious diseases include antibodies that bind pathogens, such as Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae (including COVID-19 such as targeting—the so-called spike protein), Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis), HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytial virus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

Controlling Degradation of USP9X Substrates

Provided herein is also a method of controlling induced degradation of a USP9X substrate in a cell by co-treating the cell with an effective amount of a proteasome inhibitor and an effective amount of the compound as disclosed. In some embodiments, the ratio of the proteasome inhibitor and the compound may be selected from any values between 0.01 and 100, preferably, between 0.1 and 10. The proteasome inhibitor used herein may be, as a nonlimiting example, MG132. In some embodiments, the USP9X substrate is Mcl-1. In some embodiments, the induced degradation can be controlled to reach a desirable level, at which, for example, the USP9X substrate declines by about 10% or more, about 20% or more, about 30% or more, about 40% or more, about 50% or more, about 60% or more, about 70% or more, about 80% or more, or about 90% or more.

The proteasome inhibitor MG132 has been frequently used as a laboratory research tool to examine the consequences of blocking the ubiquitin-proteasome pathway. For clinical use, MG132 has been modified (by introducing a boronate group to the peptide backbone) to yield the proteasome inhibitor bortezomib which is marketed as Velcade. A proteasome inhibitor drug such as Velcade may take antagonistic action against a drug of the compounds as described. In some embodiments, provided may also be methods of treating a subject with a condition by co-administering the compounds as described and subsequently a proteasome inhibitor drug (such as Velcade) to the subject, wherein a USP9X substrate (preferably Mcl-1) in a cell of the subject is induced to degrade by the drug of the compounds as described and the induced degradation is controlled, slowed down, or terminated by the proteasome inhibitor drug.

Combination Therapy with Other Inhibitors

The USP9X substrate Mcl-1 may serve as an anti-apoptotic factor conferring resistance to chemotherapy, e.g., providing protection for other pathologic proteins against their inhibitors. These pathologic proteins may be an over-expressed anti-apoptotic protein such as, but are not limited to, Bcl-2 and Bcl-xL.

ABT737 is a prototype of new class of anti-cancer drugs known as BH3 mimetics, such as Navitoclax or Venetoclax. This class of drugs functions by antagonizing the action of anti-apoptotic proteins such as Bcl2, Bcl-xL, and Mcl-1 by blocking their ability to prevent the activation of pro-apoptotic proteins such as Bak and Bax. ABT737 is a small molecule that binds to Bcl2 and Bcl-xL but not Mcl-1. The binding site for ABT737 on Bcl2 and Bcl-xL is the same surface groove employed by Bcl2 and Bcl-xL to bind the BH3 domains of pro-apoptotic proteins culminating in the activation of Bak and Bax, the permeabilization of the outer membrane of the mitochondrion and the activation of caspases to dismantle the cell. Treatment of cancer cells with ABT737 alone, may induce apoptosis but only if the intracellular level of Mcl-1 is low enough. This suggests that treatment of ABT737-resistant cells with USP9X inhibitors may augment the cell killing potential of ABT737 and similar compounds.

Provided herein is a method of inhibiting a cancer cell expressing Mcl-1 and at least one other anti-apoptotic Bcl-2 family protein, by co-treating the cell with an effective amount of the compound as disclosed and an effective amount of the Bcl-2 family inhibitor. The at least one other anti-apoptotic Bcl-2 family protein may be Bcl-2, Bcl-xL, or both Bcl-2 and Bcl-xL. The cancer cell may be selected from, but not limited to, acute myeloid leukemia (AML) cell and breast cancer cell. In some embodiments, the Bcl-2 family inhibitor is a Bcl-2/Bcl-xL inhibitor, such as ABT737, Navitoclax or Venetoclax. Provided herein is also a method of sensitizing a cell expressing Mcl-1 and at least one other anti-apoptotic Bcl-2 family protein for a Bcl-2 family inhibitor, by co-treating the cell with an effective amount of the compound as disclosed and an effective amount of the Bcl-2 family inhibitor. The at least one other anti-apoptotic Bcl-2 family protein may be Bcl-2, Bcl-xL, or both Bcl-2 and Bcl-xL. Preferably, the cell is a cancer cell, such as acute myeloid leukemia (AML) cell or breast cancer cell. In some embodiments, the Bcl-2 family inhibitor is a Bcl-2/Bcl-xL inhibitor, such as ABT737, Navitoclax or Venetoclax.

Provided herein is also a method of enhancing potency of a Bcl-2 family inhibitor in a cell expressing Mcl-1 and at least one other anti-apoptotic Bcl-2 family protein, by co-treating the cell with an effective amount of the compound as disclosed and an effective amount of the Bcl-2 family inhibitor. In some embodiments, the potency of the Bcl-2 family inhibitor may be enhanced by about 2 to about 100 folds. In some embodiments, the potency of the Bcl-2 family inhibitor may be enhanced by about 2, about 5, about 10, about 20, about 30, about 40, about 50, about 60, about 70, about 80 folds, or about 90 folds. In some embodiments, the potency of the Bcl-2 family inhibitor may be enhanced by about 50 folds. Preferably, the Bcl-2 family inhibitor is a Bcl-2/Bcl-xL inhibitor, such as ABT737, Navitoclax or Venetoclax.

Provided herein is also a method of treating a condition in a subject wherein the condition is associated with a pathologic cell that expresses Mcl-1 and at least one other anti-apoptotic Bcl-2 family protein, by co-administrating to the subject an effective amount of a pharmaceutical composition of the compound as disclosed and an effective amount of a pharmaceutical composition of a Bcl-2 family inhibitor. In some embodiments, the condition is a cancer, such as acute myeloid leukemia (AML) or breast cancer. In some embodiments, the at least one other anti-apoptotic Bcl-2 family protein may be Bcl-2, Bcl-xL, or both Bcl-2 and Bcl-xL. In some embodiments, the Bcl-2 family inhibitor is a Bcl-2/Bcl-xL inhibitor, such as a clinically acceptable derivative of ABT737 (e.g., Venetoclax and Navitoclax).

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Example 1: Synthesis of Compounds

Materials and Methods

Unless otherwise noted, reagents and solvents were used as purchased from commercial suppliers. Solvent removal was accomplished usually using a rotary evaporator at ~15 mm Hg pressure unless otherwise specified. Thin-layer chromatography (TLC) was performed using silica-gel 60 plates (F254, Merck) and visualized by UV light (254 nm). Column chromatography and flash column chromatography were carried out using silica gel (60-203 mesh and 40-60 mesh, respectively) unless otherwise specified.

Synthetic Route for Compound 7A

Preferred compounds of the invention include:

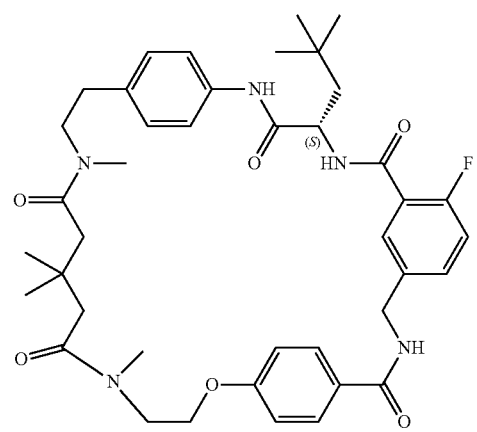

Building block synthesis

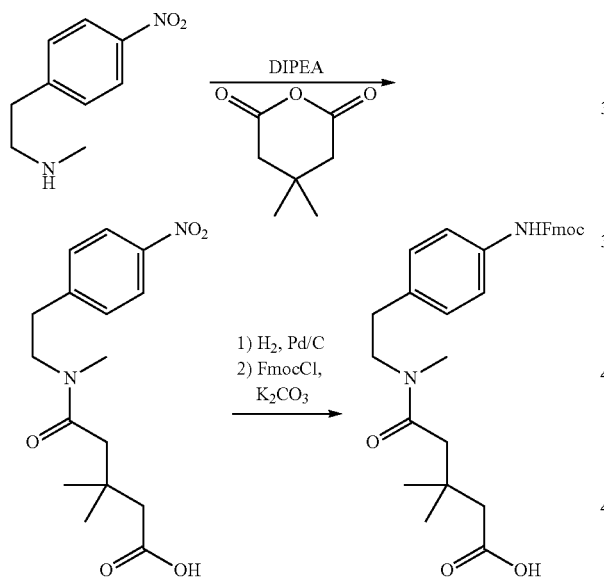

Step 1: N-methyl-2-(4-nitrophenyl)ethan-1-amine hydrochloride (500 mg, 2.3 mmol) was dissolved in DCM (23 mL) before DIEA (2.0 mL, 11.5 mmol) and 4,4-dimethyldihydro-2H-pyran-2,6(3H)-dione (361 mg, 2.5 mmol) were added. The mixture was stirred at room temperature and monitored by LCMS. After 15 min, the reaction complete. The reaction was washed with 1.2N HCl solution and brine, dried over MgSO₄, filtered and concentrated to give 3,3-dimethyl-5-(methyl(4-nitrophenethyl)amino)-5-oxopentanoic acid (616 mg, 83% yield), which was used as is.

Step 2: 3,3-dimethyl-5-(methyl(4-nitrophenethyl)amino)-5-oxopentanoic acid (0.616 g, 1.9 mmol) and 10% Pd/C (0.2 g, 0.19 mmol) were stirred in EtOAc (19 ml) under a hydrogen atmosphere (1 atm). After the reaction was complete as determined by LCMS, the mixture was filtered and concentrated to give 5-((4-aminophenethyl)(methyl)amino)-3,3-dimethyl-5-oxopentanoic acid (0.373 g, 66.8% yield) as a yellow oil, which was used as is.

Step 3: 5-((4-aminophenethyl)(methyl)amino)-3,3-dimethyl-5-oxopentanoic acid (0.373 g, 1.3 mmol) and potassium carbonate (0.212 g, 1.5 mmol) were dissolved in Water (6 ml). The mixture was cooled to 0° C. before a solution of (9H-fluoren-9-yl)methyl carbonochloridate (0.330 g, 1.3 mmol) in acetonitrile (6 ml) was added dropwise. The reaction was warmed to room temperature slowly and monitored by LCMS. After 30 min, the reaction was acidified with 1M HCl and extracted with ether. The combined ether extracts were dried over MgSO₄, filtered and concentrated. Purification by silica gel chromatography gave 5-((4-((((9H-fluoren-9-yl)methoxy)carbonyl)amino)phenethyl)(methyl)amino)-3,3-dimethyl-5-oxopentanoic acid (0.174 g, 26.5% yield) as a white solid.

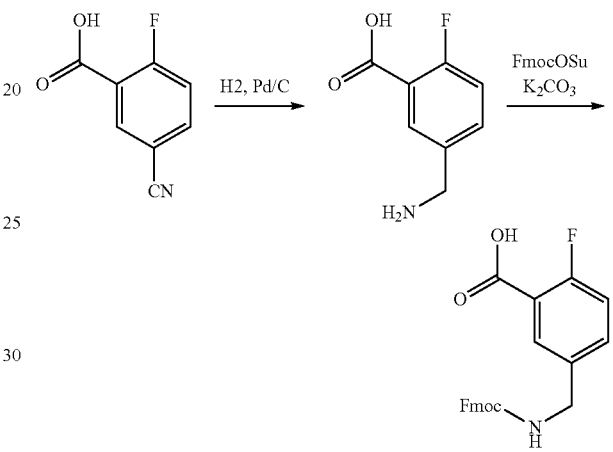

Step 1: 5—Cyano-2-fluorobenzoic acid (3.0 g, 18.3 mmol) and 10% palladium on carbon (0.3 g, 2.7 mmol) were shaken in methanol (200 mL) under a hydrogen atmosphere (20 PSI). After 3 h, the reaction was complete by LCMS. The mixture is filtered and concentrated to give 2.1 g of the desired product (68%), which was used as is.

Step 2: 5-(aminomethyl)-2-fluorobenzoic acid (2 g, 11.8 mmol) and (9H-fluoren-9-yl)methyl (2,5-dioxopyrrolidin-1-yl) carbonate (3.99 g, 11.8 mmol) were dissolved in THF (250 mL). A saturated K₂CO₃ solution was added until the pH was non-acidic. The mixture was stirred at room temperature and monitored by LCMS. After 2 h, the mixture was concentrated and the residue was washed with water and DCM (2×) and dried overnight to give the desired product in >75% yield.

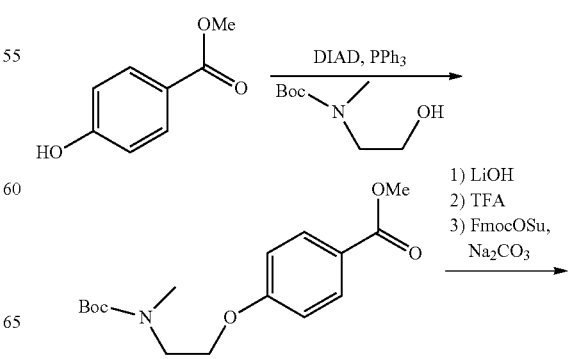

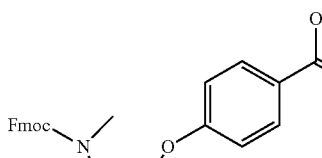

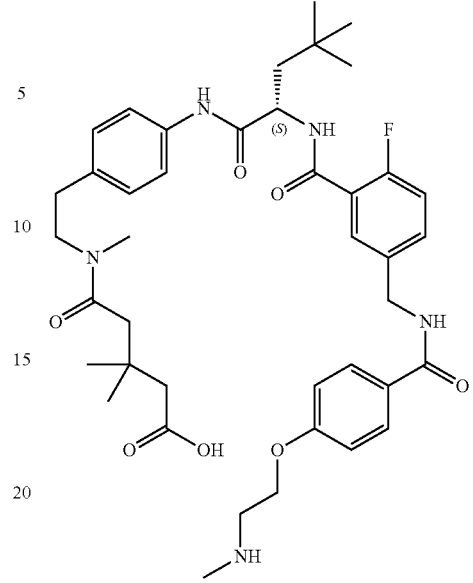

Step 1: Methyl 4-hydroxybenzoate (0.250 g, 1.6 mmol) was dissolved in THF (16 ml) before tert-butyl (2-hydroxyethyl)(methyl)carbamate (0.333 ml, 2.0 mmol) and Ph$_3$P (0.560 g, 2.1 mmol) were added. The reaction was cooled to 0° C. and DIAD (0.383 ml, 2.0 mmol) was added dropwise and the reaction was monitored by LCMS. After 40 min, the reaction was concentrated the crude residue was purified by silica gel chromatography to give 0.440 g (87%) of desired product.

Step 2: 4-Methyl 4-(2-((tert-butoxycarbonyl)(methyl)amino)ethoxy)benzoate (0.440 g, 1.4 mmol) and 1M aqueous LiOH (7.11 ml, 14.2 mmol) were stirred in THF (14 ml) at 60° C. and the reaction was monitored by LCMS. After stirring overnight, the reaction was complete. The mixture was acidified (pH 2-3) with 1M aqueous HCl and extracted with DCM (3×). The combined organic extracts were dried over Na$_2$SO$_4$, filtered and concentrated to give crude 4-(2-((tert-butoxycarbonyl)(methyl)amino)ethoxy)benzoic acid, which was subsequently dissolved in DCM (14 ml) before TFA (2.191 ml, 28.4 mmol) was added. The reaction was stirred at room temperature and monitored by LCMS. After 45 minutes, complete conversion was observed. The mixture was concentrated and then azeotroped with toluene to remove excess TFA. The product, 4-(2-(methylamino)ethoxy)benzoic acid, was dissolved in acetonitrile (11 ml) and water (3.5 ml) before sodium carbonate (0.603 g, 5.7 mmol) was added. Fmoc-OSu (0.504 g, 1.5 mmol) was then added and the reaction stirred at room temperature. After the reaction was complete (1 h), the mixture was acidified (pH 2-3) with 1M aqueous HCl and extracted with DCM (×3). The combined organic extracts were dried over Na$_2$SO$_4$, filtered and concentrated. The crude product was purified by silica gel chromatography to give 515 mg (87% over 3 steps) of the desired product.

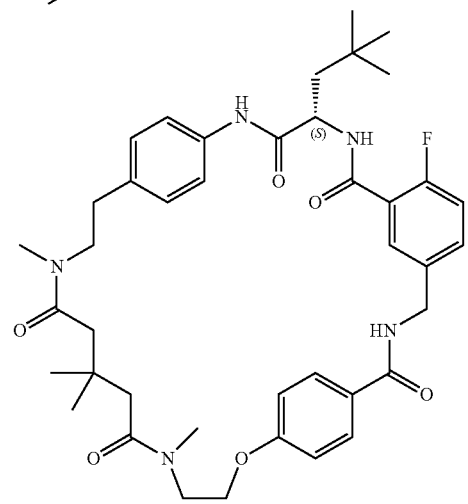

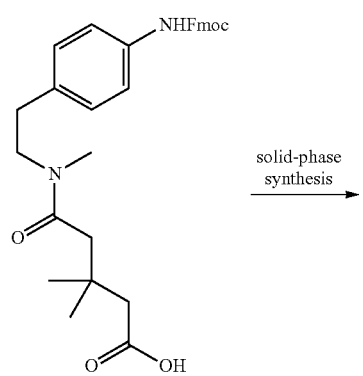

Typical Synthesis of Analogs—

Loading: 2—Chloro-trityl chloride resin (1.2 equiv) was swelled in DCM for 10 min and then filtered and washed with DCM. The appropriate Fmoc protected amino acid (1.0 equiv) and N-ethyl-N-isopropylpropan-2-amine (6.0 equiv) were dissolved in DCM. The resulting solution was added to the swelled resin and agitated for 2 hours. The resin was then washed with 85:10:5 DCM:MeOH:DIPEA (10 mL×3); DCM (10 mL×3), DMF (10 mL×3), DCM (20 mL×3). After flushing with argon and dried under vacuum, compound linked resin was obtained. Solid-phase Fmoc-deprotection-Resin (1.0 equiv) was suspended in DMF (4 mL×5 min) and mixed with a stream of N2 every 30 seconds. The Fmoc group was removed from the resin-supported building block by mixing the resin twice with a solution of 2% DBU, 2% piperidine in DMF (4 mL×5 min) while agitating with a stream of N2 every 30 seconds. The resin was washed six times with DMF (4 mL x 30 sec) and used in the next step as is.

Solid-phase amide formation—The appropriate carboxylic acid (0.1 M solution in DMF, 2 equiv), followed by HATU (0.2M solution in DMF, 2.1 equiv) and N-methyl morpholine (1.0 M in DMF, 6.7 equiv) were added to the resin (1.0 equiv). The reaction mixture was agitated by a stream of nitrogen for 2 hours. The reagents were drained from the reaction vessel, and the resin was washed with six times DMF (4 mL x 30 sec) and used in the next step as is.

Cleavage: Resin (1.0 equiv) was treated with 5% TFA in CH$_2$Cl$_2$ (8 mL×5 min) then washed with DCM (8 mL). This was repeated two more times. Solvent was removed by evaporation using a Genevac EZ2.2 evaporator. The crude reaction mixture was carried on to the next reaction.

Cyclization: Dissolved the linear amino acid (1.0 equiv) in DMF (0.05 M) before N-ethyl-N-isopropylpropan-2-amine (5.0 equiv) was added. The resulting solution was added to a pre-mixed solution of HATU (1.2 equiv) and HOAt (1.2 equiv) in DMF (0.011 M) at ~2 mL/min. The reaction was monitored by LCMS and additional HATU was added until complete conversion to the desired product was observed. The mixture was concentrated and purified by either preparative HPLC (small-scale) or reverse-phase silica gel chromatography to give the desired product.

Synthetic Route for Compound 1A

Synthesis of intermediate A

Preparation of 4,4-Dimethylheptanedioic acid

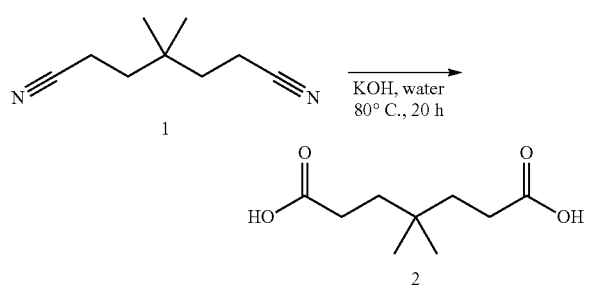

4,4-Dimethylheptanedinitrile (1, 500 mg, 3.3 mmol, 1.0 equiv) was suspended in water (10 mL) and KOH (930 mg, 16.6 mmol, 5.0 equiv) was added. The reaction mixture was stirred at 80° C. for 20 h. The progress of the reaction was monitored by TLC (CHCl$_3$:MeOH=20:1+anisaldehyde) and LCMS analyses. After completion, the mixture was diluted with water and its pH was adjusted to 3-4 by the addition of 2 M aq. HCl solution, then extracted with EtOAc twice. The organic phase was dried over MgSO$_4$, filtered and concentrated in vacuo to obtain 4,4-Dimethylheptanedioic acid.

Preparation of 4,4-Dimethyl-7-(methyl(4-nitrophenethyl)amino)-7-oxoheptanoic acid

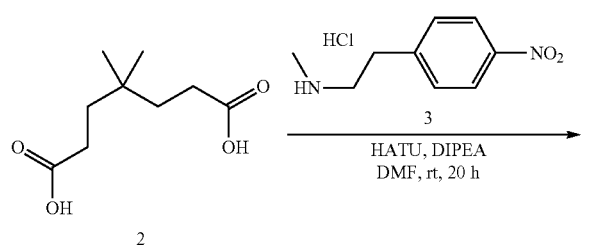

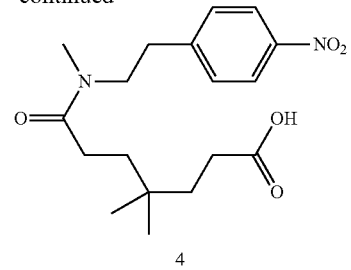

4,4-Dimethylheptanedioic acid (1.1 g, 5.8 mmol, 1.0 equiv) was dissolved in anhydrous DMF (23 mL) then DIPEA (1.9 g, 14.5 mmol, 2.5 equiv) and HATU (1.1 g, 2.9 mmol, 0.5 equiv) were added. The resulting mixture was stirred at rt for 30 min then reagent (3, 630 mg, 2.9 mmol, 0.5 equiv) was added and stirring was continued at rt for 4 h. As no full conversion was detected by TLC and LCMS analyses, another portion of HATU (660 mg, 1.7 mmol, 0.3 equiv) and—after 10 min stirring—reagent (3, 380 mg, 1.7 mmol, 0.3 equiv) were added. The reaction mixture was stirred at rt for 20 h. The progress of the reaction was monitored by TLC (CHCl$_3$:MeOH=5:1+bromocresol green) and LCMS analyses. After completion, the reaction mixture was concentrated in vacuo, the residue was dissolved in EtOAc and washed with 10 w/w % aq. Na$_2$CO$_3$ solution. The pH of the aqueous phase was adjusted to 3-4 by the addition of 1 M aq. HCl solution and extracted with EtOAc twice. The combined organic phase was dried over MgSO$_4$, filtered and concentrated in vacuo. The crude product was purified by column chromatography (eluent: 0 to 10% MeOH in CHCl$_3$) to obtain Compound 4.

Preparation of Ethyl 4,4-dimethyl-7-(methyl(4-nitrophenethyl)amino)-7-oxoheptanoate

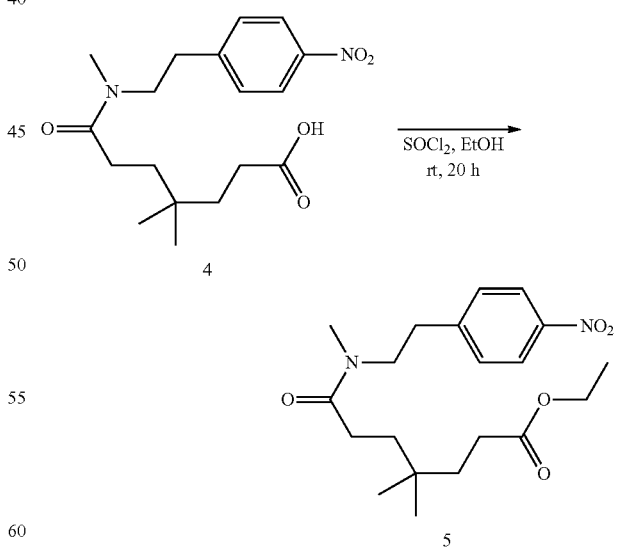

Starting acid compound 4 (1.17 g, 3.34 mmol, 1.0 equiv) was dissolved in EtOH (10 mL) then SOCl$_2$ (1.26 mL, 16.69 mmol, 5.0 equiv) was added. The resultant mixture was stirred at rt for 2 h. The progress of the reaction was monitored by TLC (DCM:MeOH=20:1) and LCMS analyses. After completion, the solvent was evaporated and the residue was taken up in EtOAc and washed with sat. aq. NaHCO₃ solution. The organic phase was dried over MgSO₄, filtered and concentrated under reduced pressure to obtain the crude product 5, which was used as is.

Preparation of Ethyl 7-((4-aminophenethyl)(methyl)amino)-4,4-dimethyl-7-oxoheptanoate

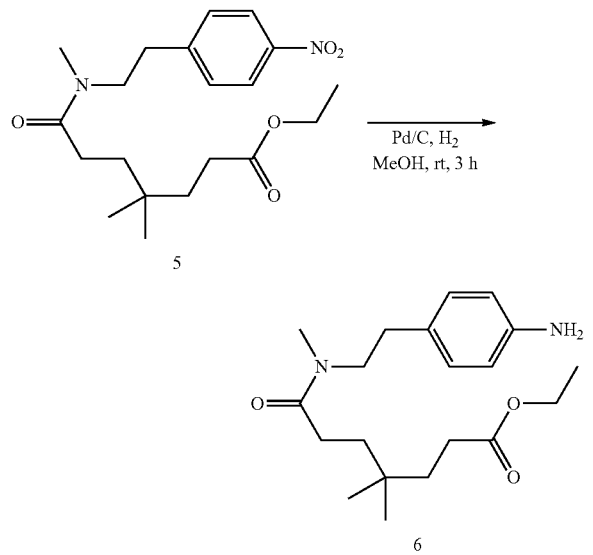

Starting compound 5 (829 mg, 2.19 mmol, 1.0 equiv) was dissolved in EtOH (22 mL) then Pd/C (10% Pd on C, 82.9 mg, 0.078 mmol, 0.036 equiv) was added. The vessel was closed, purged with argon then pressurized with 3 bar H₂ and stirred at rt for 5 h. The progress of the reaction was monitored by TLC (CHCl₃:MeOH=20:1) and LCMS analyses. After completion, the mixture was filtered through a short pad of celite and the filtrate was evaporated. The crude product was purified by flash chromatography (eluent: 0 to 70% EtOAc in n-heptane) to obtain compound 6, which was used as is.

Preparation of Ethyl (S)-7-((4-(2-((tert-butoxycarbonyl)amino)-4,4-dimethylpentanamido)phenethyl)(methyl)amino)-4,4-dimethyl-7-oxoheptanoate

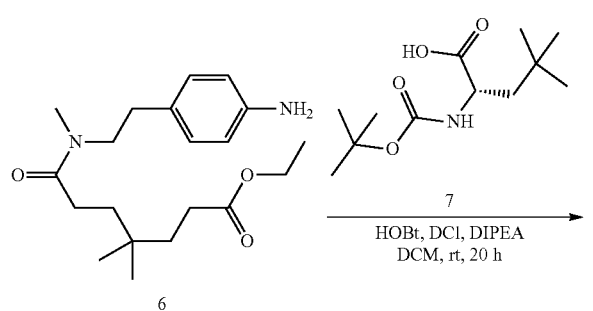

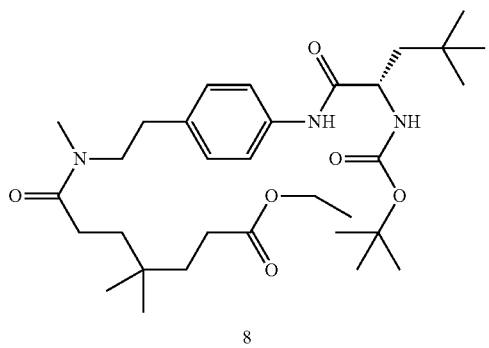

Acid reagent (7, 314 mg, 1.3 mmol, 1.1 equiv) was dissolved in anhydrous DCM (3.5 mL) then DIPEA (301 mg, 2.33 mmol, 2.0 equiv), HOBt (190 mg, 1.4 mmol, 1.2 equiv) and EDCI (268 mg, 1.4 mmol, 1.2 equiv) were added. The resulting mixture was stirred at rt for 30 min then starting compound 6 (406 mg, 1.16 mmol, 1.0 equiv) was added and stirring was continued at rt for 20 h. As no full conversion was detected by TLC and LCMS analyses, another portion of DIPEA (60 mg, 0.46 mmol, 0.4 equiv), HOBt (63 mg, 0.46 mmol, 0.4 equiv) and EDCI (89 mg, 0.46 mmol, 0.4 equiv) were added and stirring was continued for 20 h. The progress of the reaction was monitored by TLC (CHCl₃:MeOH=20:1) and LCMS analyses. After completion, the reaction mixture was diluted with DCM and washed with water and brine. The organic phase was dried over MgSO₄, filtered and concentrated in vacuo. The crude product was purified by column chromatography (eluent: 0 to 80% EtOAc in n-heptane) to obtain Compound 8.

Preparation of (S)-7-((4-(2-((Tert-butoxycarbonyl)amino)-4,4-dimethylpentanamido)phenethyl)(methyl)amino)-4,4-dimethyl-7-oxoheptanoic acid
(Intermediate A)

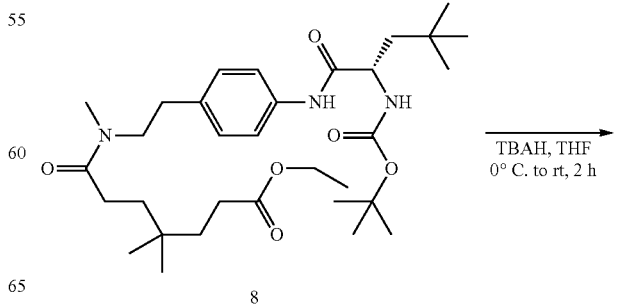

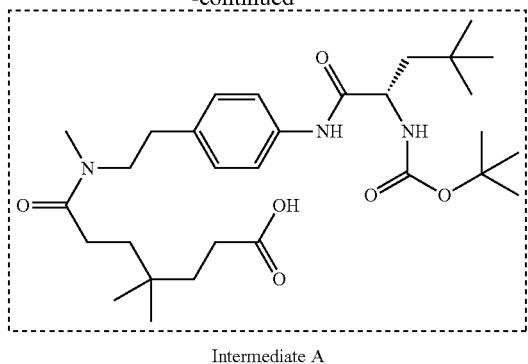

Intermediate A

Starting compound 8 (518 mg, 0.9 mmol) was dissolved in THF (8.9 mL) and cooled to 0° C. then TBAH (2042 mg, 40 w/w % in water, 3.15 mmol, 3.5 equiv) was added dropwise. The resulting mixture was let to warm up to rt and stirred for 2 h. The progress of the reaction was monitored by TLC (CHCl$_3$:MeOH=20:1) and LCMS analyses. After completion, the volatile solvent was evaporated in vacuo, the residue was diluted with water and its pH was adjusted to 3-4 by the addition of 10 w/w % aq. citric acid solution and extracted with EtOAc twice. The organic phase was dried over MgSO$_4$, filtered and concentrated under reduced pressure to obtain Intermediate A, which was used as is.

Synthesis of Intermediate B

Preparation of Methyl 4-(2-((tert-butoxycarbonyl)(methyl)amino)ethoxy)benzoate

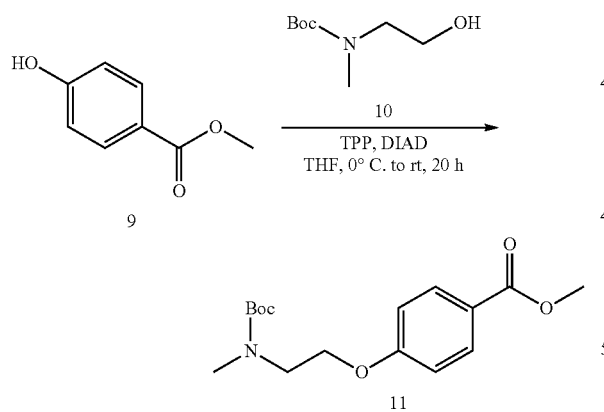

Starting compound 9 (2.0 g, 13.1 mmol, 1.0 equiv) was dissolved in anhydrous THF (52 mL) then hydroxy reagent (10, 3.45 g, 19.7 mmol, 1.5 equiv) and TPP (5.17 g, 19.7 mmol, 1.5 equiv) were added under Ar atmosphere. The resulting mixture was cooled to 0° C. then a solution of DIAD (3.98 g, 19.7 mmol, 1.5 equiv) in anhydrous THF (19 mL) was added dropwise. The reaction mixture was allowed to warm up to rt and stirred at this temperature for 20 h. The progress of the reaction was monitored by TLC (n-heptane:EtOAc=4:1) and LCMS analyses. After completion, the reaction mixture was diluted with EtOAc and washed with water and brine. The organic phase was dried over MgSO$_4$, filtered and evaporated. The crude product was purified by column chromatography (eluent: 0 to 40% EtOAc in n-heptane) to obtain the compound 11.

Preparation of 4-(2-((Tert-butoxycarbonyl)(methyl)amino)ethoxy)benzoic acid

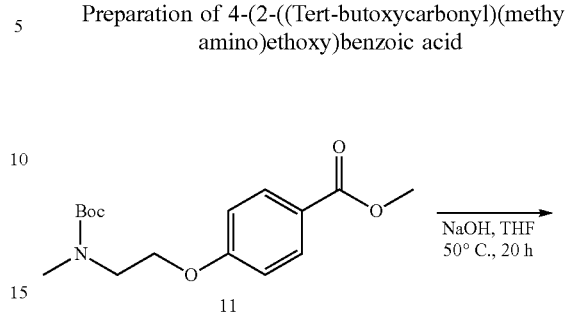

Starting compound 11 (3.25 g, 10.5 mmol, 1.0 equiv) was dissolved in THF (32.5 mL) then 1 M aq. NaOH solution (1.26 g, 31.5 mmol, 3 equiv) was added. The resulting mixture was stirred at 50° C. for 20 h. The progress of the reaction was monitored by TLC (n-heptane:EtOAc=2:1) and LCMS analyses. After completion, the volatile solvent was removed in vacuo, the residue was diluted with water and extracted with EtOAc. The pH of the aqueous phase was adjusted to 3-4 by addition the addition of 1 M aq. HCl solution, then extracted with EtOAc. The organic phase was dried over MgSO$_4$, filtered and evaporated under reduced pressure to obtain the compound 12, which was used as is.

Preparation of Methyl 5-(aminomethyl)-2-fluorobenzoate

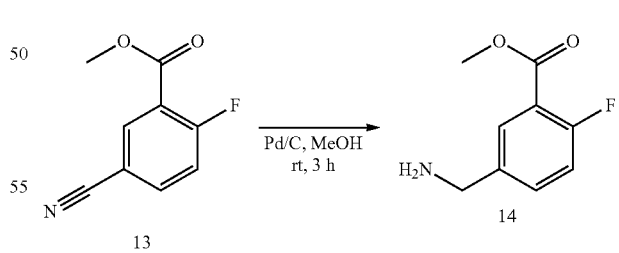

Starting compound 13 (3.0 g, 16.7 mmol) was dissolved in MeOH (168 mL), then Pd/C (10% Pd on C, 300 mg, 2.82 mmol, 0.17 equiv) was added. The vessel was closed and stirred under atmospheric pressure H$_2$ (balloon) at rt for 3 h. The progress of the reaction was monitored by TLC (CHCl$_3$:MeOH=20:1) and LCMS analyses. After completion, the mixture was filtered through a short pad of celite and the filtrate was evaporated to obtain the compound 14.

117

Preparation of Methyl 5-((4-(2-((tert-butoxycarbonyl)(methyl)amino)ethoxy)benzamido)methyl)-2-fluorobenzoate

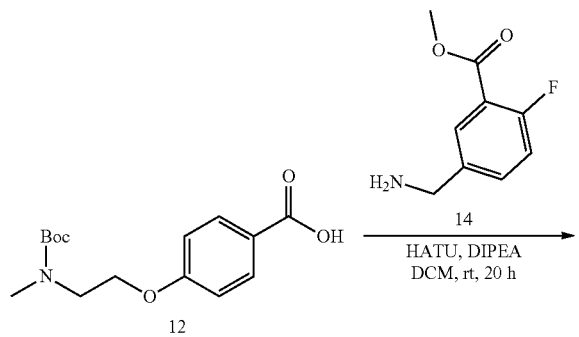

Starting compound 12 (2.7 g, 9.4 mmol, 1.0 equiv) was dissolved in anhydrous DCM (23 mL), then DIPEA (3.0 g, 23.5 mmol, 2.5 equiv) and HATU (3.9 g, 10.3 mmol, 1.1 equiv) were added. After 10 min stirring, reagent (14, 2.7 g, 70 w/w %, 10.3 mmol, 1.1 equiv) was added. The resulting mixture was stirred at rt for 20 h. The progress of the reaction was monitored by TLC (n-heptane:EtOAc=2:1) and LCMS analyses. After completion, the mixture was diluted with DCM and washed with water and brine. The organic phase was dried over MgSO$_4$, filtered and evaporated under reduced pressure. The crude product was purified by column chromatography (eluent: 0 to 60% EtOAc in n-heptane) to obtain the compound 15.

Preparation of Methyl 2-fluoro-5-((4-(2-(methylamino)ethoxy)benzamido)methyl)benzoate (Intermediate B)

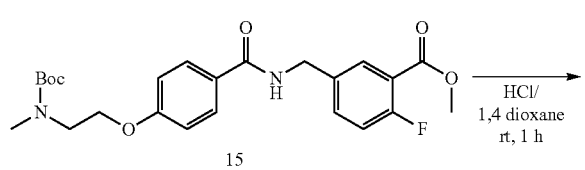

118

-continued

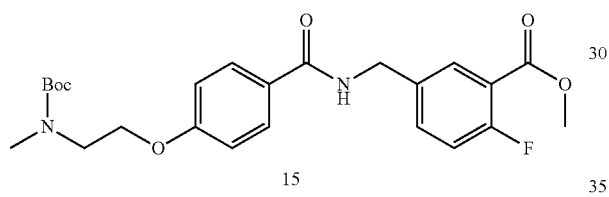

Intermediate B

Starting compound 15, (2.28 g, 4.9 mmol, 1.0 equiv) was dissolved in 1,4-dioxane saturated with HCl gas (49 mL). The resulting mixture was stirred at rt for 1 h. The progress of the reaction was monitored by TLC (CHCl$_3$:MeOH=20:1) and LCMS analyses. After completion, the reaction mixture was concentrated in vacuo, the residue was dissolved in water and extracted with EtOAc. The pH of the aqueous phase was adjusted to 9-10 by addition of 10 w/w % aq. Na$_2$CO$_3$ solution, then extracted with EtOAc. The combined organic phase was dried over MgSO$_4$, filtered and evaporated under reduced pressure. The crude product was purified by column chromatography (eluent: 0 to 5% MeOH in CHCl$_3$) to obtain Intermediate B.

Synthesis of Compound 1A

Preparation of Ethyl (S)-5-((4-(2-(7-((4-(2-((tert-butoxycarbonyl)amino)-4,4-dimethylpentanamido)phenethyl)(methyl)amino)-N,4,4-trimethyl-7-oxo-heptanamido)ethoxy)benzamido)methyl)-2-fluorobenzoate

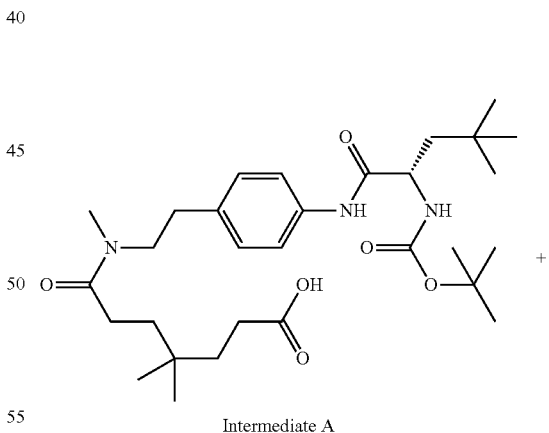

Intermediate A

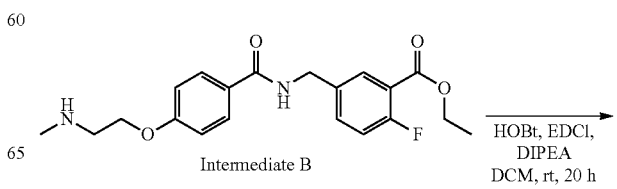

119
-continued

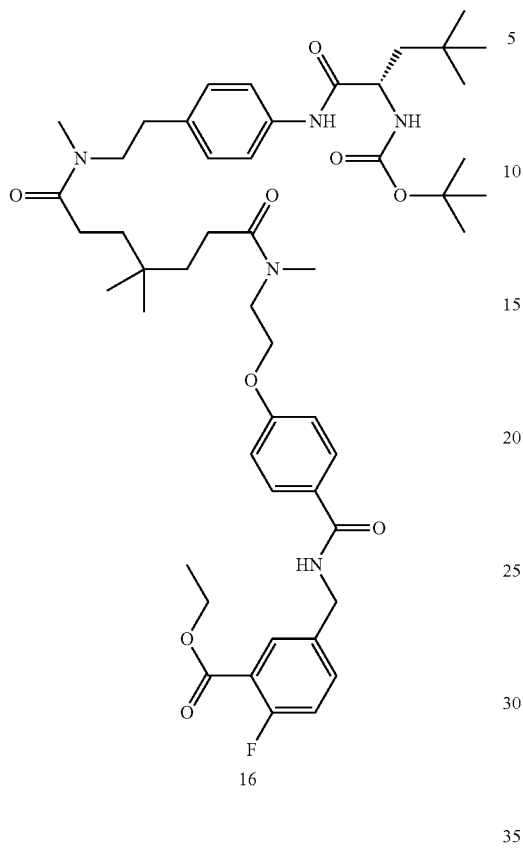

16

Intermediate A (500 mg, 0.82 mmol, 1.0 equiv) was dissolved in anhydrous DCM (3.3 mL) then DIPEA (265 mg, 2.05 mmol, 2.5 equiv), HOBt (133 mg, 0.99 mmol, 1.2 equiv) and EDCI (189 mg, 0.99 mmol, 1.2 equiv) were added. The resulting mixture was stirred at rt for 30 min then amine reagent (Intermediate B, 355 mg, 0.99 mmol, 1.2 equiv) was added and stirring was continued at rt for 20 h. The progress of the reaction was monitored by TLC (CHCl₃: MeOH=10:1) and LCMS analyses. After completion, the reaction mixture was diluted with DCM and washed with water and brine. The organic phase was dried over MgSO₄, filtered and concentrated in vacuo. The crude product was purified by column chromatography (eluent: 0 to 6% MeOH in chloroform) to obtain the compound 16 (460 mg, 63%).

120

Preparation of Ethyl (S)-5-((4-(2-(7-((4-(2-amino-4,4-dimethylpentanamido)phenethyl)(methyl)amino)-N,4,4-trimethyl-7-oxoheptanamido)ethoxy)benzamido)methyl)-2-fluorobenzoate

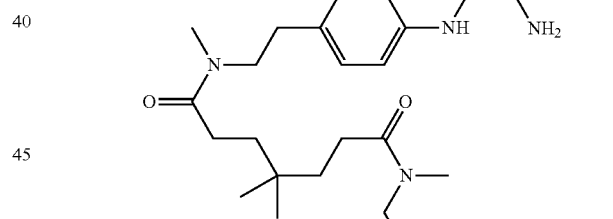

16

HCl/
1,4 dioxane
10° C., 2 h

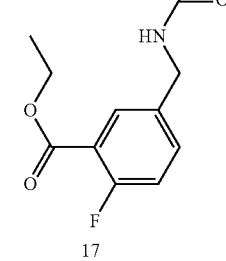

17

Starting compound 16 (460 mg, 0.52 mmol, 1.0 equiv) was dissolved in 1,4-dioxane saturated with HCl gas (2 mL). The resulting mixture was stirred at 10° C. for 2 h. The progress of the reaction was monitored by TLC (CHCl$_3$:MeOH=10:1) and LCMS analyses. After completion, the reaction mixture was evaporated in vacuo, the residue was dissolved in water and extracted with DCM. The pH of the aqueous phase was adjusted to 10-11 by addition the addition of 10% aq. Na$_2$CO$_3$ solution, then extracted with DCM. The organic phase was dried over MgSO$_4$, filtered and evaporated under reduced pressure to give the compound 17 (408 mg, quant. yield) %), which was used as is.

Preparation of (S)-5-((4-(2-(7-((4-(2-amino-4,4-dimethylpentanamido)phenethyl)(methyl)amino)-N,4,4-trimethyl-7-oxoheptanamido)ethoxy)benzamido)methyl)-2-fluorobenzoic acid (18)

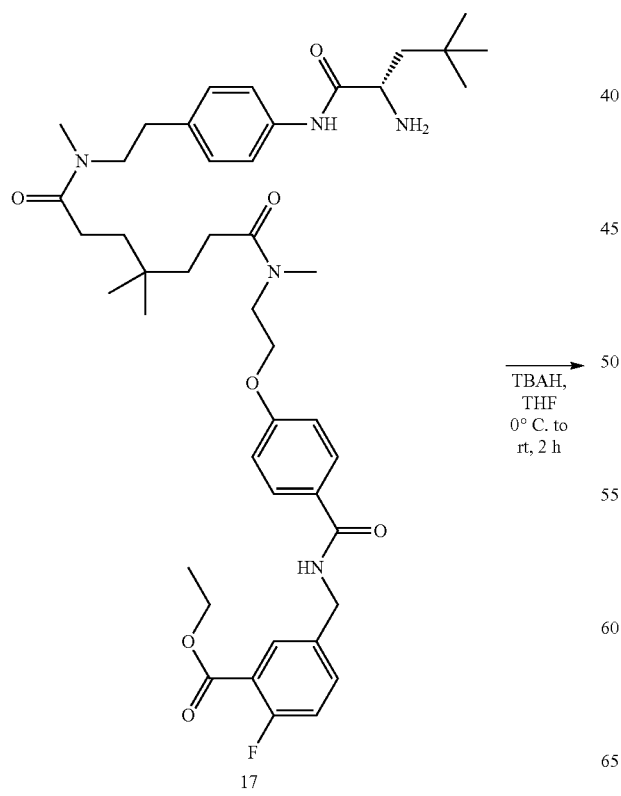

17

TBAH, THF
0° C. to rt, 2 h

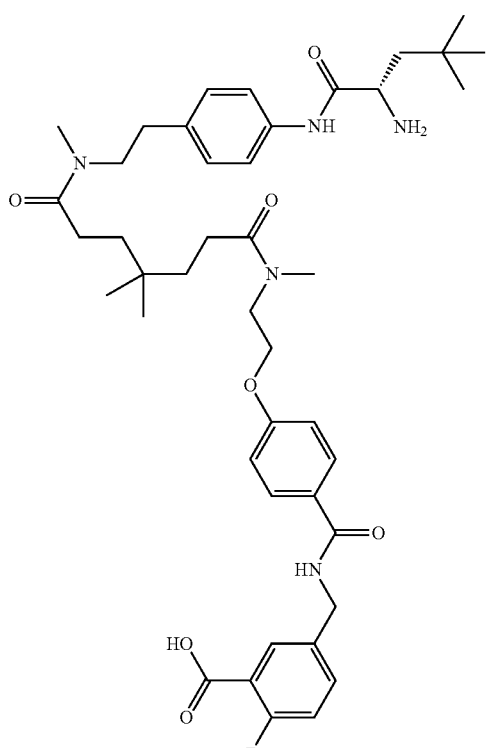

18

Starting compound 17 (408 mg, 0.52 mmol, 1.0 equiv) was dissolved in THF (5.1 mL) and cooled to 0° C. TBAH (838 mg, 40 w/w % in water, 1.29 mmol, 2.5 equiv) was added dropwise. The resulting mixture was let to warm up to rt and stirred for 2 h. The progress of the reaction was monitored by TLC (CHCl$_3$:MeOH=10:1) and LCMS analyses. After completion, the volatile solvent was evaporated in vacuo, the residue was diluted with water and its pH was adjusted to 3-4 by the addition of 10% aq. citric acid solution. The precipitate was collected by filtration and washed with DCM to obtain the compound 18, which was used as is.

Preparation of (S)-5⁴-fluoro-14,18,18,22-tetramethyl-8-neopentyl-25-oxa-3,7,10,14,22-pentaaza-1,11(1,4),5(1,3)-tribenzenacyclopentacosaphane-2,6,9,15,21-pentaone (Compound 1A)

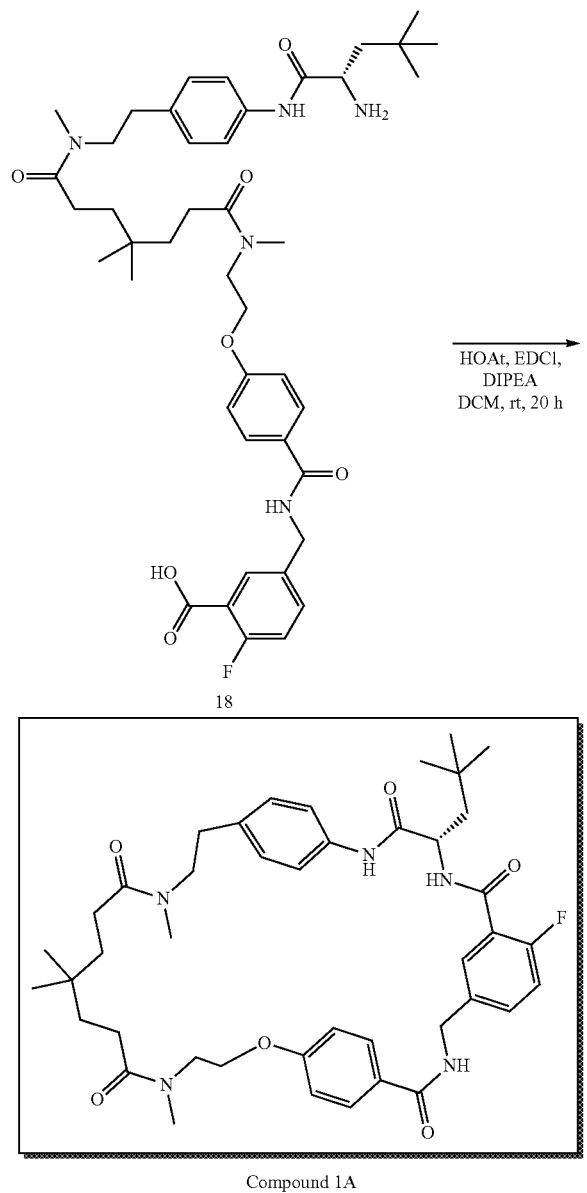

Compound 1A

DIPEA (100 mg, 0.77 mmol, 6 equiv) was combined with HOAt (52.6 mg, 0.39 mmol, 3.0 equiv) and EDCI (74.1 mg, 0.39 mmol, 3 equiv) in anhydrous DCM (20 mL), then a solution of starting amino acid 18 (100 mg, 0.13 mmol, 1.0 equiv) dissolved in a mixture of anhydrous DCM (20 mL) and DIPEA (50 mg, 0.39 mmol, 3.0 equiv) was added at rt, via a syringe pump over 3 h. The resulting mixture was stirred at rt overnight. The progress of the reaction was monitored by TLC (CHCl$_3$:MeOH=10:1) and LCMS analyses. After completion, the reaction mixture was washed with water and brine. The organic phase was dried over MgSO$_4$, filtered and concentrated in vacuo. The crude product was purified by column chromatography (eluent: 0 to 6% MeOH in chloroform) then by preparative HPLC to obtain the Compound 1A. ES+ MS m/z 758 [M+H]⁺.

In some embodiments, the compound has a linear structure and the last step of synthesis, cyclization (e.g., product 18 cyclized into Compound 1A), is absent. Compounds 1-74 emplified in Table 7 were synthesized following the schemes analogous to those in Synthetic Route for Compound 1A, absent the cyclization.

Example 2: Assessing Compounds for Activities Against DUBs

Inhibiting the Catalytic Activity of USP9X
The inhibition property of compound Compound 1A was evaluated in assays measuring the ability of USP9X to catalyze the hydrolysis of the amide bond between the C terminal carboxylate of ubiquitin and rhodamine1 10 of the fluorogenic substrate ubiquitin-rhodamine 110. To the wells of a 96 well reaction plate was added 12.5 µL USP9X solution (1.3 nM) in assay buffer (100 mM NaCl, 1 mM DTT, 0.1% bovine serum albumin, 0.05% Tween 20, 50 mM Tris, pH 7.5). 12.5 µL of Compound 1A in assay buffer (4× final concentration) was added to the wells containing the USP9X solution, and the solution was gently mixed by pipetting up and down several times. The plate was sealed and incubated at room temperature for 20 minutes. Then 25 uL of the 1 µM substrate (ubiquitin-rhodamine1 10) solution was added in assay buffer. The final substrate concentration was 0.5 µM. The fluorescence from each of the wells was determined using 485 nm excitation and 535 nm emission for a series of time points. The slope for the rate of change of the fluorescence was determined and plotted vs the concentration of Compound 1A. The fluorescence signal decreased and plateaued when increasing the concentration of Compound 1A. The results indicated that Compound 1A partially inhibited the activity of USP9X.

Binding to USP9X and Inhibiting USP9X Enzymatic Activities
Direct binding of the compounds (Compound 2A, Compound 3A, and Compound 4A) to USP9X was evaluated using a Biacore T200 instrument at 25° C. according to the manufacturer's instructions. USP9X was immobilized on a chip for surface plasmon resonance measurements via Biacore T200. Solutions of compound Compound 2A at various concentrations were flowed over the immobilized USP9X and the change in refractive index was monitored. The displayed traces indicated the binding of Compound 2A to USP9X and its subsequent dissociation. A value (0.48 µM) for the equilibrium dissociation constant, K$_D$, were determined from the ratio of the dissociation rate constant to the association rate constant. The values of the maximum response for each concentration of Compound 2A were plotted and were consistent with a binding of the compound to a single site on USP9X with a dissociation equilibrium constant of 1.9 µM in reasonable agreement with value determined from the kinetic association and dissociation rates. Compound 2A did not bind to carbonic anhydrase immobilized upon a chip, indicating that non-specific binding was negligible.

USP9X enzyme assays were set up in a 96 well plate to assess the abilities of Compound 3A and Compound 4A to inhibit the activity of USP9X, respectively. Ubiquitin-rhodamine1 10 was used as the substrate and ubiquitin aldehyde was included in the assay as a positive control. Ubiquitin aldehyde binds covalently to the thiol group of the active site Cys of USP9X. The activity of USP9X was completely abolished by incubation with ubiquitin aldehyde. The activity of USP9X was reduced approximately 60% with the higher concentrations of Compound 2A, Compound 3A, and Compound 4A (>10 µM). The partial inhibition of USP9X was not due to the lack of solubility of these compounds at high concentrations but instead was shown to have a mechanistic basis. The $IC_{50}$ for the inhibition of USP9X activity by Compound 2A was calculated from a four parameter, variable slope fit of the data in GraphPad Prism to be 0.39 µM. This value was similar to the values of the dissociation equilibrium constant determined for this compound from the surface plasmon resonance spectrometry. The $IC_{50}$ values of Compound 2A, Compound 5A, Compound 7A, and Compound 11A against USP9X were determined to be 0.39 µM, 0.03 µM, 0.011 µM, and 0.048 µM, respectively.

Mechanism of Inhibition of USP9X by the Compounds

In order to determine whether there was a mechanistic basis for the observed partial inhibition of USP9X activity by Compound 2A, steady-state enzyme inhibition kinetic assays were carried out in which the activity of USP9X was determined as a function of the substrate ubiquitin-rhodamine110 concentration at various concentrations of the inhibitor Compound 2A.

The data were fit to a general model for enzyme inhibition (FIG. 1E) so the values of the parameters determined from the assays specified the mode of inhibition. For example, in the case of $\alpha=1$ and $\beta=0$, it corresponded to purely non-competitive inhibition. For $\alpha=$infinity and $\beta=1$, it corresponded to purely competitive inhibition. The values of all the parameters, $K_S$, $K_I$, $k_{cat}$, $\alpha$, and $\beta$ could be determined from the steady state measurements. The enzyme reactions were set up as described in the Inhibiting the catalytic activity of USP9X section. The concentration of the substrate ubqiutin-rhodamine110 was varied. The initial rates of the reactions were determined at several concentrations of the inhibitor Compound 2A. In order to determine the values of the parameters $K_S$ and $k_{cat}$, the reaction rates in the absence of the inhibitor Compound 2A, the initial reaction rate data were fit to the standard Michaelis-Menten equation v=Vmax [S]/(Km+[S]). The values of $\alpha$ and $\beta$ could then be determined by fitting the initial rate data of the enzyme reaction at various concentrations of Compound 2A to a modified version of the Michaelis-Menten equation, designating both Vmax and $K_S$ apparent to distinguish the apparent values of the parameters determined from these plots to the true values for these parameters determined from the steady state kinetics in the absence of Compound 2A. The values of a and p could be determined from the variation of the slopes and intercepts of the series of double reciprocal plots of 1/v versus 1/[S] for each concentration of Compound 2A. The plots of 1/Δ slope vs. 1/[Compound 2A] or 1/Δ intercept vs. 1/Compound 2A were linear and from these plots values of $\alpha$, $\beta$, and $K_I$ could be determined. The results of this analysis were shown in Table 2. The two values determined for $K_I$ were from the two different plots. The value of $\alpha$, 1.73, was >1 and indicated that the affinity of the USP9X-Compound 2A complex for the substrate was weaker than that for USP9X itself, suggesting a competitive mode of inhibition. The value of $\beta$, 0.71, was <1 and indicated that the rate of the conversion of substrate to product was slower for the USP9X-Compound 2A complex with the substrate than for the USP9X-substrate complex itself, suggesting a non-competitive inhibition. Together these values of the inhibition parameters served to classify the mode of inhibition as hyperbolic mixed inhibition (See Segel I. H. Enzyme kinetics: behavior and analysis of rapid equilibrium and steady-state enzyme systems. New York: Wiley-Interscience).

Inhibition Kinetic Parameters Predict Partial Inhibition of the Compounds Against USP9X To determine whether the values of the parameters determined from enzyme inhibition kinetics in Table 2 predicts the observed partial inhibition of USP9X by compounds in the previous figures, a theoretical dose-response curve for the activity of USP9X vs. [Compound 2A] was constructed using the Michaelis-Menten equation for the reaction. As shown in FIG. 1F, the theoretical dose-response curve (solid line) was compared with the actual dose-response curve (filled circles) obtained for Compound 2A as described in the Binding to USP9X and Inhibiting USP9X Enzymatic Activities section. The results were in support of a mechanistic basis for the observed partial inhibition of USP9X by Compound 2A.

Compounds have a Common Mechanism of Inhibition of USP9X

In addition to Compound 2A as described above, Compound 5A, Compound 7A, and Compound 11A were evaluated in order to determine whether they exhibited a common mechanism of inhibition of USP9X. These results of inhibition kinetic parameters were summarized in Table 2.

TABLE 2

Inhibition Kinetic Parameters of Compound 2A, Compound 5A, Compound 7A, and Compound 11A

| Compound | Compound 2A | Compound 5A | Compound 7A | Compound 11A |
|---|---|---|---|---|
| USP9X $IC_{50}$ nM | 390 | 30 | 11 | 48 |
| $K_I$, nM | 120[1], 290[2] | 6.7[1], 24[2] | 9.4[1], 10.3[2] | 7.0[1], 69[2] |
| α | 1.73 | 2.3 | 1.85 | 2 |
| β | 0.71 | 0.78 | 0.72 | 0.88 |
| $K_S$, µM | 0.95 | 1.2 | 1.87 | 0.91 |
| $V_{MAX}$ RFU/min | 310 | 335 | 589 | 408 |

The two values for $K_I$ were determined by two different methods for determining this parameter from the kinetic data: 1 represented a value determined from the slope of the 1/Δ intercept vs 1/[I] plot; 2 represented a value determined from the y intercept of the 1/Δ slope vs 1/[I] plot. These four compounds inhibited USP9X catalytic activity with the same mechanism-hyperbolic mixed inhibition. Only the values of the parameters varied for the compounds. The potency of the inhibition of USP9X improved significantly for this series of compounds beginning with several hundred nM for Compound 2A and increasing by nearly two orders of magnitude for Compound 7A, whether comparing the IC50s from dose-response curves or the values for $K_I$ determined from steady-state enzyme inhibition kinetics.

Compounds 1-74 in Table 7 were also evaluated for their inhibitions against USP9X. The results were presented in the following Table 8.

TABLE 8

| Compound | USP9X $IC_{50}$/µM |
|---|---|
| 1 | 0.53 |
| 2 | 0.18 |
| 3 | 0.28 |
| 4 | 0.054 |
| 5 | 0.055 |
| 6 | 0.70 |
| 7 | 0.59 |
| 8 | 1.1 |

TABLE 8-continued

| Compound | USP9X IC$_{50}$/μM |
|---|---|
| 9 | 0.15 |
| 10 | 0.091 |
| 11 | 0.08 |
| 12 | 1.3 |
| 13 | 0.044 |
| 14 | 0.12 |
| 15 | 23 |
| 16 | 18 |
| 17 | 11 |
| 18 | 10 |
| 19 | 8 |
| 20 | 0.063 |
| 21 | 0.024 |
| 22 | 0.42 |
| 23 | 0.24 |
| 24 | 0.066 |
| 25 | 0.068 |
| 26 | >50 |
| 27 | >50 |
| 28 | 32 |
| 29 | 0.28 |
| 30 | >50 |
| 31 | 6.0 |
| 32 | >50 |
| 33 | >50 |
| 34 | >50 |
| 35 | 7.0 |
| 36 | >50 |
| 37 | >50 |
| 38 | >50 |
| 39 | 36 |
| 40 | — |
| 41 | 0.09 |
| 42 | 1.3 |
| 43 | 0.76 |
| 44 | 0.24 |
| 45 | 2.1 |
| 46 | 0.87 |
| 47 | 0.32 |
| 48 | 8.9 |
| 49 | 5 |
| 50 | 2.3 |
| 51 | 0.052 |
| 52 | 0.055 |
| 53 | 0.36 |
| 54 | 3.4 |
| 55 | 4.7 |
| 56 | 4.5 |
| 57 | 7.0 |
| 58 | 4.9 |
| 59 | 11 |
| 60 | 13 |
| 61 | 5.8 |
| 62 | 6.9 |
| 63 | 0.22 |
| 64 | 0.65 |
| 65 | 0.60 |
| 66 | >50 |
| 67 | >50 |
| 68 | >50 |
| 69 | >50 |
| 70 | >50 |
| 71 | >50 |
| 72 | 29 |
| 73 | 15 |
| 74 | 12 |

Binding Specificity

Compounds were screened for DUB inhibitory and apoptotic activity against other deubiquitylases in a DUB selectivity panel using ubiquitin-AMC (BPS Bioscience Inc.). The same assay for evaluating the inhibition property of compound Compound 1A described above was carried out but only USP9X was replaced with other deubiquitylases. The compounds showed minimal or no detectable effect on DUBs tested. Specifically, 5 μM Compound 5A screened using 500 nM Ubiquitin-AMC exhibited no detectable effect on CYLD, USP2, USP5, USP7, USP13, USP25, USP4, and UCH-L3 (i.e., 0% inhibition); and 5% inhibition for USP30, 1% inhibition for USP10, 2% inhibition for USP15, 3% inhibition for VCPIP, and 5% inhibition for UCH-L1. An attempt was made to determine an IC$_{50}$ value for inhibition of Compound 5A against several DUBS and IC$_{50}$ was determined to be above 50 μM for USP7, above 50 μM for USP2, and 15 μM for USP28.

The results from the assessments for activities against DUBs indicated that the compounds partially inhibited USP9X and were selective for USP9X. In contrast, another partially selective USP9X inhibitor, WP 1130, inhibited not only USP9x but also USP5, USP14, UCH-L1, and UCH37.

Screening for Various Cell Lines

Compounds can be screened for DUB inhibitory and apoptotic activity in a panel of CML, myeloma and Mantle cell lymphoma cell lines. Selected compounds can also be tested for DUB inhibition in intact cells and in isolated DUB (USP9X-UCH domain) enzyme preparations. General descriptions of the methods employed in these assays can be found, e.g., in Kapuria, et al., A novel small molecule deubiquitinase inhibitor blocks Jak2 signaling through Jak2 ubiquitination, Cell Signal, 2011, 23(12):2076-85; Kapuria, et al., Deubiquitinase inhibition by small-molecule WP 1130 triggers aggresome formation and tumor cell apoptosis. Cancer Res, 2010. 70(22): p. 9265-76; Sun, et al., Bcr-Abl ubiquitination and Usp9x inhibition block kinase signaling and promote CML cell apoptosis. Blood, 2011. 117(11): p. 3151-62; Kapuria, et al., Protein cross-linking as a novel mechanism of action of a ubiquitin-activating enzyme inhibitor with anti-tumor activity. Biochem Pharmacol, 2011. 82(4): p. 341-9; and Bartholomeusz, et al., Activation of a novel Bcr/Abl destruction pathway by WP1130 induces apoptosis of chronic myelogenous leukemia cells. Blood, 2007. 109(8): p. 3470-8. Purified recombinant USPx9 (R&D Systems) in 50 mM Tris buffer pH 7.5, 1 mM DTT, 100 mM NaCl, 0.05% Tween 20 and 0/1% BSA is used at a concentration of 0.325 nM with 0.5 μM ubiquitin-rhodamine (R&D Systems).

Chemical structures can be screened for inhibitory activity using this assay. Fluorescent scans are used to assess inhibitory activity in this enzyme assay.

Example 3: Assessing Compounds for Inhibiting Cancer Cells

Inhibitory Activities Against the Proliferation of Mia-Paca-2 and Other Cancer Cells Compound Compound 9A was tested for the ability to inhibit the proliferation of Mia-Paca-2 pancreatic cancer cells. Mia-Paca-2 and MDA-MB-231 cells were seeded into the wells of a 96 well tissue culture plate in complete medium (10% fetal calf serum) and incubated overnight at 37° C./5% CO$_2$). The medium was exchanged for fresh medium containing varying concentrations of Compound 9A and the plate was incubated for 72 hours at 37° C./5% CO$_2$. The viability of cells at the end of this incubation was assessed with the WST-1 reagent. To 10 ml of warm (37° C.) complete medium, 1 ml WST-1 reagent was added. The medium from the wells of the plate with the Mia-Paca-2 cells was removed and replaced with 100 μL of the WST-1 reagent in complete medium. The plate was incubated at 37 37° C./5% CO$_2$. At timed intervals the absorbance at 450 nm was determined for each well in a UV/Vis plate reader. For each well the slope of the plot of the absorbance 450 nm vs time was determined. The readings were normalized to that of the wells for the untreated control and a dose-response curve was plotted. A fit to the data was made from a four parameter, variable slope program (GraphPad Prism) and the $IC_{50}$ was determined. Compound 9A inhibited the proliferation of both types of cells, with an $IC_{50}$ of 10 nM for Mi-aPaCa-2 cells and 2 µM for MDA-MB-231 cells.

Figure 2A:
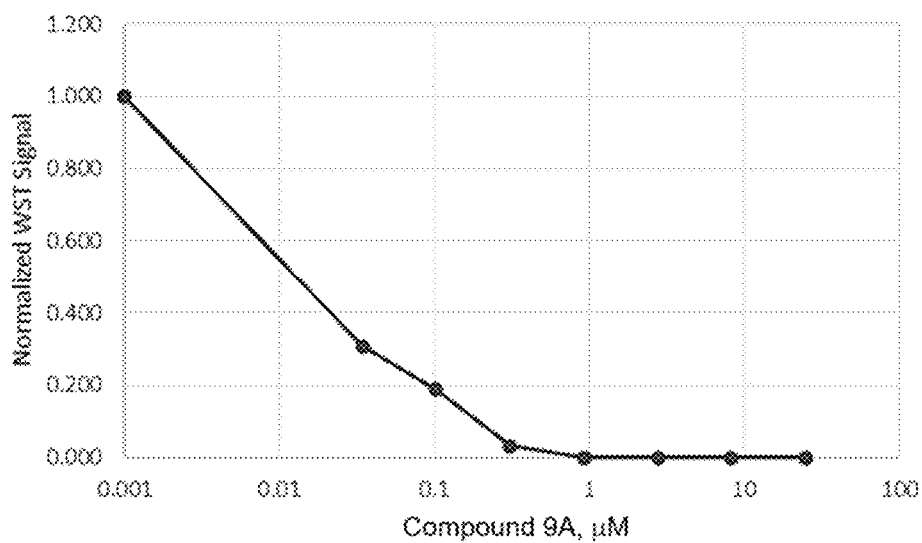
FIG. 2A is a graph depicting a cell viability dose-response curve of Compound 9A inhibiting Mia-Paca-2 cell proliferation after 72-hour treatment at 37° C. as assessed by the WST assay.
Figure 2B:
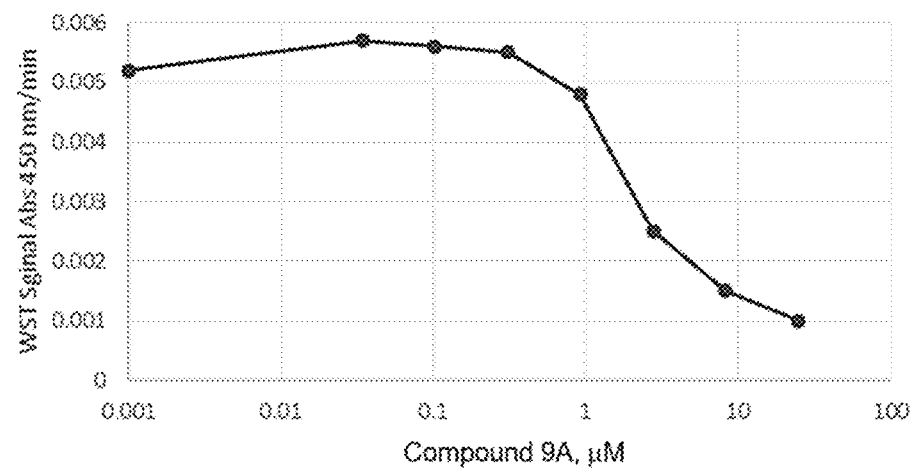
FIG. 2B is a graph depicting a cell viability dose-response curve of Compound 9A inhibiting MDA-MB-231 cell proliferation after 72-hour treatment at 37° C. as assessed by the WST assay.
Figure 2C:
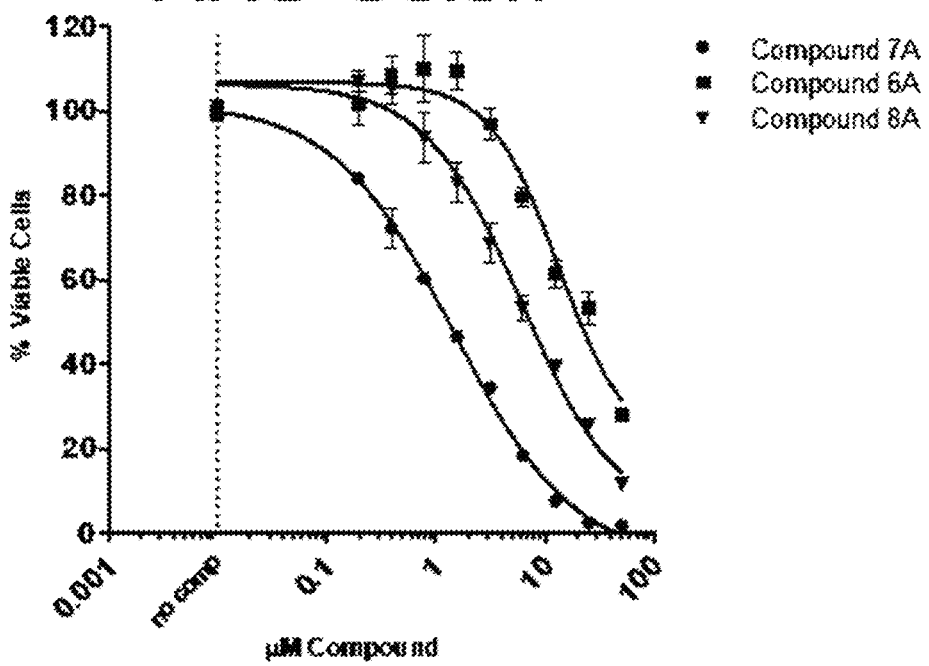
FIG. 2C is a graph depicting dose-response curves of RKO colon cell viability for Compound 7A, Compound 6A, Compound 8A in an RKO colon cell line.
Figure 2D:
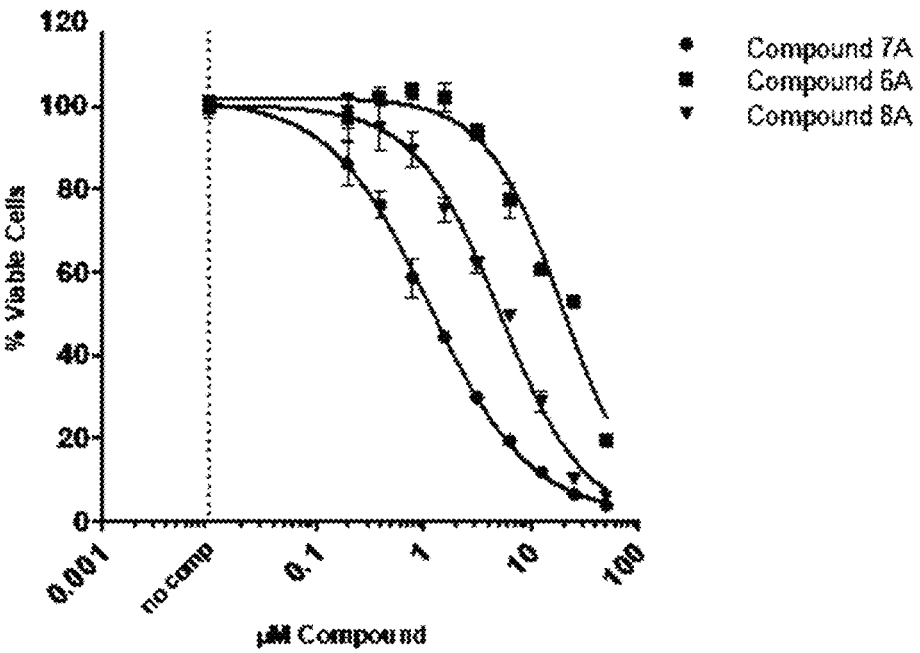
FIG. 2D is a graph depicting dose-response curves of BT-549 Breast cancer cell viability for Compound 7A, Compound 6A, Compound 8A in a BT-549 Breast cancer cell line.
Figure 2E:
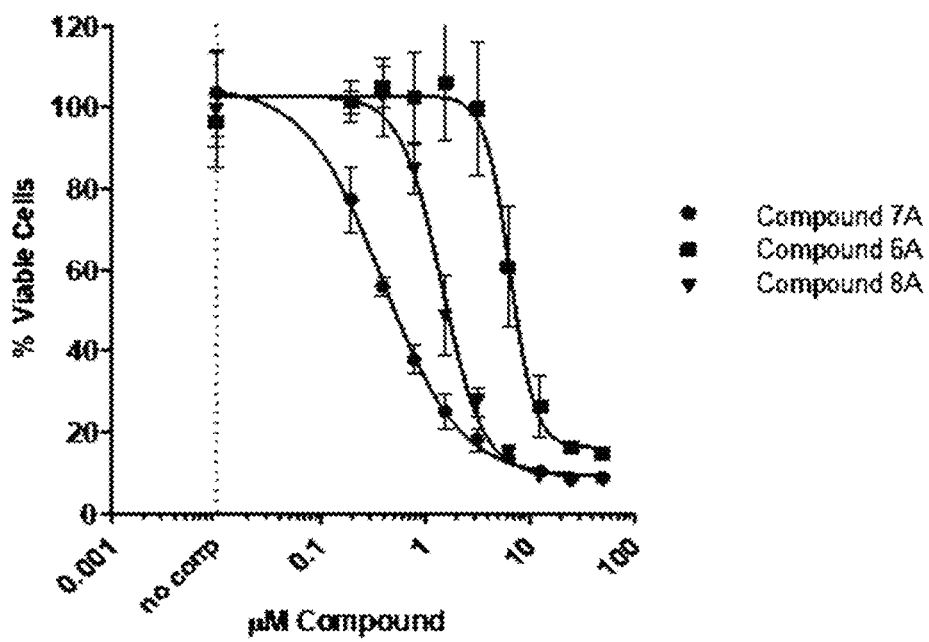
FIG. 2E is a graph depicting dose-response curves of MIA Paca-2 Pancreatic cell viability for Compound 7A, Compound 6A, Compound 8A in a MIA Paca-2 Pancreatic cell line.

The same procedures were also applied to the compounds Compound 7A, Compound 6A, and Compound 8A to test their inhibitory activities against RKO colon, Mia-Paca-2 pancreatic and BT-549 cancer cells. The results showed the significant decreases of cell viability in all three cancer cells treated with Compound 7A, Compound 6A, and Compound 8A each (FIG. 2C-2E).

Sensitivities of Multiple Cancer Cell Lines to the Compounds

The compounds were profiled on an ONCOLINES™ Profiler (Netherlands Translational Research Center) assayed with 66 cancer cell lines to determine if they were capable of inhibiting the proliferation of these cancer cells. The results showed 57 of 66 cancer cell lines were sensitive to Compound 7A, wherein Compound 7A had $IC_{50}$ values <1 µM in 9 cancer cell lines. Compound 7A had an $IC_{50}$ value over 32 µM in the malignant melanoma cell line MeWo. Compound 7A had an $IC_{50}$ value of 2.4 M in the ovarian cancer cell line OVCAR-3. Compound 7A had an Co value of 0.88 µM in the colon cancer cell line RKO. Compound 7A had an $IC_{50}$ value of 0.79 µM in the pancreatic cancer cell line MIA PaCa-2. Compound 7A had an $IC_{50}$ value of 0.2 µM in the triple negative breast cancer cell line BT-549. Table 3 provided $IC_{50}$ values for cell lines wherein Compound 7A were active at $IC_{50}$<5 µM.

Compound 7A had an $IC_{50}$ value of 0.486 µM in the CML cell line K-562. According to BH3 profiling (a functional assay to determine which of the pro-survival Bcl-2 proteins that a cell depends upon for survival), Mcl-1 was not essential for survival of K562. Inhibition of USP9X in K562 cells led to the K63 polyubiquitylation of Bcr-Abl (the oncogenic driver in K562) with consequent relocation to peri-nuclear aggresomes and thus loss of activity.

The profiling results from ONCOLINES™ Profiler indicated that various cancer cells were sensitive to the compounds and thus the compounds can be used as therapeutics for treating, inhibiting, or suppressing those cancers in Table 3.

Comparing the Compounds with Another USP9X Inhibitor

To further evaluate potency of the compounds, they were compared with the USP9X inhibitor WP1130 by screening both the compounds and WP1130 on a 66-cancer cell line panel ONCOLINES™ Profiler.

$IC_{50}$ ratios of WP1130/Compound 7A in 12 cancer cell lines were shown in Table 4.

TABLE 4

$IC_{50}$ Ratios of WP1130/Compound 7A in cancer cell lines

| Cell Line | Type | Compound 7A $IC_{50}$ µM | WP1130 $IC_{50}$ µM | $IC_{50}$ Ratio |
|---|---|---|---|---|
| LoVo | colon | 0.64 | 5.5 | 8.6 |
| RKO | colon | 0.88 | 4.3 | 4.9 |
| A-172 | glioblastoma | 1.10 | 5.6 | 5.1 |
| RPMI7951 | melanoma | 1.20 | 4.2 | 3.5 |
| A549 | lung | 3.00 | 14 | 4.7 |

TABLE 3

$IC_{50}$ of Compound 7A in Multiple Cell Lines

| Cell Line | ATCC ref | Disease | $IC_{50}$ µM |
|---|---|---|---|
| A-172 | CRL-1620 | Glioblastoma | 1.067 |
| A-204 | HTB-82 | Rhabdomyosarcoma | 1.360 |
| A375 | CRL-1619 | Malignant melanoma | 2.017 |
| A388 | CRL-7905 | Epidermal carcinoma | 2.394 |
| AN3 CA | HTB-111 | Endometrium adenocarcinoma | 0.660 |
| BT-20 | HTB-19 | Breast carcinoma | 1.394 |
| BT-549 | HTB-122 | Breast ductal carcinoma | 0.199 |
| CCRF-CEM | CCL-119 | Acute lymphoblastic leukemia, Tcell | 0.247 |
| Daoy | HTB-186 | Medulloblastoma, CNS | 3.379 |
| DoTc2 4510 | CRL-7920 | Cervix carcinoma | 0.963 |
| DU 145 | HTB 81 | Prostate carcinoma | 2.014 |
| HCT-116 | CCL-247 | Colon carcinoma | 2.390 |
| Hs 57BT | HTB-126 | Breast carcinoma | 1.414 |
| Jurkat E6.1 | TIB-152 | Leukemia, T cell | 0.548 |
| K-562 | CCL-243 | Chronic myelogenous leukemia (CML) | 0.486 |
| LoVo | CCL-229 | Colorectal adenocarcinoma | 0.635 |
| MIA PaCa-2 | CRL-1420 | Pancreatic ductal carcinoma | 0.790 |
| MOLT-4 | CRL-1582 | Acute lymphoblastic leukemia | 0.594 |
| NCI-H460 | HTB-177 | Large cell lung carcinoma | 2.093 |
| OVCAR-3 | HTB-161 | Ovary adenocarcinoma | 2.400 |
| PA-1 | CRL-1572 | Ovary teratocarcinoma | 2.073 |
| RKO | CRL-2577 | Colon carcinoma | 0.683 |
| RPMI-7951 | HTB-66 | Malignant melanoma | 1.197 |
| SK-N-AS | CRL-2137 | Neuroblastoma | 1.720 |
| SR | CRL-2262 | Large cell immunoblastic lymphoma | 1.584 |
| SUP-T1 | CRL-1942 | T-cell lymphoblastic lymphoma | 4.289 |
| VA-ES-BJ | CRL-2138 | Epithelioid carcinoma, bone | 0.682 |

TABLE 4-continued

IC$_{50}$ Ratios of WP1130/Compound 7A in cancer cell lines

| Cell Line | Type | Compound 7A IC$_{50}$ µM | WP1130 IC$_{50}$ µM | IC$_{50}$ Ratio |
|---|---|---|---|---|
| H82 | small cell lung | 1.10 | 6.6 | 6.0 |
| BT-20 | breast | 1.40 | 5.1 | 3.6 |
| BT-549 | breast | 0.20 | 5.4 | 27.0 |
| Hs578T | breast | 1.40 | 6.3 | 4.5 |
| DU145 | prostate | 2.00 | 9.6 | 4.8 |
| CCRF-CEM | ALL | 0.25 | 4.4 | 17.6 |
| MOLT-4 | ALL | 0.59 | 4.0 | 6.8 |

In 12 of 66 cell lines, Compound 7A was about 4-fold more potent than WP1130. In 3 of 66 cell lines, Compound 7A appeared to be inactive and WP1130 was above 4-fold more potent than Compound 7A. The 3 cell lines expressed high levels of the anti-apoptotic Bcl-xL, known to correlate with resistance to antagonism of Mcl-1. Further, as a less selective inhibitor of USP9X, WP1130 also inhibited the activity of other deubiquitylases, which might account for the observed higher potencies of WP1130 in certain cell lines. The results indicated that the compound was generally more potent than WP1130.

Inhibition Against U937 Cells and Intracellular Mcl-1

The effect of Compound 7A on U937 cells was assessed using the same experiment described in the Inhibitory Activities against the Proliferation of Mia-Paca-2 and Other Cancer Cells section above. In response to treatment with Compound 7A, proliferation of U937 leukemia cells was inhibited and induced apoptosis was obsessed by trypan blue staining. The IC$_{50}$ for the inhibition of U937 by Compound 7A for 72-hour treatment was 270 nM. Similar inhibiting effects of Compound 7A were observed in multiple cancer cell lines (e.g., cancer cell lines listed in Table 3).

Figure 3A:
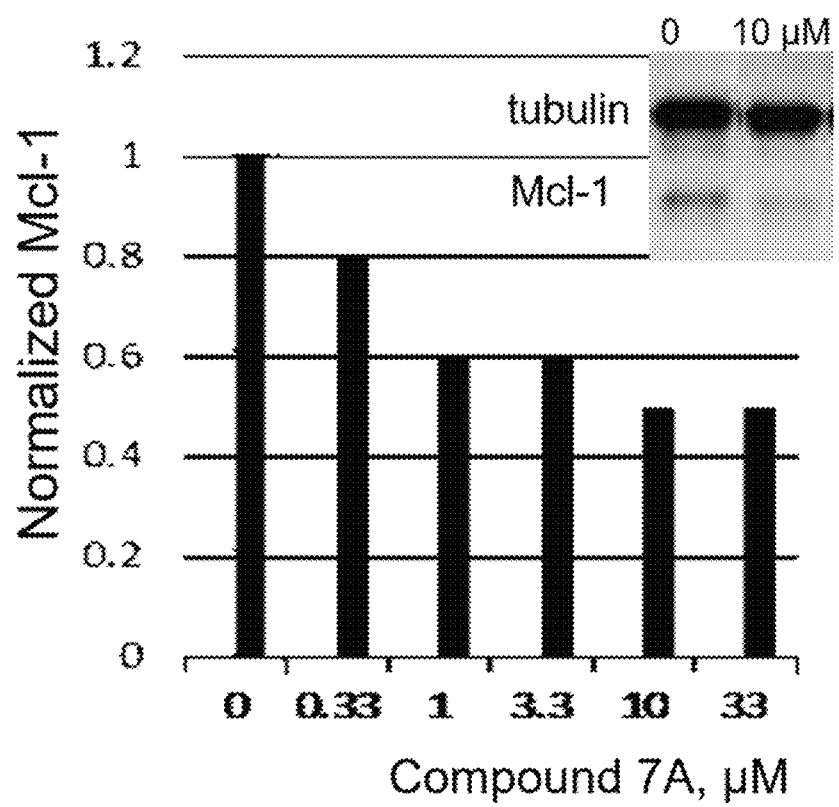
FIG. 3A is a graph showing normalized Mcl-1 levels at varying concentrations of Compound 7A after 24-hour treatment from western blot analysis. Displayed at the upper right corner is a representative blot of Mcl-1 at Compound 7A=0 and 10 μM with the housekeeping protein tubulin as a reference.
Figure 3B:
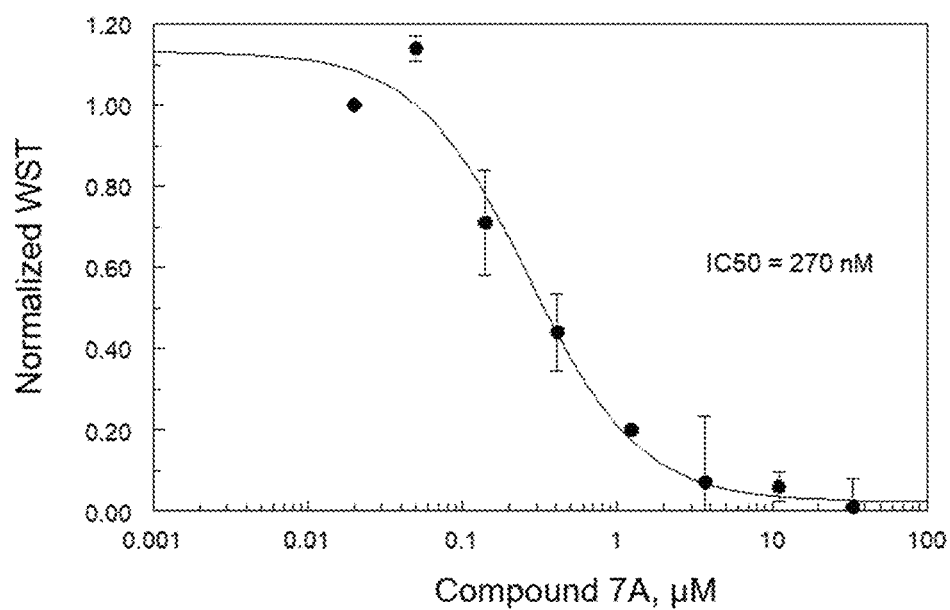
FIG. 3B is a graph depicting a cell viability dose-response curve of Compound 7A inhibiting U937 cell proliferation after 72-hour treatment, indicating $IC_{50}$=0.27 μM as assessed by the WST assay.
Figure 3C:
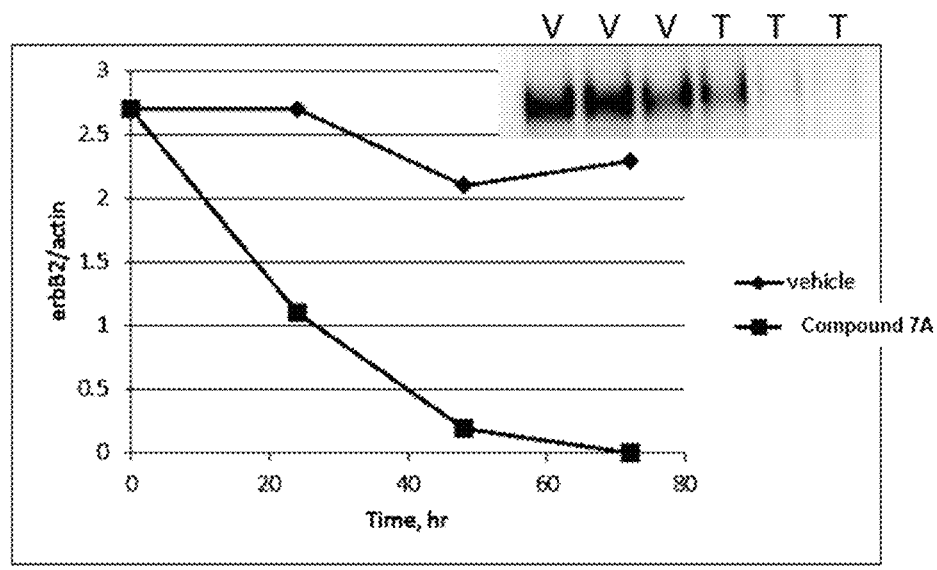
FIG. 3C is a graph showing the erbB2 level changes over time during 72 hours of Compound 7A treatment from western blot analysis, normalized by the housekeeping protein actin as a reference, compared with that during 72 hours of vehicle treatment only. Displayed at the upper right corner is a representative blot of erbB2 treated with 10 μM Compound 7A after 24, 48, and 72 hours compared with erbB2 treated with vehicle only after 24, 48, and 72 hours.
Figure 3D:
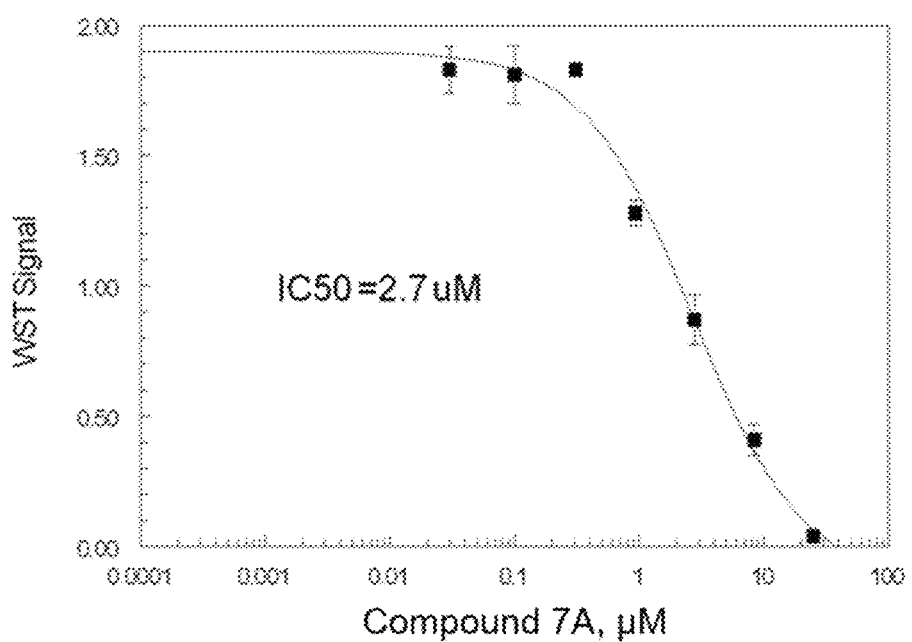
FIG. 3D is a graph depicting a cell viability dose-response curve of Compound 7A inhibiting SK-BR3 breast cancer cell proliferation after 72-hour treatment, indicating $IC_{50}$=2.7 μM as assessed by the WST assay.

After 24 hours treatment with Compound 7A, U937 cells were collected by centrifugation and whole cell lysates were prepared. These lysates were analyzed by Western blot to determine the level of Mcl-1. Western blot analysis was carried out as previously described (Wang et al., 2014 Journal of the American Society of Nephrology DOI: 10.1681/asn.2013060665). The band intensity for Mcl-1 in these samples were normalized to that of tubulin to correct for any inconsistencies in total protein in loading and processing the whole cell lysates. The insert in FIG. 3A showed Western blot band intensities for Mcl-1 and tubulin observed for the untreated U937 cells and those treated with 10 µM Compound 7A and illustrated the decline in Mcl-1 levels induced by the treatment.

In U937 cell line, after 24-hour treatment of Compound 7A at varying concentrations, the normalized level of Mcl-I decreased by 50% when increasing Compound 7A's concentration from 0 to 33 µm, indicating that the compound successfully induced degradation of Mcl-1 in U937 cells. And cell viability decreased to 0 when Mcl-1 level decreased by 50%, indicating that the 50% decrease in Mcl-1 induced by the compound within 24 hours was sufficient to inhibit the proliferation of U937 cells by 100%.

The results indicated that the compound induced partial degradation of Mcl-1 in U937 cells and resulted in the complete inhibition of U937 cell proliferation.

Inhibition Against SK-BR3 Cells and Intracellular erbB2

Another substrate of USP9X is the receptor tyrosine kinase erbB2. The involvement of USP9X in the regulation of erbB2 suggested that its degradation may be induced by treatment with USP9X inhibitors. The breast cancer cell line SK-BR3 expresses high levels of erbB2. This cell line was treated with Compound 7A and the effects on cell viability as well as expression levels of erbB2 were examined.

Compound 7A inhibited the viability of SK-BR3. The levels of erbB2 were determined by Western blot and found to decrease in parallel with the decline in cell viability. After 72-hour treatment of 10 µm Compound 7A, the level of erbB2 declined to about zero. The loss of erbB2 from the plasma membrane was also confirmed by flow cytometry.

The results from both western blot and flow cytometry indicated the compound induced the degradation of erbB2 in SK-BR3 breast cancer cells. From cell viability results after 72-hour treatment with Compound 7A, the compound exhibited an IC$_{50}$ value of 2.7 µM for inhibiting the proliferation of SK-BR3 breast cancer cells by 100%.

Capture ELISA

In addition to Western blot analysis, direct effects of the compounds on cancer related cellular substrates were determined using capture ELISA techniques. Following the treatment of the compound, decreases were detected in erbB2 levels in SK-BR-3, MIA-PaCa-2, BT-549, and MDA-MB-231 cells; and in Mcl-1 levels in SK-BR-3, MIA-PaCa-2, BT-549, and U937 cells. Increases were detected in the level of ubiquitylatededErbB2 in SK-BR-3 cells and in the level of ubiquitylated Mcl-1 in SK-BR-3 cells, MIA-PaCa-2, and BT-549 cells. For SK-BR-3 cells treated, it was also detected the loss of erbB2/erbB3 heterodimers and erbB2 homodimers.

Figure 4A:
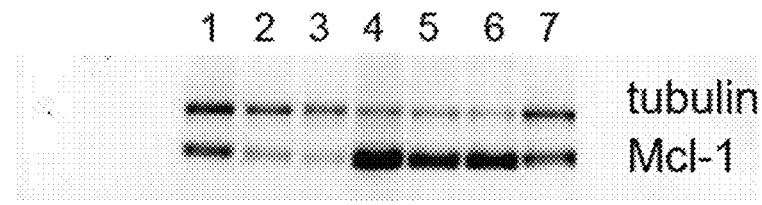
FIG. 4A is a western blot image showing Mcl-1 bands in U937 cell line at different stages of treatments. U937 cells were treated with either 10 μg/mL cycloheximide, 10 μM MG132, the combination of cycloheximide and MG132, or vehicle (DMSO) for one hour prior to the treatment with Compound 5A for 24 hours. Bands of tubulin undergoing the same treatments are shown as a reference.
Figure 4B:
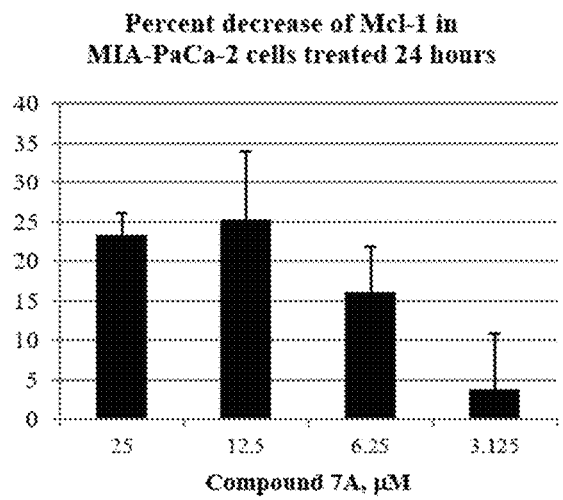
FIG. 4B left is a graph of capture ELISA results showing the percent decreases of Mcl-1 in MIA-PaCa-2 cells treated with Compound 7A at 25 μM, 12.5 μM, 6.25 μM, and 3.125 μM, respectively, for 24 hours. Right is graph of capture ELISA results showing the percent increases of ubiquitylated Mcl-1 in MIA-PaCa-2 cells treated with Compound 7A at 25 μM, 12.5 μM, 6.25 μM, and 3.125 μM, respectively, for 24 hours.
Figure 4B:
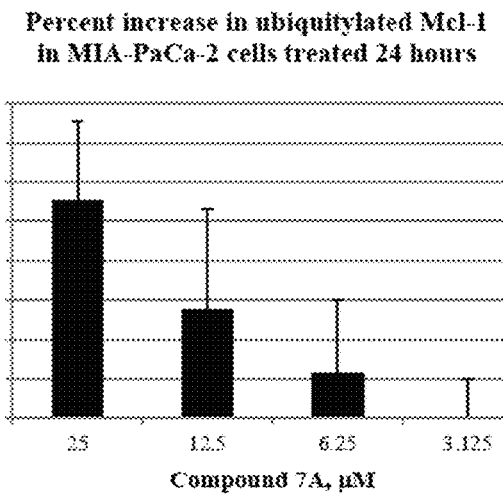
Figure 5A:
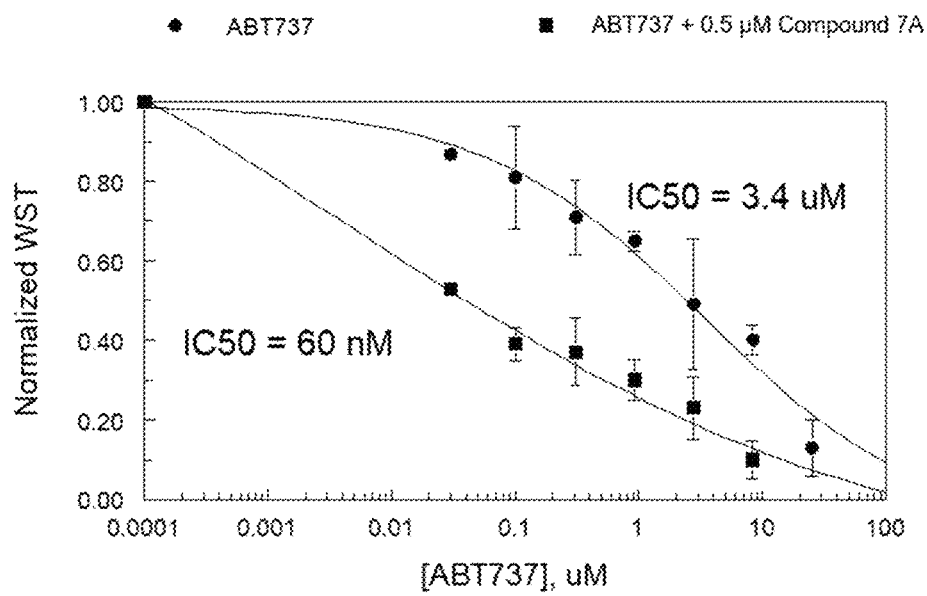
FIG. 5A is a graph depicting cell viability dose-response curves, as assessed by the WST assay, of ABT737 inhibiting U937 cells with and without the co-treatment of 0.5 μM Compound 7A, respectively. With the co-treatment of Compound 7A, the $IC_{50}$ value of ABT737 decreases to 0.06 μM from 3.4 μM when treated with ABT737 alone. Co-treatment of 0.5 μM Compound 7A results in 57-fold enhancement in ABT737's potency for inhibiting U937 cells.
Figure 5B:
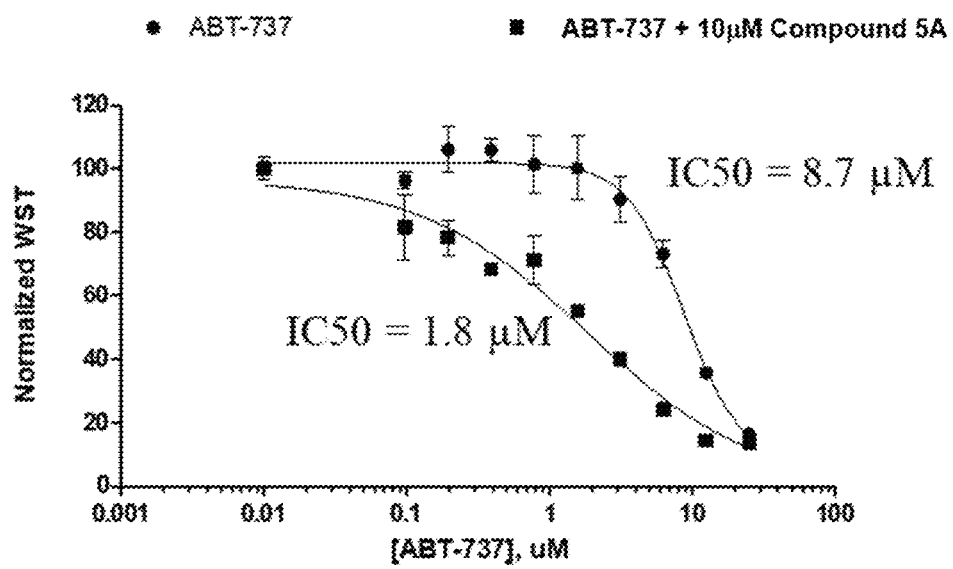
FIG. 5B is a graph depicting cell viability dose-response curves of ABT737 inhibiting MDA-MB-231 cells with and without the co-treatment of 10 μM Compound 5A, respectively. With the co-treatment of Compound 5A, the $IC_{50}$ value of ABT737 decreases to 1.8 μM from 8.7 μM when treated with ABT737 alone. Co-treatment of 10 μM Compound 5A results in 5-fold enhancement in ABT737's potency for inhibiting MDA-MB-231 cells.

Example 4: Investigating Mechanism of Action of Compounds Using Protein Synthesis Inhibitor and Proteasome Inhibitor Western Blot Analysis To investigate the mechanism of action, Western blot analysis was carried out to test the induced degradation of USP9X substrate Mcl-1 by the compounds under the effects of protein synthesis inhibitor cycloheximide and/or proteasome inhibitor MG132. U937 cells were treated with 10 µM cycloheximide for one hour, with 10 µM MG132 for one hour, with the combination of 10 µM cycloheximide and 10 µM MG132 for one hour, and with vehicle (DMSO) for one hour, respectively, prior to the treatment with Compound 5A for 24 hrs. The U937 cells were harvested after treatment and whole cell lysates were prepared. These lysates were analyzed by Western blot to determine the abundance of Mcl-1 as well as that of tubulin as a normalization control. Lanes 1 and 7 of FIG. 4A showed the intensity of the Mcl-1 and tubulin bands for vehicle treated U937 cells. The band intensity of the Mcl-1 in cells treated with cycloheximide alone (Lane 2) was reduced relative to that for tubulin. Intracellular Mcl-1 has a short half-life (approximately 30 minutes). Global blockade of protein synthesis by cycloheximide led to a significant decrease in the expression levels, especially for short lived Mcl-1. The retention of a reduced portion of Mcl-1 indicated the immunity of this portion to proteasomal degradation. The treatment of U937 cells with Compound 5A (Lane 3) resulted in an about 50% reduction of Mcl-1. In contrast, the band intensity of Mcl-1 relative to that of tubulin increased upon treatment of U937 cells with the proteasome inhibitor MG132 (Lane 4). The ability of Compound 5A to induce the degradation of Mcl-1 was blocked by addition of MG132 (Lanes 5 and 6), suggesting that the mechanism for the induced degradation of Mcl-1 was via the proteosome. Together, the results of this Example are consistent with the compounds acting on the proposed mechanism that intracellular inhibition of the deubiquitylase activity of USP9X blocks its ability to rescue USP9X substrates such as Mcl-1 from proteasomal degradation. In other aspects, by varying the concentration ratios of the compound and proteasome inhibitor for treating cells, it was possible to achieve controlled degradation of a USP9X substrate so the substrate could decline to a desirable level rather than degrade entirely.

ELISA Analysis

MIA-PaCa-2 cells were treated with Compound 7A at 25 µM, 12.5 µM, 6.25 µM, and 3.125 µM, respectively, for 24 hours. Capture ELISA of Mcl-1 was performed using a dilution series of MIA-PaCa-2 cell lysates equalized for total protein in a 96-well plate coated with sheep anti-human Mcl-1 (R&D Systems, #AF8281). Detection of Mcl-1 was performed using biotinylated sheep anti-human Mcl-1 followed by streptavidin-horseradish peroxidase and TMB development. For detection of ubiquitylated Mcl-1 the same capture conditions were used but employing a biotinylated mouse anti-human ubiquitin antibody (R&D Systems, #MAB701), again detecting with streptavidin-horseradish peroxidase and TMB development. Lysate samples were run in triplicate and percentages were calculated based on the signal generated from cell lysates with no compound added (vehicle control samples). After treating cells with 25 µM Compound 7A for 24 hours, Mcl-1 declined by about 23.0% whereas ubiquitylated Mcl-1 increased by about 27.5%. With 12.5 µM Compound 7A, Mcl-1 declined by about 25.0% whereas ubiquitylated Mcl-1 increased by about 14.0%.

Treatment of cells with Compound 7A induced the degradation of USP9X substrate Mcl-1. The level of ubiquitylation of Mcl-1 increased even as the level of Mcl-1 expression declined. These results were consistent with the inhibition of USP9X within cells, causing the level of Mcl-1 ubiquitylation to rise and its subsequent degradation in the proteasome.

Example 5: Sensitizing Cells and Enhancing Potency for Other Protein Inhibitor

Mcl-1 can serve as an anti-apoptotic factor conferring resistance to chemotherapy. Western blot analysis was carried out to investigate the effect of the compounds on other inhibitors of which the targeted proteins could otherwise be protected by Mcl-1 and thus resistant to these inhibitors.

In the AML cell line U937, western blot bands showed high intensity for Bcl-xL, medium intensity for Mcl-1, and low intensity for Bcl-2. U937 cells were treated with the Bcl-2/Bcl-xL inhibitor ABT737 72 hours at varying concentrations and underwent western blot analysis. The $IC_{50}$ value of ABT737 was determined to be 3.4 µM from the dose-response curve. In contrast, after adding 0.5 µM Compound 7A to the same treatment, the $IC_{50}$ value of ABT737 was determined to be 0.06 µM from the dose-response curve. Co-treatment of 0.5 µM Compound 7A resulted in 57-fold enhancement in the sensitivity of U937 cells to ABT737.

The TNBC cell line MDA-MB-231 express high levels of Mcl-1 and USP9X in addition to Bcl-2 and Bcl-xL. MDA-MB-231 cells were treated with ABT737 for 72 hours at varying concentrations and underwent western blot analysis. The $IC_{50}$ value of ABT737 was determined to be 8.7 µM from the dose-response curve. In contrast, when co-treated with 10 µM Compound 5A and underwent the same experiments, the $IC_{50}$ value of ABT737 was determined to be 1.8 µM from the dose-response curve. Co-treatment of 10 µM Compound 5A resulted in 5-fold enhancement in the sensitivity of MDA-MB-231 cells to ABT737.

Example 6: Downregulating PD-L1

Programmed death-ligand 1 (PD-L1), an immune-oncology target, has been identified as a substrate for USP9X. PDL1 as a transmembrane protein is expressed on tumor cells and capable of blunting the immune response to tumors by interacting with PD1 on the surface of T cells that otherwise would attack tumor antigens on the surface of these cells and eradicate them. The compounds as described herein induce the targeted degradation of PDL1 from tumor cells and enhance the immune response of T cells against the tumor cells.

MIA PaCa-2 cells expressing detectable levels of PD-L1 are treated with Compound 7A at various concentrations for 24 hours, and the ensuing level of PD-L1 are determined by Western blot to decrease by about 50% after the treatment.

Example 7: In Vivo Animal Model Test

USP9X is highly expressed and activated in melanoma cells. The effect of compounds on USP9X activity in a representative melanoma cell line, A375, and an A375 variant cell line that is resistant to the BRAF kinase inhibitor, vemurafenib, can be examined. Treatment results in inhibition of USP9X activity in either cell type. To determine anti-tumor activity in animals, mice are treated intravenously (IV) or by oral gavage (PO). Compound is administered once to two mice per group at the indicated dosage level and route (IV or PO) and plasma is collected after administration. Compound concentration in the plasma is measured by high performance liquid chromatography coupled with mass spectroscopy detection (LC/MS).

Tumor cells are injected into the dorsal region of twenty female NOD/SCID/gamma-2 knockout mice (NSG) weighing about 20 grams each. After 3 weeks tumors become visible and measurable with calipers. Mice are separated into four groups of 5 mice each and IP injected with the compound of the invention dissolved in 55% dimethyl sulfoxide, 25% polyethylene glycol 300, 20% phosphate-buffered saline at dose levels of 0, 2.5, 5 and 10 mg/kg mouse body weight. Animals are injected once per day for 14 days and tumor growth (measured with calipers) and animal weight are monitored over the treatment interval. Results show that tumor growth in mice treated with the compound at dose levels of 2.5, 5 and 10 mg/kg are inhibited at different levels, compared with that in the group of untreated mice; and the dose of 10 mg/kg of the compound lead to the maximum inhibition of tumor growth by about 80% among the three treated groups, increasing the life span by about 200% compared with untreated mice.

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by formula (IVc):

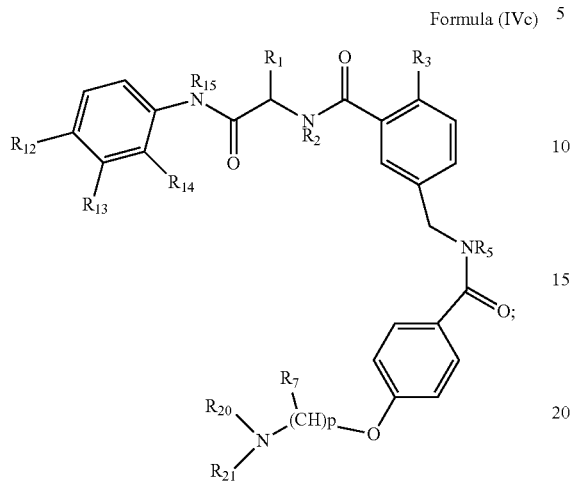

Formula (IVc)

wherein $R_1$ and $R_7$ are each independently selected from the group consisting of H, D, halogen, substituted or unsubstituted alkyl, substituted or unsubstituted aryl, substituted or unsubstituted heteroaryl, substituted or unsubstituted cycloalkyl, and substituted or unsubstituted heterocycloalkyl;

$R_2$ and $R_5$ are each independently selected from the group consisting of H, $^2$H and substituted or unsubstituted alkyl;

$R_3$ is selected from the group consisting of H, D, halogen, and substituted or unsubstituted alkyl;

$R_{12}$ and $R_{13}$ are each selected from the group consisting of: H, halogen, substituted or unsubstituted alkyl, substituted or unsubstituted aryl, alkoxy, —COOCH$_3$, —CONHCH$_3$,

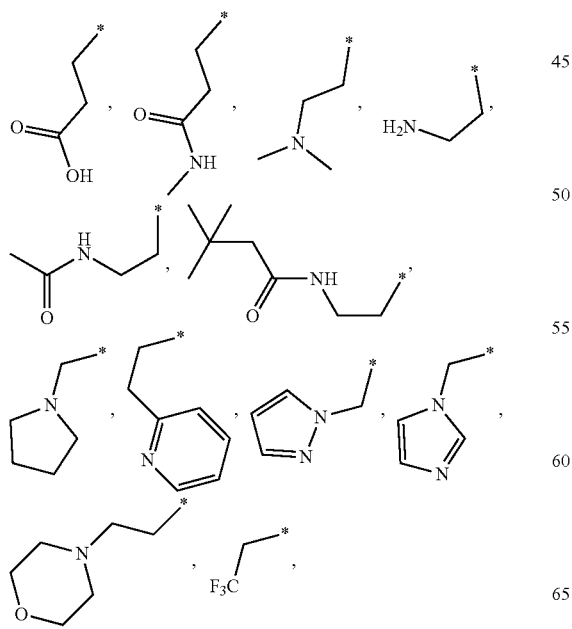

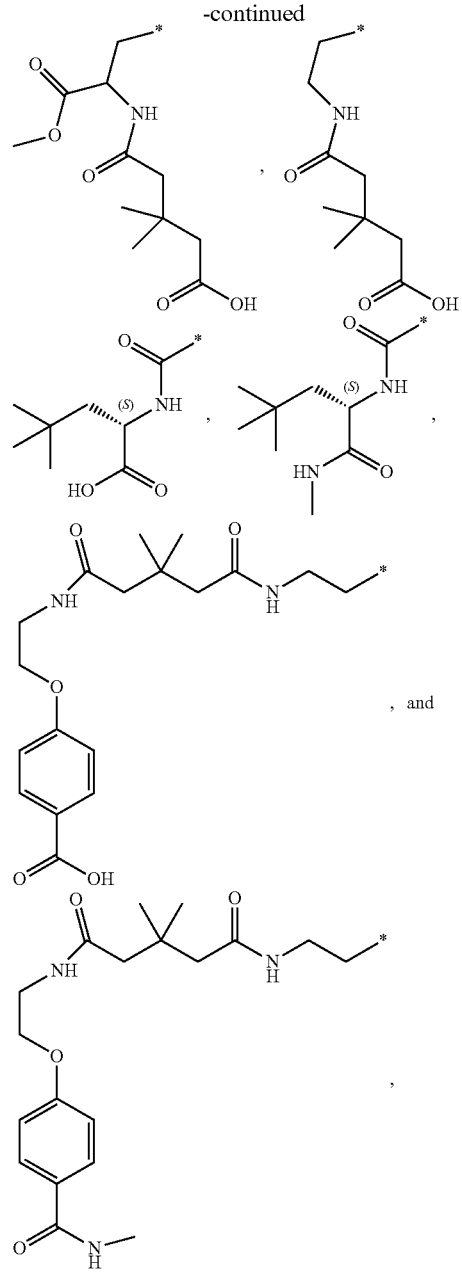

in which * indicates attachment point; and provided that at least one of $R_{12}$ and $R_{13}$ is H or F;

$R_{14}$ is H, halogen, or $C_{1-6}$ alkyl;

$R_{15}$ is H or $C_{1-6}$ alkyl;

$R_{20}$ and $R_{21}$ are each independently selected from the group consisting of H, halogen, substituted or unsubstituted alkyl, substituted or unsubstituted alkenyl, substituted or unsubstituted alkynyl, substituted or unsubstituted aryl, substituted or unsubstituted heteroaryl, substituted or unsubstituted cycloalkyl, and substituted or unsubstituted heterocycloalkyl; alternately $R_{20}$ and $R_{21}$ together with the N to which they are attached form a 5- or 6-membered heterocyclic ring; and p is selected from 0, 1, 2, 3, 4, or 5.

2. The compound of claim 1, wherein $R_1$ is H, —CH$_3$, —CH$_2$CH(CH$_3$)$_2$, or —CH$_2$C(CH$_3$)$_3$.

3. The compound of claim 1, wherein $R_2$ and $R_5$ are H or —CH$_3$.

4. The compound of claim 1, wherein $R_3$ is H or F.
5. The compound of claim 1, wherein p is 0, 1, or 2, and $R_7$ is H, —CH$_3$, or —CH$_2$C(CH$_3$)$_3$.
6. The compound of claim 1, wherein the compound is selected from the group consisting of:
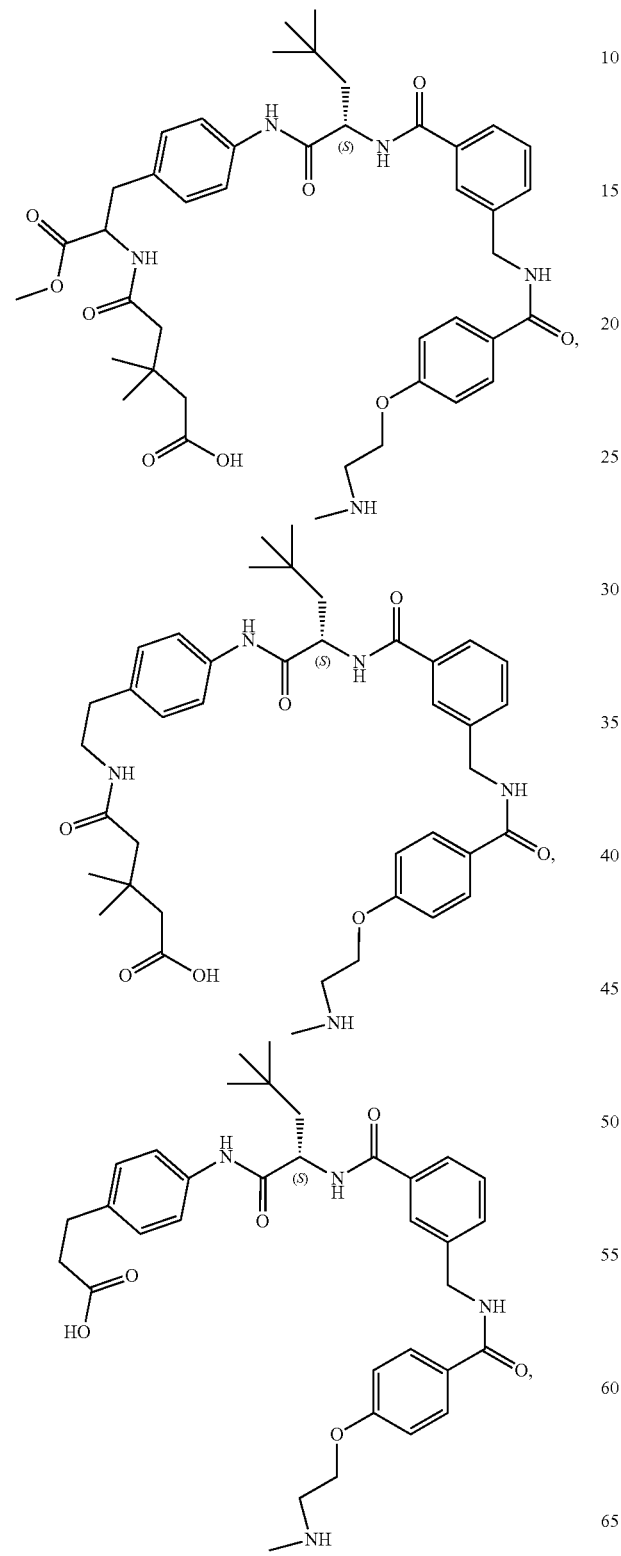
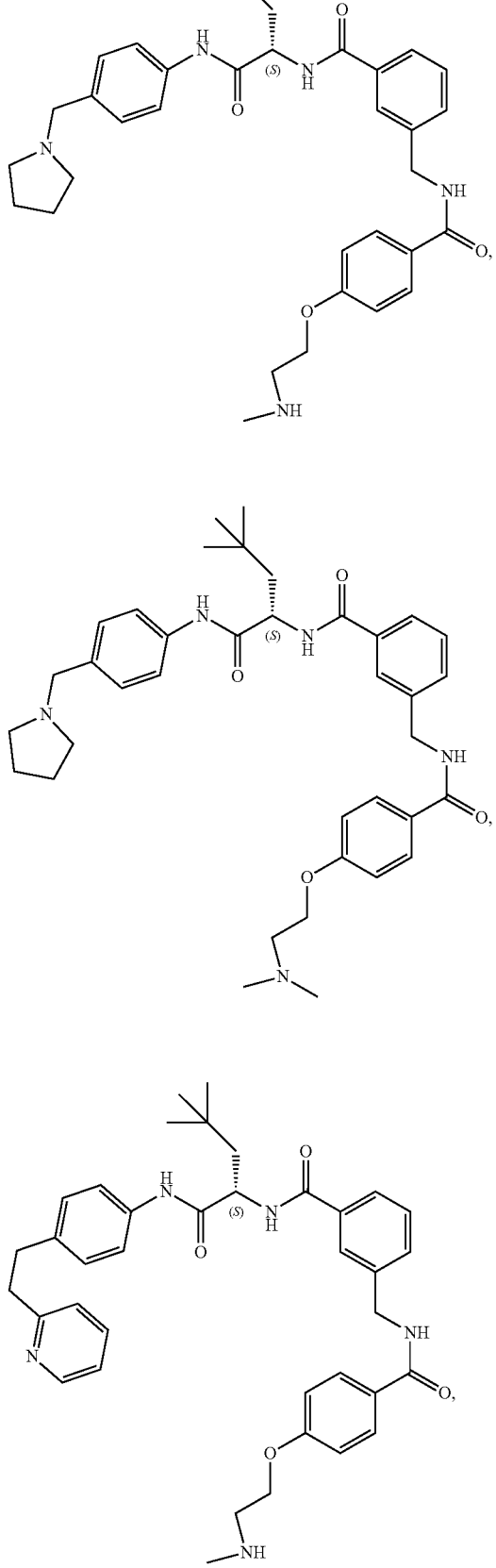

139

-continued

140

-continued

141
-continued
142
-continued
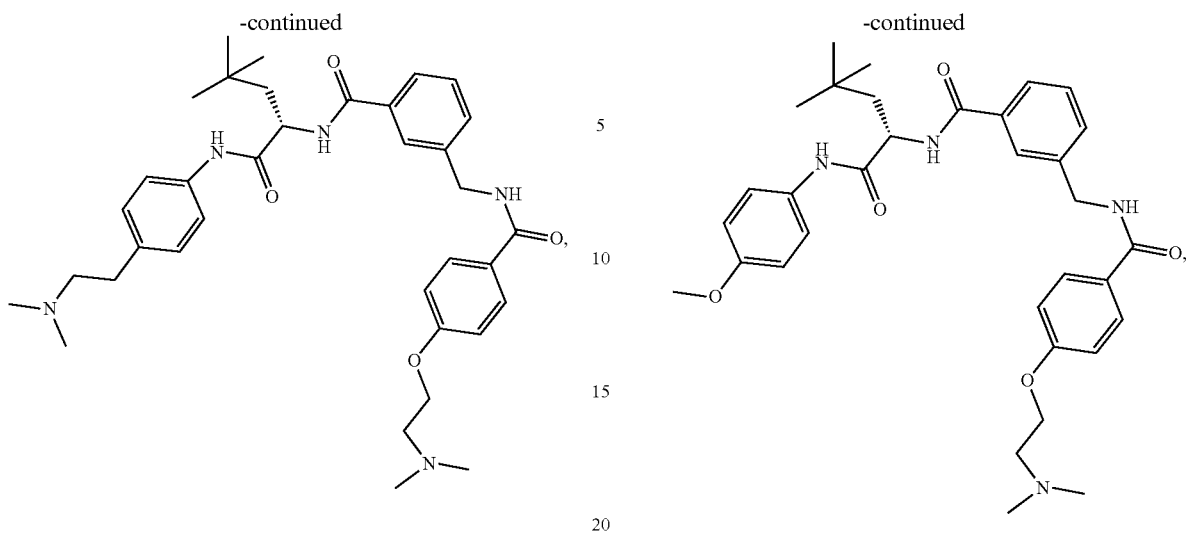
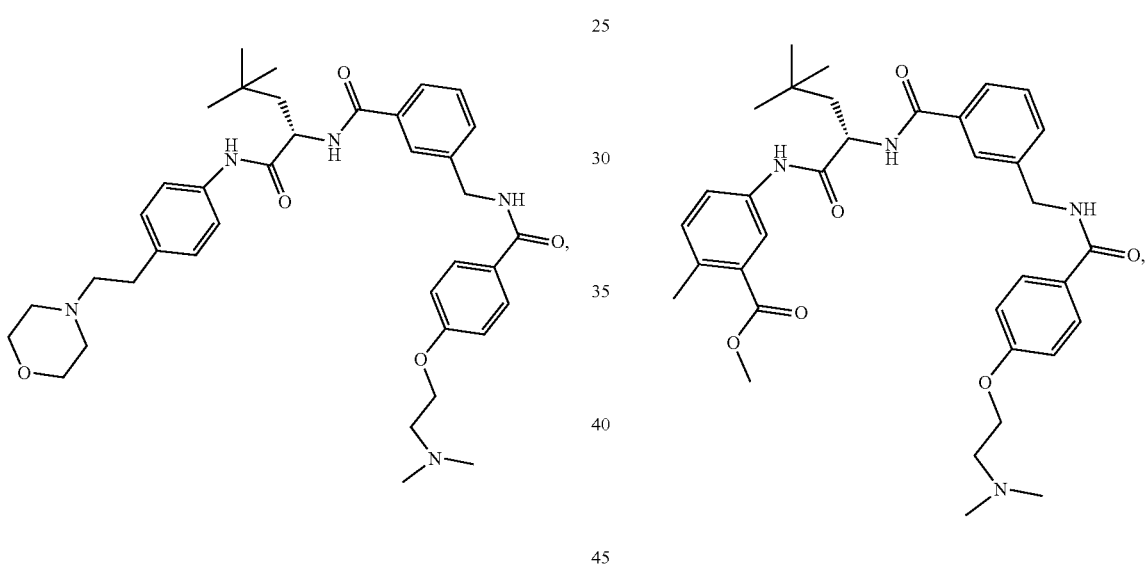
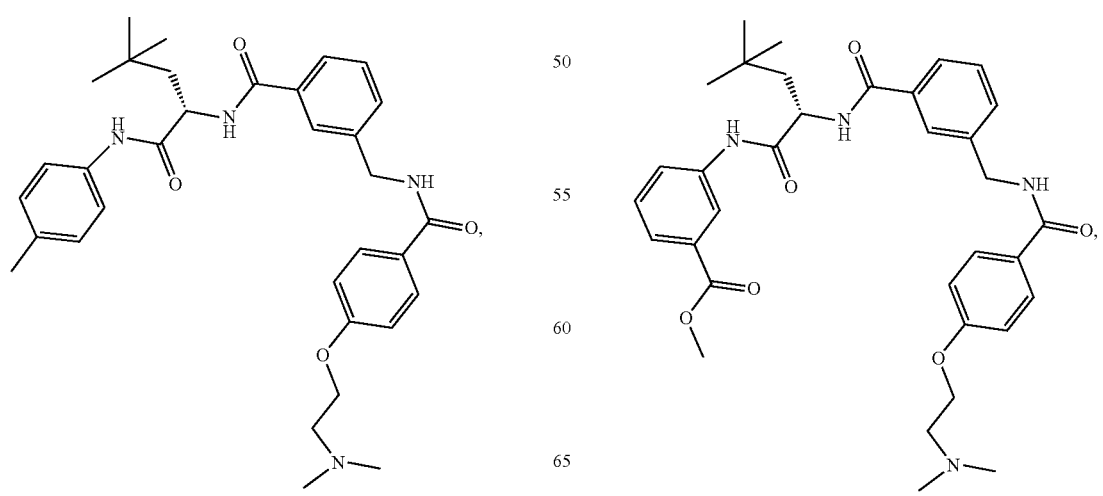

143
-continued
144
-continued
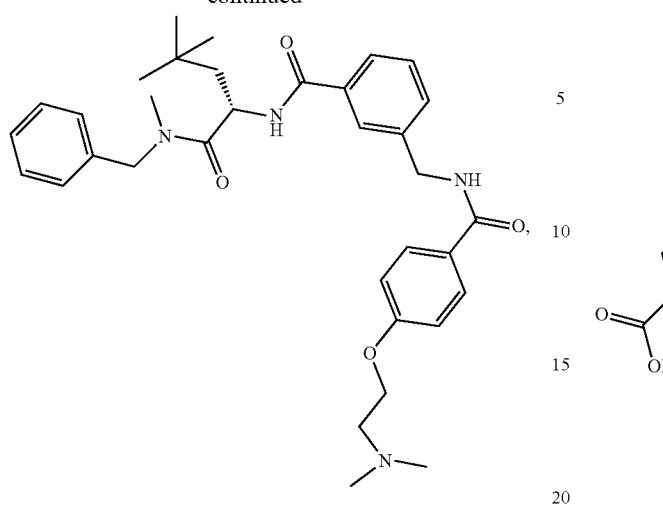
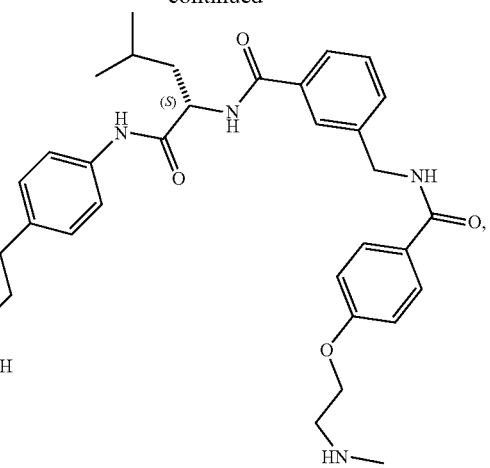
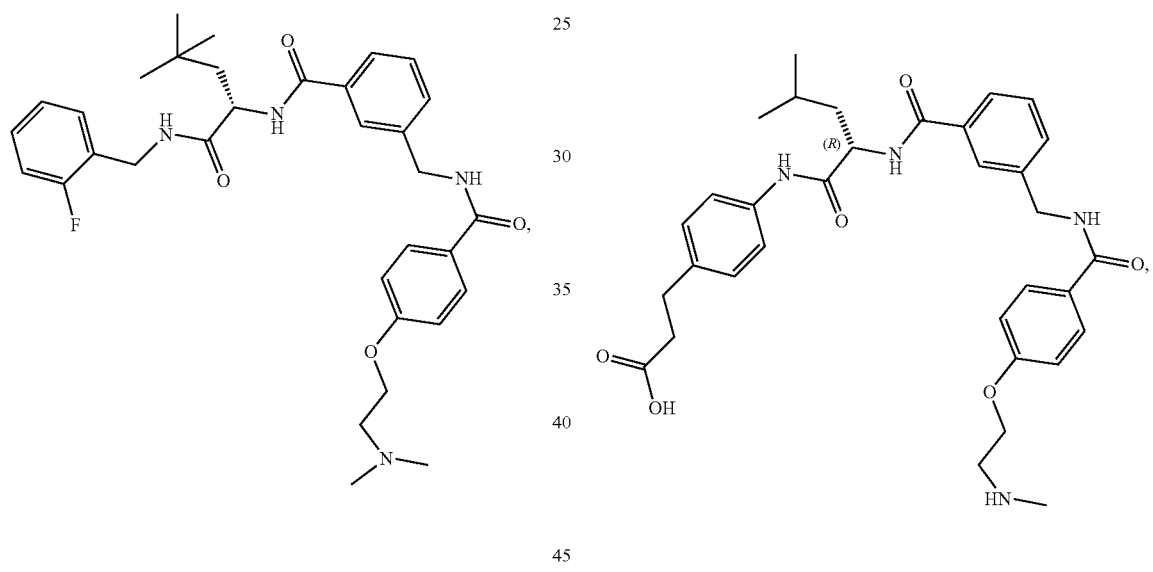
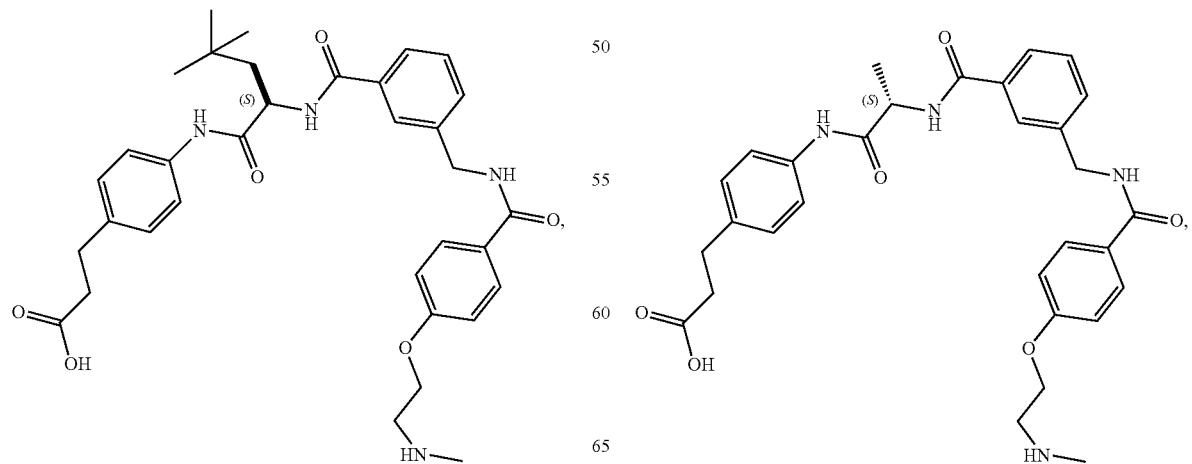

145
-continued
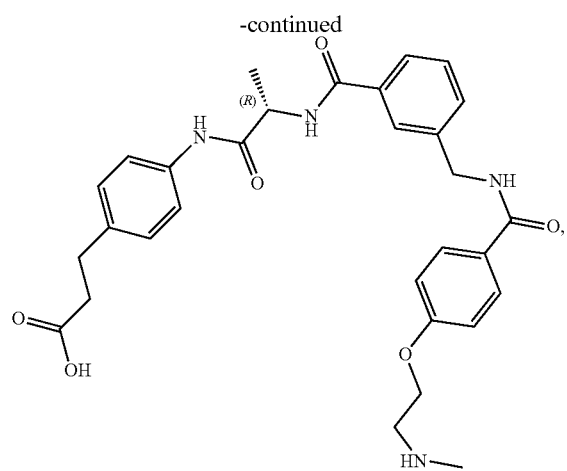
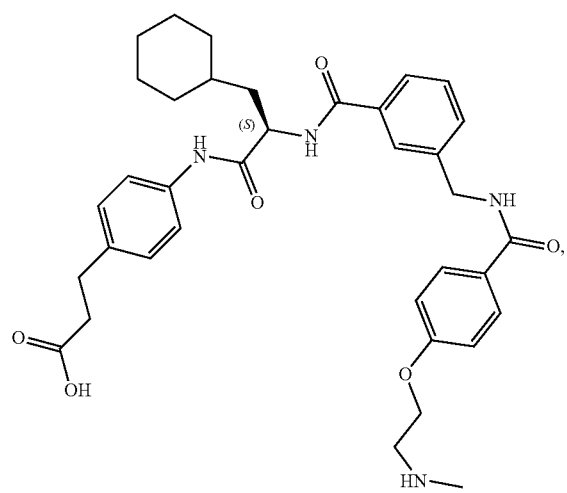
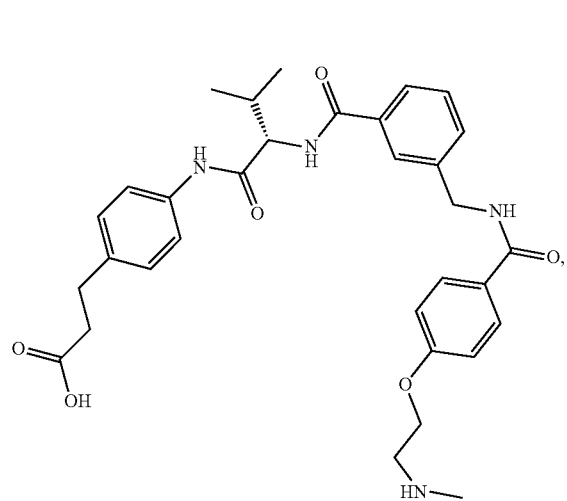
146
-continued
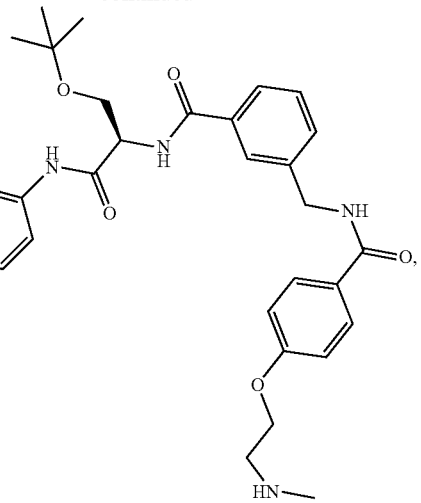
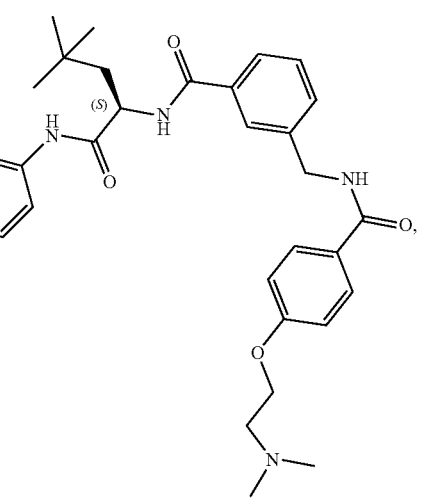
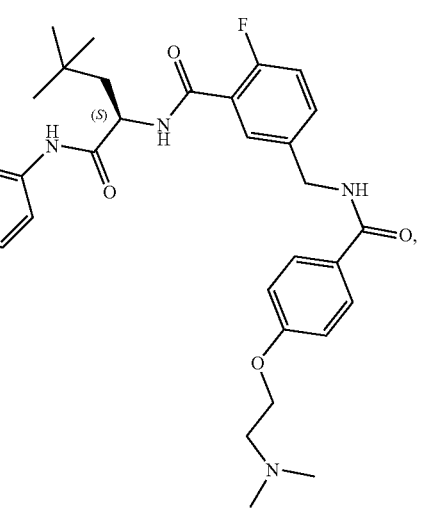

147
-continued
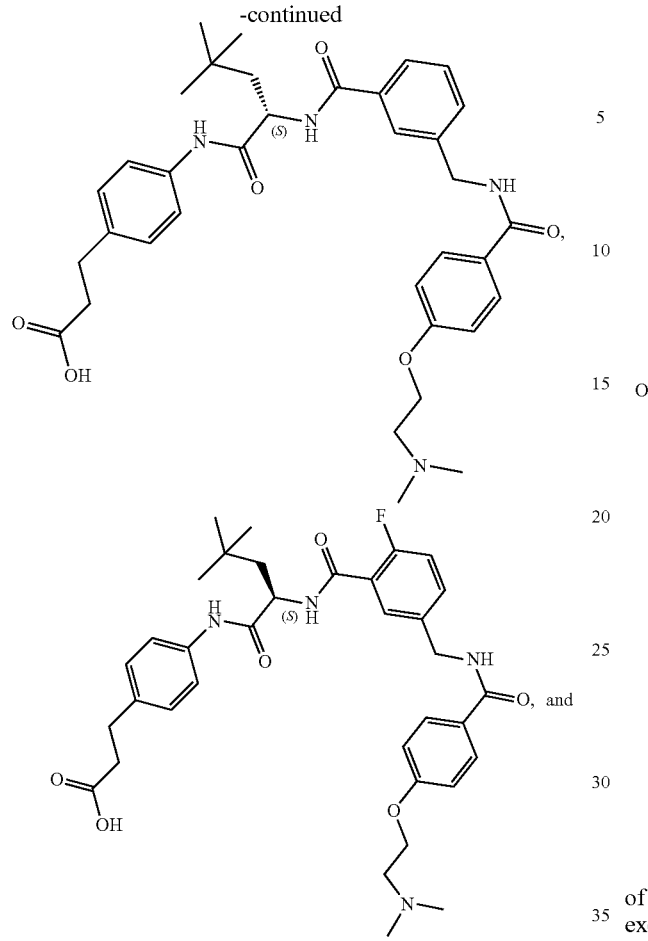
148
-continued
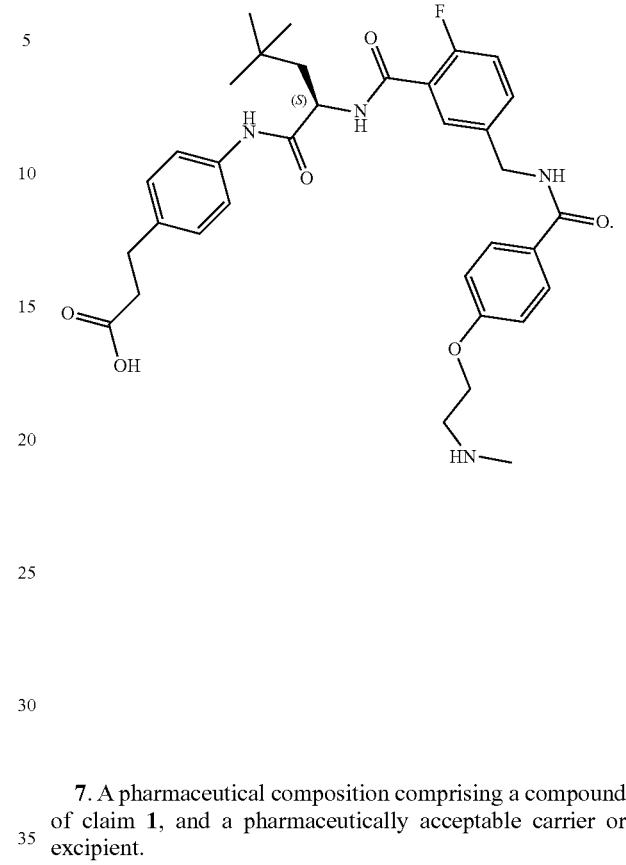
7. A pharmaceutical composition comprising a compound of claim 1, and a pharmaceutically acceptable carrier or excipient.
* * * * *